(12) United States Patent
Arvedson et al.

(10) Patent No.: US 9,688,759 B2
(45) Date of Patent: *Jun. 27, 2017

(54) FERROPORTIN ANTIBODIES AND METHODS OF USE

(71) Applicant: AMGEN INC., Thousand Oaks, CA (US)

(72) Inventors: Tara Arvedson, Simi Valley, CA (US); Gregory Dyas, Carmel, IN (US); James B. Rottman, Sudbury, MA (US); Barbra Sasu, San Bruno, CA (US); Xiao-juan Bi, Newbury Park (CA); Grace Ki Jeong Lee, Simi Valley, CA (US); Jackie Z. Sheng, Thousand Oaks, CA (US)

(73) Assignee: Amgen, Inc., Thousand Oaks, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/866,105

(22) Filed: Sep. 25, 2015

(65) Prior Publication Data

US 2016/0083470 A1 Mar. 24, 2016

Related U.S. Application Data

(63) Continuation of application No. 12/863,737, filed as application No. PCT/US2009/031851 on Jan. 23, 2009, now Pat. No. 9,175,078.

(60) Provisional application No. 61/121,729, filed on Dec. 11, 2008, provisional application No. 61/023,693, filed on Jan. 25, 2008.

(51) Int. Cl.
| | | |
|---|---|---|
| C07K 16/28 | (2006.01) | |
| G01N 33/68 | (2006.01) | |
| G01N 33/90 | (2006.01) | |
| A61K 38/18 | (2006.01) | |
| A61K 39/395 | (2006.01) | |
| A61K 39/00 | (2006.01) | |

(52) U.S. Cl.
CPC .......... *C07K 16/28* (2013.01); *A61K 38/1816* (2013.01); *A61K 39/3955* (2013.01); *G01N 33/6872* (2013.01); *G01N 33/90* (2013.01); *A61K 2039/505* (2013.01); *C07K 2317/21* (2013.01); *C07K 2317/34* (2013.01); *C07K 2317/56* (2013.01); *C07K 2317/565* (2013.01); *C07K 2317/70* (2013.01); *C07K 2317/76* (2013.01); *G01N 2800/00* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,850,752 A | 11/1974 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,179,337 A | 12/1979 | Davis et al. |
| 4,301,144 A | 11/1981 | Iwashita et al. |
| RE30,985 E | 6/1982 | Cartaya |
| 4,376,110 A | 3/1983 | David et al. |
| 4,452,901 A | 6/1984 | Gordon et al. |
| 4,495,285 A | 1/1985 | Shimizu et al. |
| 4,496,689 A | 1/1985 | Mitra |
| 4,560,655 A | 12/1985 | Baker |
| 4,609,546 A | 9/1986 | Hiratani |
| 4,640,835 A | 2/1987 | Shimizu et al. |
| 4,657,866 A | 4/1987 | Kumar |
| 4,667,016 A | 5/1987 | Lai et al. |
| 4,670,417 A | 6/1987 | Iwasaki et al. |
| 4,676,980 A | 6/1987 | Segal et al. |
| 4,703,008 A | 10/1987 | Lin |
| 4,766,106 A | 8/1988 | Katre et al. |
| 4,767,704 A | 8/1988 | Cleveland et al. |
| 4,791,192 A | 12/1988 | Nakagawa et al. |
| 4,927,762 A | 5/1990 | Darfler |
| 5,122,469 A | 6/1992 | Mather et al. |
| 5,223,409 A | 6/1993 | Ladner et al. |
| 5,229,275 A | 7/1993 | Goroff |
| 5,244,805 A | 9/1993 | Miller |
| 5,338,665 A | 8/1994 | Schatz et al. |
| 5,359,681 A | 10/1994 | Jorgenson et al. |
| 5,432,018 A | 7/1995 | Dower et al. |

(Continued)

FOREIGN PATENT DOCUMENTS

| | | |
|---|---|---|
| EP | 315 456 A2 | 5/1989 |
| EP | 404 097 B1 | 12/1990 |

(Continued)

OTHER PUBLICATIONS

Janeway et al., Immunobiology, 3rd edition, 1997, Garland Press, pp. 3:1-3:11.*

(Continued)

*Primary Examiner* — Michael Szperka
(74) *Attorney, Agent, or Firm* — Lawrence Bugaisky; Jonathan M. Dermott

(57) ABSTRACT

Compositions for treating disorders of iron homeostasis are provided. More particularly, anti-ferroportin antibodies, compositions containing such antibodies, corresponding nucleic acids, vectors and host cells, and methods of making such antibodies are provided.

12 Claims, 15 Drawing Sheets

(56) References Cited

U.S. PATENT DOCUMENTS

| | | |
|---|---|---|
| 5,441,868 A | 8/1995 | Lin |
| 5,498,530 A | 3/1996 | Schatz et al. |
| 5,530,101 A | 6/1996 | Queen et al. |
| 5,545,807 A | 8/1996 | Surani et al. |
| 5,547,933 A | 8/1996 | Lin |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,589,369 A | 12/1996 | Seidman et al. |
| 5,591,669 A | 1/1997 | Krimpenfort et al. |
| 5,618,698 A | 4/1997 | Lin |
| 5,621,080 A | 4/1997 | Lin |
| 5,693,762 A | 12/1997 | Queen et al. |
| 5,733,731 A | 3/1998 | Schatz et al. |
| 5,756,349 A | 5/1998 | Lin |
| 5,766,866 A | 6/1998 | Center et al. |
| 5,766,886 A | 6/1998 | Studnicka et al. |
| 5,767,078 A | 6/1998 | Johnson et al. |
| 5,773,569 A | 6/1998 | Wrighton et al. |
| 5,830,851 A | 11/1998 | Wrighton et al. |
| 5,856,298 A | 1/1999 | Strickland |
| 5,877,293 A | 3/1999 | Adair et al. |
| 5,922,545 A | 7/1999 | Mattheakis et al. |
| 5,939,598 A | 8/1999 | Kucherlapati et al. |
| 5,955,422 A | 9/1999 | Lin |
| 5,986,047 A | 11/1999 | Wrighton et al. |
| 5,989,830 A | 11/1999 | Davis et al. |
| 6,054,287 A | 4/2000 | Gao et al. |
| 6,150,584 A | 11/2000 | Kucherlapati et al. |
| 6,171,586 B1 | 1/2001 | Lam et al. |
| 6,306,393 B1 | 10/2001 | Goldenberg |
| 6,310,078 B1 | 10/2001 | Connolly et al. |
| 6,391,633 B1 | 5/2002 | Stern et al. |
| 6,583,272 B1 | 6/2003 | Bailon |
| 6,586,398 B1 | 7/2003 | Kinstler et al. |
| 6,750,369 B2 | 6/2004 | Connolly et al. |
| 6,900,292 B2 | 5/2005 | Sun et al. |
| 7,030,226 B2 | 4/2006 | Sun et al. |
| 7,084,245 B2 | 8/2006 | Holmes et al. |
| 7,166,448 B1 | 1/2007 | Zon et al. |
| 7,217,689 B1 | 5/2007 | Elliott et al. |
| 8,183,346 B2 | 5/2012 | Leung et al. |
| 8,679,497 B2 * | 3/2014 | Leung .................. C07K 16/28 424/133.1 |
| 9,175,078 B2 * | 11/2015 | Arvedson ............. C07K 16/28 |
| 2002/0004215 A1 | 1/2002 | Osbourn et al. |
| 2002/0061590 A1 | 5/2002 | Glucksmann et al. |
| 2002/0091240 A1 | 7/2002 | Vasquez et al. |
| 2002/0155998 A1 | 10/2002 | Young et al. |
| 2002/0199213 A1 | 12/2002 | Tomizuka et al. |
| 2003/0031667 A1 | 2/2003 | Deo et al. |
| 2003/0044772 A1 | 3/2003 | Watkins et al. |
| 2003/0077753 A1 | 4/2003 | Tischer |
| 2003/0082749 A1 | 5/2003 | Sun et al. |
| 2003/0092125 A1 | 5/2003 | Davis et al. |
| 2003/0113316 A1 | 6/2003 | Kaisheva et al. |
| 2003/0118592 A1 | 6/2003 | Ledbetter et al. |
| 2003/0133939 A1 | 7/2003 | Ledbetter et al. |
| 2003/0143202 A1 | 7/2003 | Binley et al. |
| 2003/0190317 A1 | 10/2003 | Baca et al. |
| 2003/0194404 A1 | 10/2003 | Greenfeder et al. |
| 2003/0215444 A1 | 11/2003 | Elliott |
| 2004/0009902 A1 | 1/2004 | Boime et al. |
| 2004/0071694 A1 | 4/2004 | DeVries et al. |
| 2004/0091961 A1 | 5/2004 | Evans et al. |
| 2004/0143857 A1 | 7/2004 | Young et al. |
| 2004/0157293 A1 | 8/2004 | Evans et al. |
| 2004/0175379 A1 | 9/2004 | DeVries et al. |
| 2004/0175824 A1 | 9/2004 | Sun et al. |
| 2004/0229318 A1 | 11/2004 | Heavner |
| 2004/0248815 A1 | 12/2004 | Connolly et al. |
| 2004/0266690 A1 | 12/2004 | Pool |
| 2005/0019914 A1 | 1/2005 | Staerk et al. |
| 2005/0020487 A1 | 1/2005 | Klaus et al. |
| 2005/0026834 A1 | 2/2005 | Cox, III et al. |
| 2005/0037421 A1 | 2/2005 | Honda et al. |
| 2005/0096461 A1 | 5/2005 | Cox, III |
| 2005/0107297 A1 | 5/2005 | Holmes et al. |
| 2005/0107591 A1 | 5/2005 | Cox, III |
| 2005/0124045 A1 | 6/2005 | Sun et al. |
| 2005/0124564 A1 | 6/2005 | Binley et al. |
| 2005/0136049 A1 | 6/2005 | Ledbetter et al. |
| 2005/0137329 A1 | 6/2005 | Holmes et al. |
| 2005/0142642 A1 | 6/2005 | Sun et al. |
| 2005/0143292 A1 | 6/2005 | DeFrees et al. |
| 2005/0153879 A1 | 7/2005 | Svetina et al. |
| 2005/0158822 A1 | 7/2005 | Pecker |
| 2005/0158832 A1 | 7/2005 | Young et al. |
| 2005/0170457 A1 | 8/2005 | Pool et al. |
| 2005/0181359 A1 | 8/2005 | Optelten et al. |
| 2005/0181482 A1 | 8/2005 | Meade et al. |
| 2005/0192211 A1 | 9/2005 | Gillies et al. |
| 2005/0202538 A1 | 9/2005 | Gillies et al. |
| 2005/0227289 A1 | 10/2005 | Reilly et al. |
| 2005/0244409 A1 | 11/2005 | Erickson-Miller et al. |
| 2006/0040858 A1 | 2/2006 | Holmes et al. |
| 2006/0088906 A1 | 4/2006 | DeFrees et al. |
| 2006/0111279 A1 | 5/2006 | DeFrees et al. |
| 2006/0223114 A1 | 10/2006 | Stemmer et al. |
| 2006/0286603 A1 | 12/2006 | Kolkman et al. |
| 2007/0218055 A1 | 9/2007 | Zon et al. |

FOREIGN PATENT DOCUMENTS

| | | |
|---|---|---|
| WO | WO 87/05330 A1 | 9/1987 |
| WO | WO 87/00195 A2 | 5/1989 |
| WO | WO 90/03430 A1 | 4/1990 |
| WO | WO 91/05867 A1 | 5/1991 |
| WO | WO 91/10741 A1 | 11/1991 |
| WO | WO 91/17271 A1 | 11/1991 |
| WO | WO 92/01047 A1 | 1/1992 |
| WO | WO 92/11018 A1 | 9/1992 |
| WO | WO 93/11161 A1 | 6/1993 |
| WO | WO 93/11236 A1 | 6/1993 |
| WO | WO 93/19172 A1 | 9/1993 |
| WO | WO 94/02602 A1 | 2/1994 |
| WO | WO 94/13806 A1 | 6/1994 |
| WO | WO 95/05465 A1 | 2/1995 |
| WO | WO 95/15388 A1 | 6/1995 |
| WO | WO 96/27011 A1 | 9/1996 |
| WO | WO 96/30498 A1 | 10/1996 |
| WO | WO 96/33735 A1 | 10/1996 |
| WO | WO 96/34096 A1 | 10/1996 |
| WO | WO 96/40987 A1 | 12/1996 |
| WO | WO 98/15833 A2 | 4/1998 |
| WO | WO 98/24893 A2 | 6/1998 |
| WO | WO 98/25965 A2 | 6/1998 |
| WO | WO 99/66054 A2 | 12/1999 |
| WO | WO 00/24782 A2 | 5/2000 |
| WO | WO 00/24893 A2 | 5/2000 |
| WO | WO 00/61637 A1 | 10/2000 |
| WO | WO 01/36489 A2 | 5/2001 |
| WO | WO 01/81405 A2 | 11/2001 |
| WO | WO 02/14356 A2 | 2/2002 |
| WO | WO 02/19963 A2 | 3/2002 |
| WO | WO 02/20034 A1 | 3/2002 |
| WO | WO 02/49673 A2 | 6/2002 |
| WO | WO 02/085940 A2 | 10/2002 |
| WO | WO 03/029291 A2 | 4/2003 |
| WO | WO 03/055526 A2 | 7/2003 |
| WO | WO 03/084477 A2 | 10/2003 |
| WO | WO 03/094858 A2 | 10/2003 |
| WO | WO 2004/002417 A2 | 1/2004 |
| WO | WO 2004/002424 A2 | 1/2004 |
| WO | WO 2004/009627 A1 | 1/2004 |
| WO | WO 2004/018667 A1 | 3/2004 |
| WO | WO 2004/024761 A1 | 3/2004 |
| WO | WO 2004/033651 A2 | 4/2004 |
| WO | WO 2004/035603 A2 | 4/2004 |
| WO | WO 2004/043382 A2 | 5/2004 |
| WO | WO 2004/097019 A1 | 11/2004 |
| WO | WO 2004/101600 A2 | 11/2004 |
| WO | WO 2004/101606 A2 | 11/2004 |

(56) References Cited

FOREIGN PATENT DOCUMENTS

| WO | WO 2004/101611 A2 | 11/2004 | |
|---|---|---|---|
| WO | WO 2004/106373 A1 | 12/2004 | |
| WO | WO 2005/001025 A2 | 1/2005 | |
| WO | WO 2005/001136 A1 | 1/2005 | |
| WO | WO 2005/021579 A2 | 3/2005 | |
| WO | WO 2005/025606 A1 | 3/2005 | |
| WO | WO 2005/032460 A2 | 4/2005 | |
| WO | WO 2005/047328 A2 | 5/2005 | |
| WO | WO 2005/051327 A2 | 6/2005 | |
| WO | WO 2005/092369 A2 | 6/2005 | |
| WO | WO 2005/063808 A1 | 7/2005 | |
| WO | WO 2005/063809 A1 | 7/2005 | |
| WO | WO 2005/070451 A1 | 8/2005 | |
| WO | WO 2005/081687 A2 | 9/2005 | |
| WO | WO 2005/084711 A1 | 9/2005 | |
| WO | WO 2005/100403 A2 | 10/2005 | |
| WO | WO 2005/103076 A2 | 11/2005 | |
| WO | WO 2006/002646 A2 | 1/2006 | |
| WO | WO 2006/029094 A2 | 3/2006 | |
| WO | WO 2006/050959 A2 | 5/2006 | |
| WO | WO 2008097461 A2 * | 8/2008 | ......... A61K 39/3955 |
| WO | WO 2009/035577 A1 | 3/2009 | |

OTHER PUBLICATIONS

Rudikoff et al., Proc Natl Acad Sci USA, 1982, 79:1979-1983.*
Portolano et al., J. Immunol., 1993, 150:880-887.*
William E. Paul, M.D. ed., Fundamental Immunology, 3d ed. 1993, p. 242.*
Kaplan et al., Int J Hematol. Jan. 2011;93(1):14-20. doi: 10.1007/s12185-010-0760-0. Epub Jan. 7, 2011.*
Abboud et al., "A Novel Mammalian Iron-regulated Protein Involved in Intracellular Iron Metabolism," J Biol Chem, 275(26): 19906-19912, (2000).
Adams et al., "Expression of ferroportin in hemochromatosis liver", Blood Cells, Molecules & Diseases, 31(2): 256-261, (2003).
Al-Obeidi et al., "Peptide and Peptidomimetic Libraries: Molecular Diversity and Drug Design," Mol. Biotechnol., 9(3):205-223 (1998).
Aplin and Wriston, "Preparation, Properties, and Applications of Carbohydrate Conjugates of Proteins and Lipids," CRC Crit. Rev. Biochem., pp. 259-306 (1981).
Barnes et al., "Methods for Growth of Cultured Cells in Serum-Free Medium," Anal. Biochem., 102(2):255-270 (1980).
Bastin, et al., "Localisation of Proteins of Iron Metabolism in the Human placenta and liver," British J. Hematol., 134: 532-543 (2006).
Better, et al., "Escherichia coli Secretion of an Active Chimeric Antibody Fragment," Science, 240:1041-1043 (1988).
Bhatnagar, et al., "Structure-Activity Relationships of Novel Hematoregulatory Peptides," J. Med. Chem., 39:3814-3819 (1996).
Biocca, et al., "Expression and targeting of intracellular antibodies in mammalian cells," EMBO J. 9(1):101-108, ( 1990).
Bird, et al., "Single-Chain Antigen-Binding Proteins," Science, 242:423-426, (1988).
Boder, et al., "Yeast surface display for screening combinatorial polypeptide libraries," Nature 15: 553-567, (1997).
Boulianne, et al., "Production of functional chimaeric mouse/human antibody," Nature, 312:643-646 (1984).
Brennan et al., "Preparation of Bispecific Antibodies by Chemical Recombination of Monoclonal Immunoglobulin $G_1$ Fragments," Science, 229(4708):81-83 (1985).
Brüggemann et al., "Designer Mice: The Production of Human Antibody Repertoires in Transgenic Animals," Year in Immunol., 7:33-40 (1993).
Burton and Barbas III, "Human Antibodies from Combinatorial Libraries," Advances in. Immunol., 57:191-280 (1994).
Cane, et al., "Harnessing the Biosynthetic Code: Combinations, Permutations, and Mutations," Science, 282:63-68 (1998).

Canonne-Hergaux, et al., "Comparative studies of duodenal and macrophage ferroportin proteins," Am. J Physiol. Gastrointest. Liver Physiol. 290:G156-GG163 (2006).
Caron et al., "Engineered Humanized Dimeric Forms of IgG Are More Effective Antibodies," J. Exp. Med., 176:1191-1195 (1992).
Carpenter et al., "Interactions of stabilizing additives with proteins during freeze-thawing and freeze-drying," Developments in Biological Standardization, vol. 74, (Karger, Basel (1991)) pp. 225-239.
Carter et al., "High Level Escherichia coli Expression and Production of a Bivalent Humanized Antibody Fragment," Bio/Technology, 10:163-167 (1992).
Caton et al, "Influenza virus hemagglutinin-specific antibodies isolated from a combinatorial expression library are closely related to the immune response of the donor," Proc. Natl. Acad. Sci. USA, 87:6450-6454 (1990).
Champe et al., "Monoclonal Antibodies That Block the Activity of Leukocyte Function-associated Antigen 1 Recognize Three Discrete Epitopes in the Inserted Domain of CD11a," J. Biol. Chem., 270(3):1388-1394 (1995).
Chen, "Formulation Concerns of Protein Drugs," Drug Development and Industrial Pharmacy, 18:1311-1354 (1992).
Chothia et al., "Canonical Structures for the Hypervariable Regions of Immunoglobulins," J. Mol.Biol., 196: 901-917 (1987).
Chowdhury, "Targeting Random Mutations to Hotspots in Antibody Variable Domains for Affinity Improvement," Methods Mol. Biol., Antibody Phage Display: Methods and Protocols, vol. 178, Ch. 24, Eds. O'Brien and Aiken, (Humana Press Inc., Totowa, NJ (2001)) pp. 269-285.
Clackson and Wells, "In vitro selection from protein and peptide libraries," Trends Biotechnol., 12:173-184 (1994).
Clackson et al., "A Hot Spot of Binding Energy in a Hormone-Receptor Interface," Science, 267: 383-386 (1995).
Co et al., "A Humanized Antibody Specific for the Platelet Integrin gpIIb/IIIa," J. Immunol., 152:2968-2976, (1994).
Cochran et al., "The Relationship of MHC-Peptide Binding and T Cell Activation Probed Using Chemically Defined MHC Class II Oligomers," Immunity, 12(3): 241-250 (2000).
Colby et al., "Potent inhibition of huntingtin aggregation and cytotoxicity by a disulfide bond-free single-domain intracellular antibody," Proc. Natl. Acad. Sci. USA, 101(51):1761617621 (2004).
Conrath et al., "β-Lactamase Inhibitors Derived from Single-Domain Antibody Fragments Elicited in the Camelidae," Antimicrob. Agents Chemotherapy, 45: 2807-2812 (2001).
Cortese et al., "Selection of biologically active peptides by phage display of random peptide libraries," Curr. Opin. Biotechnol., 7: 616-621 (1996).
Cortez-Retamozo et al., "Efficient Cancer Therapy with a Nanobody-Based Conjugate," Cancer Research, 64:2853-2857, 2004.
Cotes and Bangham, "Bio-Assay of Erythropoietin in Mice Made Polycythaemic by Exposure to Air at a Reduced Pressure," Nature, 191:1065-1067 (1961).
Creighton, "Proteins: Structures and Molecular Principles," (W.H. Freeman & Co., (1983)) pp. 79-86.
Cunningham et al., "High-Resolution Epitope Mapping of hGH-Receptor Interactions by Alanine-Scanning Mutagenesis," Science, 244:1081-1085 (1989).
Cuthbertson et al., "Design of Low Molecular Weight Hematoregulatory Agents from the Structure-Activity Relationship of a Dimeric Pentapeptide," J. Med. Chem., 40: 28762882 (1997).
Cwirla et al., "Peptide Agonist of the Thrombopoietin Receptor as Potent as the Natural Cytokine," Science, 276: 1696-1699 (1997).
Dall'Acqua et al., "Antibody engineering," Curr. Opin. Struct. Biol., 8:443-450 (1998).
Daugherty et al., "Quantitative analysis of the effect of the mutation frequency on the affinity maturation of single chain Fv antibodies," Proc. Natl. Acad. Sci. USA, 97(5):20292034 (2000).
De Domenico et al., "The Hepcidin-Binding Site on Ferroportin Is Evolutionarily Conserved," Cell Metabolism 8:146-156 (2008).
De Domenico, et al., "The Molecular Mechanism of Hepcidin-mediated Ferroportin Down-Regulation," Mol. Biol. Cell., 18:2569-2578, (2007).

(56) References Cited

OTHER PUBLICATIONS

De Domenico, et al., "The Molecular Basis of Ferroportin-linked Hemochromatosis," Proc. Natl. Acad. Sci. USA, 102(25):8955-8960 (2005).
Delaby, et al., "Presence of the iron exporter ferroportin at the plasma membrane of macrophages is enhanced by iron loading and down-regulated by Hepcidin", Blood, 106(12): 3979-3984 (2005).
Desmyter et al., "Antigen Specificity and High Affinity Binding Provided by One Single Loop of a Camel Single-domain Antibody," J. Biol. Chem., 276(28):26285-26290 (2001).
Devlin et al., "Random Peptide Libraries: A Source of Specific Protein Binding Molecules," Science, 249:404-406 (1990).
Donovan, et al., "The Iron Exporter Ferroportin/S1c401a1 is Essential for Iron Homeostasis," Cell Metabolism 1:191-200 (2005).
Donovan, et al., "Positional Cloning of Zebafish Fen-oportinl Identifies a Conserved Vertebrate Iron Exporter," Nature 403:776-781 (2000).
Dörner et al., "The Synthesis of Peptidomimetic Combinatorial Libraries Through Successive Amide Alkylations," Bioorganic Medicinal Chem., 4(5):709-715 (1996).
Du Pasquier, L., "Evolution of the Immune System", Ch. 7, Fundamental Immunology, (Paul, W., ed., 2nd ed. Raven Press, N.Y. (1989)).
Edge et al., "Deglycosylation of Glycoproteins by Trifluoromethanesulfonic Acid," Anal. Biochem., 118: 131-137 (1981).
Ewert et al., "Biophysical Properties of Camelid $V_{HH}$ Domains Compared to Those of Human $V_H3$ Domains," Biochemistry, 41:3628-3636 (2002).
Fasano et al., "Modifications of the iron—neuromelanin system in Parkinson's disease," J. Neurochem., 96:909-916 (2006).
Fermer et al., "Specificity Rescue and Affinity Maturation of a Low-Affinity IgM Antibody against Pro-Gastrin-Releasing Peptide using Phage Display and DNA Shuffling," Tumor Biol., 25(1-2):7-13 (2004).
Ferrara et al., "The Carbohydrate at FcγRIIIa Asn-162. An Element Required for High Affinity Binding to Non-fucosylated IgG Glycoforms," J. Biol. Chem., 281(8):5032-5036 (2006).
Fredericks et al., "Identification of potent human anti-IL-1R₁ antagonist antibodies," Protein Engineering, Design & Selection, 17(1):95-106 (2004).
Graham et al., "Characteristics of a Human Cell Line Transformed by DNA from Human Adenovirus Type 5," J. Gen. Virol., 36: 59-72 (1977).
Gruber et al., "Efficient Tumor Cell Lysis Mediated by a BispecificSsingle Chain Antibody Expressed in Escherichia coli," J. Immunology, 152: 5368-5374 (1994).
Guggenbuhl et al., "Bone mineral density in men with genetic hemochromatosis and HFE gene mutation," Osteoporos. Int., 16:1809-1814 (2005).
Guss et al., "Structure of the IgG-binding regions of streptococcal protein G," EMBO J., 5(7):1567-1575, (1986).
Ham et al., "Media and Growth Requirements," Meth. Enzymol., 58: 44-93 (1979).
Harlow et al., A Laboratory Manual, Cold Spring Harbor Laboratory, p. 76 (1988).
Hawkins, et al., "Selection of Phage Antibodies by Binding Affinity Mimicking Affinity Maturation," J. of Mol. Biol., 226:889-896 (1992).
Heiskanen, et al., "Phage-Displayed Peptides Mimicking the Discontinuous Neutralization Sites of Puumala Hantavirus Envelope Glycoproteins," Virology, 262: 321-332 (1999).
Heng et al., "Making cell-permeable antibodies (Transbody) through fusion of protein transduction domains (PTD) with single chain variable fragment (scFv) antibodies: Potential advantages over antibodies expressed within the intracellular environment (Intrabody)," Medical Hypotheses, 64:1105-1108 (2005).
Hey, "Artificial, non-antibody binding proteins for pharmaceutical and industrial applications," Trends in Biotechnol., 23(10):514-522 (2005).

Holliger et al., "'Diabodies': small bivalent and bispecific antibody fragments," Proc. Natl. Acad. Sci. USA, 90:6444-6448 (1993).
Hoogenboom et al., "By-passing Immunisation: Human Antibodies from Synthetic Repertoires of Germline $V_H$ Gene Segments Rearranged in Vitro," J. Mol. Biol., 227:381388 (1992).
Hruby et al., "Synthesis of oligopeptide and peptidomimetic libraries," Curr Opin. Chem. Biol., 1(1):114-119 (1997).
Huls et al., "Tumor cell killing by in vitro affinity-matured recombinant human monoclonal antibodies," Cancer Immunol. Immunother., 50:163-171 (2001).
Huston et al., "Protein engineering of antibody binding sites: Recovery of specific activity in an anti-digoxin single-chain Fv analogue produced in Escherichia coli," Proc. Natl. Acad. Sci. USA, 85:5879-5883 (1988).
Jakobovits et al., "Analysis of homozygous mutant chimeric mice: Deletion of the immunoglobulin heavy-chain joining region blocks B-cell development and antibody production," Proc. Natl. Acad. Sci. USA, 90:2551-2555 (1993).
Jakobovits et al., "Germ-line transmission and expression of a human-derived yeast artificial chromosome," Nature, 362:255-258 (1993).
Janeway, Charles, "Immunobiology: the immune system in health and disease", 3$^{rd}$ed., New York, Garland Pub., pp. 732 (1997).
Jermutus et al., "Tailoring in vitro evolution for protein affinity or stability," Proc. Natl. Acad. Sci. USA, 98(1):75-80 (2001).
Jespers et al., "Guiding the Selection of Human Antibodies from Phage Display Repertoires to a Single Epitope of an Antigen," Bio/Technology, 12:899-903 (1994).
Jones et al., "Replacing the complementarity-determining regions in a human antibody with those from a mouse," Nature, 321:522-525 (1986).
Kabat, et al., "Tabulation and Analysis of Amino Acid and Nucleic Acid Sequences of Precursor . . . ", Sequences of Protein of Immunological Interest, TOC 1991.
Kalinowski et al., "The evolution of iron chelators for the treatment of iron overload disease and cancer", Pharmacol. Rev., 57(4):547-583 (2005).
Kaur et al., "Does cellular iron dysregulation play a causative role in Parkinson's disease?" Ageing Res. Rev., 3:327-343 (2004).
Kettleborough et al., Humanization of a mouse monoclonal antibody by CDR-grafting: the importance of framework residues on loop conformation, Protein Enineering, 4(7):773-783 (1991).
Kipriyanov et al., "Single-chain antibody streptavidin fusions: Tetrameric bifunctional scFv-complexes with biotin binding activity and enhanced affinity to antigen," Hum. Antibodies Hybridomas, 6(3): 93-101 (1995).
Knutson, et al., "Iron loading and erythrophagocytosis increase ferroportin 1 (FPN1) expression in J774 macrophages", Blood, 102(12): 4191-4197 (2003).
Knutson, et al., "Iron release from macrophages after erythrophagocytosis is up-regulated by ferroportin 1 overexpression and down-regulated by hepcidin", ProcNatlAcadSciUSA 102 (5): 1324-1328 (2005).
Kostelny et al., "Formation of a Bispecific Antibody by the Use of Leucine Zippers," J. Immunol., 148(5):1547-1553 (1992).
Kreeger, "Immunocological Applications: Top List of Peptide Synthesis Services," The Scientist, 10(13):18-19 (1996).
Kulaksiz et al., "The iron-regulatory peptide hormone hepcidin: expression and cellular localization in the mammalian kidney", J. Endocrinol., 184:361-370 (2005).
Lindmark et al., "Binding of Immunoglobulins to Protein A and Immunoglobulin Levels in Mammalian Sera," J. Immunol. Meth., 62: 1-13 (1983).
Low et al., "Mimicking Somatic Hypermutation: Affinity Maturation of Antibodies Displayed on Bacteriophage Using a Bacterial Mutator Strain," J. Mol. Biol., 260:359-368, 1996.).
Lowman, "Bacteriophage Display and Discovery of Peptide Leads for Drug Development," Annu. Rev. Biophys. Biomol. Struct. 26: 401-424 (1997).
Mallender and Voss, "Construction, Expression, and Activity of a Bivalent Bispecific Single-chain Antibody," J. Biol. Chem., 269:199-206 (1994).

(56) References Cited

OTHER PUBLICATIONS

Marks et al., "By-passing Immunization: Human Antibodies from V-gene Libraries Displayed on Phage," *J. Mol. Biol.*, 222:581-597 (1991).
Mather, et al., "Culture of Testicular Cells and Hormone-Supplemented Serum-Free Medium," Annals of the New York Academy of Sciences, 383:44-68, (1982).
Mather, "Establishment and Characterization of Two Distinct Mouse Testicular Epithelial Cell Lines," *Biol. Reprod.*, 23: 243-252 (1980).
McKie, et al., "A novel duodenal iron-regulated transporter, IREG1, implicated in the basolateral transfer of iron to the circulation" *Molecular Cell*, 5(2):299-309 (2000).
The Merck Manual of Diagnosis and Therapy, 17th ed., Beers and Berkow (eds.), Merck Research Laboratories, Whitehouse Station, NJ pp. 1143-1147 (1999).
Mhashilkar et al., "Inhibition of HIV-1 Tat-mediated LTR transactivation and HIV-1 infection by anti-Tat single chain intrabodies," *EMBO J.* 14(7):1542-1551 (1995).
Morrison and Oi, "Genetically Engineered Antibody Molecules," *Adv. Immunol.*, 44:6592 (1989).
Morrison et al., "Chimeric human antibody molecules: Mouse antigen binding domains with human constant region domains," *Proc. Natl. Acad. Sci. USA*, 81:6851-6855 (1984).
Myers, "Will combinatorial chemistry deliver real medicines?" *Curr. Opin. Biotechnol.*, 8:701-707 (1997).
Nemeth et al., "Hepcidin Regulates Cellular Iron Efflux by Binding to Ferroportin and Inducing Its Internalization," *Science*, 306:2090-2093, (2004).
Nemeth et al., "The N-terminus of hepcidin is essential for its interaction with ferroportin: structure-function study," *Blood*, 107(1):328-333 (2006).
Nemeth, et al., "Ferroportin Residue C326 for its Interaction with Hepcidin," BioIron 2007, Program Book & Abstracts, The Second Congress of the International BioIron Society, Apr. 1-6, 2007, Kyoto, Japan, *Intl. BioIron Society*, PL-10, p. 28, (2007).
Neri et al., "High-affinity Antigen Binding by Chelating Recombinant Antibodies (CRAbs)," *J Mol Biol.*, 246:367-373 (1995).
Nishimiya et al., "Thermodynamic Consequences of Grafting Enhanced Affinity toward the Mutated Antigen onto an Antibody: The Case of Anti-lysozyme Antibody, HyHEL-10," *J Biol. Chem.*, 275(17):12813-12820 (2000).
Oates, et al., "Augmented internalization of ferroportin to late endosomes impairs iron uptake by enterocyte-like IEC-6 cells," Pflugers Archiv.,*Eur J of Physiol*, 450(5): 317-325 (2005).
Olafsen et al., "Characterization of engineered anti-p185$^{HER-2}$ (scFv-$C_H3)_2$ antibody fragments (minibodies) for tumor targeting," *Protein Eng. Des. Sel.*, 17(4):315-323 (2004).
Ouwehand et al., "Novel Diagnostic and Therapeutic Strategies with Genetically Engineered Human Antibodies," *Vox Sanguinis*, 74(Suppl 2):223-232 (1998).
Padlan, "A possible procedure for reducing the immunogenicity of antibody variable domains while preserving their ligand-binding properties," *Molecular Immunol.*, 28(4/5):489-498 (1991).
Padlan, "Anatomy of the Antibody Molecule," *Molecular Immunol.*, 31(3):169-217 (1994).
Papanikolaou et al., "Hepcidin in iron overload disorders," *Blood*, 105(10):4103-4105 (2005).
Paul, William E. (1993), "Fv structure and diversity in three dimensions", Fundamental Immunology, 3rd ed., pp. 242.
Portolano et al., "Lack of promiscuity in autoantigen-specific H and L chain combinations as revealed by human H and L chain 'roulette'", J. Immunol., 150(3):880-887 (1993).
Powers et al., "Expression of single-chain Fv-Fc fusions in *Pichia pastoris*," *Journal of Immunological Methods*, 251:123-135 (2001).
Rader et al., "A phage display approach for rapid antibody humanization: Designed combinatorial V gene libraries," *Proc. Natl. Acad. Sci. USA*, 95:8910-8915 (1998).

Rajpal et al., "A general method for greatly improving the affinity of antibodies by using combinatorial libraries," *Proc. Natl. Acad. Sci. USA*, 102(24):8466-8471 (2005).
Riechmann, et al., "Reshaping human antibodies for therapy," Nature, 332:323-327, (1988).
Riechmann, et al., "Single domain antibodies: comparison of camel VH and camelised human VH domains," *J. Immunol. Methods*, 231:25-38 (1999).
Roberts and Szostak, "RNA-peptide fusions for the in vitro selection of peptides and proteins," *Proc. Natl. Acad. Sci. USA*, 94: 12297-12302 (1997).
Roth and Craig, "VDJ Recombination: A Transposase Goes to Work," *Cell*, 94:411-414 (1998).
Rothman et al., "Antibody-Dependent Cytotoxicity Mediated by Natural Killer Cells is Enhanced by Castanospermine-Induced Alterations of IgG Glycosylation," *Mol. Immunol.*, 26(12):1113-1123 (1989).
Rudikoff et al, "Single amino acid substitution altering antigen-binding specificity", PNAS, 79(6):1979-1983 (1982).
Sanger et al., "DNA Sequencing with Chain-Terminating Inhibitors," *Proc. Nati. Acad. Sci. USA*, 74(12): 5463-5467 (1977).
Schoonjans et al., "Fab Chains As an Efficient Heterodimerization Scaffold for the Production of Recombinant Bispecific and Trispecific Antibody Derivatives," *J Immunol.* 165:7050-7057 (2000).
Scott and Smith, "Searching for Peptide Ligands with an Epitope Library," *Science*, 249: 386-390 (1990).
Shalaby et al., "Development of Humanized Bispecific Antibodies Reactive with Cytotoxic Lymphocytes and Tumor Cells Overexpressing the HER2 Protooncogene," *J. Exp. Med.*, 175:217-225 (1992).
Shields et al., "High Resolution Mapping of the Binding Site on Human IgG1 for FcγRI, FcγRII, FcγRIII, and FcRn and Design of IgG1 Variants with Improved Binding to the FcγR," *J. Biol. Chem.*, 276(9):6591-6604 (2001).
Shields et al., "Lack of Fucose on Human IgG1 N-Linked Oligosaccharide Improves Binding to Human FcγRIII and Antibody-dependent Cellular Toxicity," *J. Biol. Chem.*, 277(30):26733-26740 (2002).
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *J Biol Chem.*, 278(5):34663473 (2003).
Shopes, "A genetically engineered human IgG mutant with enhanced cytolytic activity," *J. Immunol.*, 148(9): 2918-2922 (1992).
Skerra et al., "Assembly of a Functional Immunoglobulin Fv Fragment in *Escherichia coli*," Science, 240: 1038-1041 (1988).
Sojar et al., "A Chemical Method for the Deglycosylation of Proteins," *Arch. Biochem. Biophys.*, 259(1): 52-57 (1987).
Stevenson et al., "A chimeric antibody with dual Fc regions (bisFabFc) prepared by manipulations at the IgG hinge," *Anti-Cancer Drug Design*, 3: 219-230 (1989).
Stoian et al., "New alternatives for erythropoietin therapy in chronic renal failure", Central EP J. Med., 2(4):361-378 (2007).
Studnicka et al., Human-engineered monoclonal antibodies retain full specific binding activity by preserving non-CDR complementarity-modulating residues, Protein Engineering, 7(6): 805-814 (1994).
Takasaki et al., "Structure-based design and characterization of exocyclic peptidomimetics that inhibit TNFα binding to its receptor," *Nature Biotech.*, 15:1266-1270 (1997).
Thomas et al., "IEC-6 Cells are an appropriate model of intestinal iron absorption in rats", *J Nutrition*, 132(4):680-687 (2002).
Thomas and Oates, "Ferroportin/IREG-1/MTP-1/SLC40A1 Modulates the uptake of iron at the apical membrane of enterocytes", *Gut* 53: 44-49 (2004).
Thotakura et al., "Enzymatic deglycosylation of glycoproteins," *Meth. Enzymol.*, 138: 350-359 (1987).
Tutt et al., "Trispecific F(ab')3 derivatives that use cooperative signaling via the TCR/CD3 complex and CD2 to activate and redirect resting cytotoxic T cells," *J. Immunol.*, 147:60-69 (1991).

(56) References Cited

OTHER PUBLICATIONS

Umaña et al., "Engineered glycoforms of an antineuroblastoma IgG1 with optimized antibody-dependent cellular cytotoxic activity," *Nature Biotechnol.* 17(2):176-180 (1999).

Urlaub, and Chasin, "Isolation of Chinese hamster cell mutants deficient in dihydrofolate reductase activity," *Proc. Natl. Acad. Sci. USA*, 77(7):4216-4220 (1980).

Van Den Beucken, et al., "Affinity maturation of Fab antibody fragments by fluorescent-activated cell sorting of yeast-displayed libraries," *FEBSLett*, 546: 288-294, (2003).

Verhoeyen et al., "Reshaping Human Antibodies: Grafting an Antilysozyme Activity," *Science*, 239:1534-1536 (1988).

Ward et al., "Binding activities of a repertoire of single immunoglobulin variable domains secreted from *Escherichia coli*," *Nature*, 341:544-546 (1989).

Watkins, "Screening of Phage-Expressed Antibody Libraries by Capture Lift," *Methods in Molecular Biology, Antibody Phage Display: Methods and Protocols*, vol. 178, Eds. O'Brien and Aitken, (Humana Press, Totawa, NJ (2001)) pp. 187-193.

Wells and Lowman, "Rapid evolution of peptide and protein binding properties in vitro," *Curr. Opin. Biotechnol.*, 3: 355-362 (1992).

Wheeler et al., "Intrabody-based strategies for inhibition of vascular endothelial growth factor receptor-2: effects on apoptosis, cell growth, and angiogenesis," *FASEB J.*., 17:1733-1735, (2003).

Willems et al., "Optimizing expression and purification from cell culture medium of trispecific recombinant antibody derivatives," *J. Chromatogr. B. Analyt. Technol. Biomed. Life Sci.*, 786:161-176, (2003).

Williams and Polli, "The Lyophilization of Pharmaceuticals: A Literature Review," *Journal of Parenteral Science and Technology*, 38: 48-59 (1984).

Winter et al., "Making Antibodies by Phage Display Technology," *Annu. Rev. Immunol.*, 12:433-455, (1994).

Wolff et al., "Monoclonal Antibody Homodimers: Enhanced Antitumor Activity in Nude Mice," *Cancer Research*, 53: 2560-2565 (1993).

Yamane-Ohnuki et al., "Establishment of FUT8 Knockout Chinese Hamster Ovary Cells: An Ideal Host Cell Line for Producing Completely Defucosylated Antibodies with Enhanced Antibody-Dependent Cellular Cytotoxicity," *Biotechnol, Bioeng.*, 87(5):614-622 (2004).

Yang, et al., "Regulation of Reticuloendothelial Iron Transporter MTP1 (Slc11a3) by inflammation," J of Biol Chem 277(42): 39786-39791 (2002).

Zaccolo et al., "The Effect of High-Frequency Random Mutagenesis on in Vitro Protein Evolution: A Study on TEM-1 β-Lactamase," *J. Mol. Biol.*, 285:775-783 (1999).

Zapata et al., "Engineering linear F(ab')$_2$ fragments for efficient production in *Escherichia coli* and enhanced antiproliferative activity," *Protein Eng.*, 8(10):1057-1062 (1995).

Zola, "Using Monoclonal Antibodies: Soluble Antigens," Ch. 6, Monoclonal Antibodies: *A Manual of Techniques*, (CRC Press, Inc., Boca Raton, FL, (1987)), pp. 147-158.

\* cited by examiner

Figure 6

Antibody Heavy Chain CDRs

| | CDR1 | CDR2 | CDR3 |
|---|---|---|---|
| 37C8 | GYYMH | WINPHTGGKNYAQKFQG | DPSIAVAGPSFYYGLDV |
| 37G8 | GYYMH | WINPHTGGKNYAQKFQG | DPSLVVTGPSFYYYGLDV |
| 38C8 | GYYMH | WINPHTGGKNYGQKFQG | DPSISVAGPSFYYFGLDV |
| 37B9 | GYYMH | WINPHTGGKNYAQRFQG | DPSLVVTGPSFYYYGLDV |
| 38E3 | GYYMH | WINPHTGGKNYAQKFQG | DPSLSVTGPSFYYYGLDV |
| 38D2 | GYYLH | WINPFTGATDYAQKFQG | DPSL--Q-NSYHVYVMDV |
| 38A4 | SFAMT | AIGGSGRNTYYADSVKG | EGAMA-R-PP-R---GLDV |
| 38G6 | SYSVN | YISGSSSTVHYADSVKG | WGTRQ--G-H--YFGMDV |
| 37A2 | GYGMH | VIWPDGTNKYYADSVKG | GG---ATA-VF---GMNV |

Figure 7

Antibody Light Chain CDRs

| | CDR1 | CDR2 | CDR3 |
|---|---|---|---|
| 37C8 | RSSQSLVYSDGNTYLS | KISNRFS | MQATQFPWT |
| 37G8 | RSSQSLVHSDGNTYLS | KISNRLS | MQATQFPWT |
| 38C8 | RSSQSLVHSDGNTYLS | KISNRFS | MQATQFPWT |
| 37B9 | RSSQSLVHSDGNTYLS | KISNRFS | MQATQFPWT |
| 38E3 | RSSQSLVHSDGNTYLS | KISNRFS | MQATQFPWT |
| 38D2 | RSSQSLVHSDGNTYLS | KISNRFS | MQATQFPWT |
| 38A4 | KSSQSILYSSNNKNYLA | GASTRES | QQYYFTPFS |
| 38G6 | TLSSGYNNYKVD | VGTGGIVGSKGD | GADHASGNNFVYV |
| 37A2 | SGDELPKQYAY | KDSERPS | QSPDSRRTVI |

38G6 VL:
cagcctgtgctgactcagccaccttctgcatcagcctccctgggagcctcggtcacactcacctgcaccctgagcagcggctacaata
attataaagtggactggttccagcagcgaccaggagaggcccccgtttgtgatgcgagtgggcactggtgggattgtgggatccaa
ggggatggcatccctgatcgctctcagtcttggctcaggcctgaatcggtacctgaccatcaagaacatccaggaagaggatgag
agtgactaccactgtggggcagaccatgccagtgggaacaacttcgtgtatgtcttcggaactgggaccaaggtcaccgtccta
(SEQ ID NO: 105)

QPVLTQPPSASASLGASVTLTCTLSSGYNNYKVDWFQQRPGRGPRFVMRVGTGGIV
GSKGDGIPDRFSVLGSGLNRYLTIKNIQEEDESDYHCGADHASGNNFVYVFGTGTKV
TVL (SEQ ID NO: 106)

38G6 VH:
gaagtgcaggtggtggagtctggggggaggcttggtacagcctggggggtccctgagactctcctgtgcagcctctggattcacctca
gtagctatagcgtgaactgggtccgccaggctccaggaaaggggctggagtgggtctcatacattagtggtagtagtagtaccgtaca
ctacgcagactctgtgaagggccgattcaccatttccagagacactgccaagaattcagtgtatctgcaactgaacagcctgagagac
gaggacacggctctgtattactgtgcgagatgggaactcgtcaggccactacttcggtatggacgtctggggccaagggaccacg
gtcaccgtctctag (SEQ ID NO: 107)

EVQVVESGGGLVQPGGSLRLSCAASGFTFSSYSVNWVRQAPGKGLEWVSYISGSSST
VHYADSVKGRFTISRDTAKNSVYLQLNSLRDEDTALYYCARWGTRQGHYFGMDVW
GQGTTVTVSS (SEQ ID NO: 108)

38E3 VK:
Gatgttgtgatgacccagactccactctcctcacctgtcaccctggcagccggcctccatctcctgcaggtctagtcaaagcctcgta
cacagtgatggaaacacctacttgagttggcttcagcagaggccaggccagcctccaagactcctaatttataagattctaaccgattct
ctgggtctccagacagattcagtggcagtggggcagggacagatttcacactgaaaatcagcaggtggaagctgaggatgtcggg
gtttattactgcatgcaagctacacaattccgtggacgttcggccaagggaccaaggtggaaatcaaa (SEQ ID NO: 95)

DVVMTQTPLSSPVTLGQPASISCRSSQSLVHSDGNTYLSWLQQRPGQPPRLLIYKISN
RFSGVPDRFSGSGAGTDFTLKISRVEAEDVGVYYCMQATQFPWTFGQGTKVEIK
(SEQ ID NO: 96)

38E3 VH:
caggtgcagttggtgcaatctggggctgaggtgaagaagcctggggtcctcagtgaaggtctcctgcaaggcttctggatacaccctca
ccggctacatcatgcactgggtgcgacaggcccctggacaagggcttgagtggatgggatggatcaaccctcacactggtgcaaa
aactatgcccagaagtttcagggcagggtcaccctgaccaggacacgtccatcagcacagcctacatggagctgaacagcttgaga
tctgacgacacggccgtgtattactgtgcgagagatcctagtttatcagtgactgggccttccttctactactacggtttggacgtctggg
gccaagggaccacggtcaccgtctctagt (SEQ ID NO: 97)

QVQLVQSGAEVKKPGSSVKVSCKASGYTLTGYYMHWVRQAPGQGLEWMGWINPH
TGGKNYAQKFQGRVTLTRDTSISTAYMELNSLRSDDTAVYYCARDPSLSVTGPSFYY
YGLDVWGQGTTVTVSS (SEQ ID NO: 98)

Figure 8A

38D2 VK:
gatattgtgatgacccagactccattctcttcacctgtcaccctggacagccggcctccatctcctgcaggtctagtcaaagcctcgtac
acagtgatggaaacacctacttgagttggcttcagcagaggccaggccagcctccaagactcctaatttataagatttctaaccggttct
ctggggtcccagacagattcagtggcagtggggcaggacagatttcacactgaaaatcagcaggtggaagctgaggatgtcggg
gtttattctgcatgcaagctacacaattccttggacgttcggccaagggaccaaggtggaaatcaaa (SEQ ID NO: 85)

DIVMTQTPFSSPVTLGQPASISCRSSQSLVHSDGNTYLSWLQQRPGQPPRLLIYKISNR
FSGVPDRFSGSGAGTDFTLKISRVEAEDVGVYFCMQATQFPWTFGQGTKVEIK (SEQ
ID NO: 86)

38D2 VH:
caggtgcagttggtgcagtctggggctgaggtgaagaagcccggggcctcagtgaaggtctcctgcaaggcttctggatacaccctc
accggctactatctgcactgggtgcgacaggcccctggacaagagcttgagtggatgggatggatcaaccttcactggtgccacag
actatgcacagaagtttcagggcagggtcaccatgaccccgggacacgtccatcaatacagcccacatggagctgagcaggctgaga
tctgacgacacggccgtgtattactgtgcgagagacccctctctacaaaattcctaccattactacgtcatggacgtttggggccaaggg
accacggtcaccgtctctagt (SEQ ID NO: 87)

QVQLVQSGAEVKKPGASVKVSCKASGYTLTGYYLHWVRQAPGQELEWMGWINPFT
GATDYAQKFQGRVTMTRDTSINTAHMELSRLRSDDTAVYYCARDPSLQNSYHYYV
MDVWGQGTTVTVSS (SEQ ID NO: 88)

38C8 VK:
gatattgtgatgacccagactccactctcctcacctgtcaccctggtcagccggcctccatctcctgcaggtctagtcaaagcctcgtac
acagtgatggaaacacctacttgagttggcttcagcagaggccaggccagcctccaagactcctaatttatatagatttctaaccggttct
ctggggtcccagacagattcagtggcagtggggcaggacagatttcacactgaaaatcagcaggtggaagctgaggatgtcggg
gtttattactgcatgcaagctacacaattccgtggacgttcggccaagggaccaaggtggaaatcaaa (SEQ ID NO: 75)

DIVMTQTPLSSPVTLGQPASISCRSSQSLVHSDGNTYLSWLQQRPGQPPRLLIYKISNR
FSGVPDRFSGSGAGTDFTLKISRVEAEDVGVYYCMQATQFPWTFGQGTKVEIK (SEQ
ID NO: 76)

38C8 VH:
caggtgcagttggtgcaatctggggctgaggtgaagaagcctggggcctcagtgaaggtctcctgcaaggcttctggatacaccctca
ccggctactacatgcactgggtgcgacaggcccctggacaaggggcttgagtggatgggatggatcaaccctcacactggtggcaaa
aactatggacagaagttcagggcagggtcaccctgaccaggacacgtccatcaacacagcctacatggagctgacagcttgaga
tctgacgacacggccgtgtattactgtgcgagagatcctagtatatcagtggctggcccttcctctactacttcggtttggacgtctggg
gccaagggaccacggtcaccgtctctagt (SEQ ID NO: 77)

QVQLVQSGAEVKKPGSSVKVSCKASGYTLTGYYMHWVRQAPGQGLEWMGWINPH
TGGKNYGQKFQGRVTLTRDTSINTAYMELNSLRSDDTAVYYCARDPSISVAGPSFYY
FGLDVWGQGTTVTVSS (SEQ ID NO: 78)

Figure 8B

38A4 VK:
gacatcgtgatgacccagtctccagactccctggctgtgtctctgggcgagagggccaccatcaactgcaagtccagccagagtatttt
atacagctccaacaataagaactacttagcttggtaccagcagaaaccaggacagcctcctaagttgctcatttacggggcatctaccc
gggaatccggggtccctgaccgattcagtggcagcgggtctgggacagatttcactctcaccatcagtagcctgcaggctgaagatgt
ggcagtttattactgtcagcaatactattactccattctcttcggccctgggaccaaagtggatatcgaa (SEQ ID NO: 65)

DIVMTQSPDSLAVSLGERATINCKSSQSILYSSNNKNYLAWYQQKLGQPPKLLIYGAS
TRESGVPDRFSGSGSGTDFTLTISSLQAEDVAVYYCQQYYFTPFSFGPGTKVDIE (SEQ
ID NO: 66)

38A4 VH:
gaggtgcagctgttggagtctgggggaggcctggtacagcctggggggtctctgagactctcctgtgcagcctctggattcactttag
cagcttttgccatgacctgggtccgccaggctccagggaagggctggagtggtctcagctattggtggtagtggtaggaacacata
ctacgcagactccgtgaaggccggttcaccatctccagagacaattccaagaacacgctgtacctgcaaatgagcagcctgagag
cgaggacacggccgtatattactgtgcgaaagaggggctatggctcggcctcgagggggttggacgtctggggccaagggacca
cggtcaccgtctctagt (SEQ ID NO: 67)

EVQLLESGGGLVQPGGSLRLSCAASGFTFSSFAMTWVRQAPGKGLEWVSAIGGSGR
NTYYADSVKGRFTISRDNSKNTLYLQMSSLRAEDTAVYYCAKEGAMARPPRGLDV
WGQGTTVTVSS (SEQ ID NO: 68)

37G8 VK:
gatattgtgatgacccagactccactctcctcacctgtcacccatggtcagccggcctccatctcctgcaggtctagtcaaagcctcgta
cacagtgatggaaacacctacttgagttggcttcagcagaggccaggccagcctccaagactcctaatttataagattctaaccggttg
tctggggtcccagacagattcagtggcagtgggacaggacagatttcacactgaaaatcagcagggtggaagctgaggatgtcgg
ggtttatgtctgcatgcaagctacacaattccgtggacgtcggccaagggaccaaggtggaaatcaaa (SEQ ID NO: 55)

DIVMTQTPLSSPVTHGQPASISCRSSQSLVHSDGNTYLSWLQQRPGQPPRLLIYKISNR
LSGVPDRFSGSGTGTDFTLKISRVEAEDVGVYVCMQATQFPWTFGQGTKVEIK (SEQ
ID NO: 56)

37G8 VH:
caggtgcagttggtgcaatctggggctgaggtgaagaagcctgggtcctcagtgaaggtctctgcaaggcttctggatacaccctca
ccggctactacatgcactgggtgcgccaggcccctggacaaggcttgagtggatgggatggatcaaccctcacactggtggcaaa
aactatgcccagaagtttcagggcagggtcaccctgaccaggacacgtccatcaacacggcctacatggagctgaacaccttgaga
tctgacgacacggccgtgtattactgtgcgcagatccctagtctagtagtgactggggcttcctctactactacggttggacgtctggg
gccaagggaccacggtcaccgtctctagt (SEQ ID NO: 57)

QVQLVQSGAEVKKPGSSVKVSCKASGYTLTGYYMHWVRQAPGQGLEWMGWINPH
TGGKNYAQKFQGRVTLTRDTSINTAYMELNTLRSDDTAVYYCARDPSLVVTGPSFY
YYGLDVWGQGTTVTVSS (SEQ ID NO: 58)

Figure 8C

37C8 VK:
gatattgtgatgacccagactccactctcctcacctgtcaccctggtcagccggcctccatctcctgcaggtctagtcaaagcctcgtat
acagtgatggaaacacctacttgagttggcttcagcagaggccaggccagcctccaagactcctagtttataagatttctaaccggttct
ctggggtcccagacagattcagtggcagtggggcaggcacagattttcacattgaaaatcagcagggtggaagctgaggatgtcggg
gtttattactgcatgcaagctacacaattccgtggacgttcggccaagggaccaaggtggaaatcaaa (SEQ ID NO: 45)

DIVMTQTPLSSPVTLGQPASISCRSSQSLVYSDGNTYLSWLQQRPGQPPRLLVYKISN
RFSGVPDRFSGSGAGTDFTLKISRVEAEDVGVYYCMQATQFPWTFGQGTKVEIK
(SEQ ID NO: 46)

37C8 VH:
caggtgcagttggtgcaatctggggctgaggtgaagaagcctgggtcctcagtgaaggtctcctgtaaggcttctggatacaccctca
ccggctactacatgcactgggtgcgacaggcccctggacaagggcttgagtggatgggatggatcaaccctcacactggtggcaaa
aactatgcacagaagttcagggcagggtcaccctgaccaggagacacgtccatcaacacagcctacatggagctgaacaccttgaga
tctgacgacacggccgtgtattactgtgcgagagatccagtatagcagtggctggccttcctctactactacggtttggacgtctggg
gccaagggaccacggtcaccgtctctagt (SEQ ID NO: 47)

QVQLVQSGAEVKKPGSSVKVSCKASGYTLTGYYMHWVRQAPGQGLEWMGWINPH
TGGKNYAQKFQGRVTLTRDTSINTAYMELNTLRSDDTAVYYCARDPSIAVAGPSFY
YYGLDVWGQGTTVTVSS (SEQ ID NO: 48)

37B9 VK:
gatattgtgatgacccagactccactctcctcacctgtcaccctggtcagccggcctccatctcctgcaggtctagtcaaagcctcgtac
acagtgatggaaacacctacttgagttggcttcagcagaggccaggccagcctccaagactcctaattataagatttctaaccggttct
ctggggtcccagacagattcagtggcagtgggacaggcacagattcacactgaaaatcagcagggtggaagctgaggatgtcggg
gttattctgcatgcaagctacacaattccgtggacgttcggccaagggaccaaggtggaaatcaaa (SEQ ID NO: 35)

DIVMTQTPLSSPVTLGQPASISCRSSQSLVHSDGNTYLSWLQQRPGQPPRLLIYKISNR
FSGVPDRFSGSGTGTDFTLKISRVEAEDVGVYFCMQATQFPWTFGQGTKVEIK (SEQ
ID NO: 36)

37B9 VH:
caggtgcagttggtgcaatctggggctgaggtgaagaagcctgggtcctcagtgaaggtctcctgcaaggcttctggatacaccctca
ccggctactacatgcactgggtgcgacaggcccctggacaagggcttgagtggatgggatggatcaaccctcacactggtggcaaa
aactatgcacagaggttcagggcagggtcaccctgaccagggacacgtccgtcaacacggcctacatggagctgaacaccttgag
atctgacgacacggccgttattactgtgcgagagatccagtctagtagtgactggccttcctctactactacggtttggacgtctggg
gccaagggaccacggtcaccgtctctagt (SEQ ID NO: 37)

QVQLVQSGAEVKKPGSSVKVSCKASGYTLTGYYMHWVRQAPGQGLEWMGWINPH
TGGKNYAQRFQGRVTLTRDTSVNTAYMELNTLRSDDTAVYYCARDPSLVVTGPSFY
YYGLDVWGQGTTVTVSS (SEQ ID NO: 38)

Figure 8D

37A2 VL:
tcctatgagtigacacagccaccctcggtgtcagtgtcccctggacagacggccaggatcacctgctctggagatgaattgccaaagc
aatatgcttattggtaccagcagaaggcaggccaggcccctgtaatggtgattcataaagacagtgagaggccctcaggggatccctga
gcgattctctggctccagcgcagggacaattgtcacgttgaccatcagtggagtccaggcagaagacgaggctgactattactgtcaat
caccagacagcagacgtactgtgatattcggcggagggaccaagctgaccgtccta (SEQ ID NO: 25)

SYELTQPPSVSVSPGQTARITCSGDELPKQYAYWYQQKAGQAPVMVIHKDSERPSGI
PERFSGSSAGTIVTLTISGVQAEDEADYYCQSPDSRRTVIFGGGTKLTVL (SEQ ID
NO: 26)

37A2 VH:
caggtgcagctggtggagtctgggggaggcgtggtccagcctggagggtccctgagactctcctgtgcagcgtctggattcaccttca
gtggctatggcatgcactgggtccgccaggctccaggcaggggctggagtgggtggcagttatatggcctgatggaactaataaat
actatgcagactccgtgaagggccgattcaccatctccagagacaattccaagaacaaactgtatctgcaaatgaacagcctgagagc
cgaggacacggctgtgtattactgtgcgagagggggagcaacagcagttttcggtatgaacgtctggggccaagggaccacggtca
ccgtctctagt (SEQ ID NO: 27)

QVQLVESGGGVVQPGRSLRLSCAASGFTFSGYGMHWVRQAPGRGLEWVAVIWPDG
TNKYYADSVKGRFTISRDNSKNKLYLQMNSLRAEDTAVYYCARGGATAVFGMNV
WGQGTTVTVSS (SEQ ID NO: 28)

Human fpn sequence          38G6              38A4                    31A5 m- hfpn (functional)

PGSPLDLSVSPFEDIRSRFIQGESITPTKIPRITTEIYMSNGSNSANIV*PETSPESVPIISVS*
PGSPLDLSVSPFEDIRSRFIQGESITPTKIPRITNEIYMSNGSNSANIVPETSPESVPIISVS
PGSPLDLSVSPFEDIRSRFIQGESITPTKIPRITTEIYMSNGSNSANIVPETSPESVPIISVS
PGSPLDLSVSPFEDIRSRFIQGESIPPTIPETTTEIYMSNGSMSANIVPETSPESVPIISVS
PGSPLDLSVSPFEDIRSRFIQGESITPTKIPETTTEIYMSNGSNSANIVPETSPESVPIISVS
PGSPLDLSVSPFEDIRSRFIQGESITPTKIPETTTEIYMSNGSMSANIVPETSPESVPIISVS
                                                                   48B9 mouse- hfpn (non-functional)
                              37A2

Mouse fpn sequence

PGSPLDLSVSPFEDIRSRFVNVEPVSPTTK *TTEMHMS*MSNVHEMSTKPIPIVSVS
                                          ↑
                                 1C7 and 4E10 rat- mfpn (non-functional)

Box = maximal epitope
Italics = minimal epitope

SEQUENCE LISTING

<160> NUMBER OF SEQ ID NOS: 137

<210> SEQ ID NO 1
<211> LENGTH: 337
<212> TYPE: DNA
<213> ORGANISM: Mus musculus

<400> SEQUENCE: 1
agatgttgtg ctgacccaga ctccactcac tttgtcggct accattggac aaccagcctc      60
catctcttgt aagtcaagtc agagcctctt acatagtgat ggaatgacat atttgaattg     120

```
gttgttacag aggccaggcc agtctccaaa gcgcctgatc tatctggtgt ctaaactgga      180
ctctggagtc cctgacaggt tcactggcag tggatcaggg acagatttca cactgaaaat      240
cagcagaata gaggctgaag atttgggagt ttattattgc tggcaaggta cacattttcc      300
tcggacgttc ggtggaggca ccaagctgga aatcaaa                               337
```

```
<210> SEQ ID NO 2
<211> LENGTH: 112
<212> TYPE: PRT
<213> ORGANISM: Mus musculus

<400> SEQUENCE: 2
```

Asp Val Val Leu Thr Gln Thr Pro Leu Thr Leu Ser Ala Thr Ile Gly
1               5                   10                  15

Gln Pro Ala Ser Ile Ser Cys Lys Ser Ser Gln Ser Leu Leu His Ser
            20                  25                  30

Asp Gly Met Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Ile Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

```
<210> SEQ ID NO 3
<211> LENGTH: 336
<212> TYPE: DNA
<213> ORGANISM: Mus musculus

<400> SEQUENCE: 3
caggttcagc tgcagcagtc tggagctgag ctggcgaggc ctggggcctc agtgaagctg       60
tcctgcaagg cttctggcta caccttcaca agctatggta tatcctgggt gaaacagaga      120
actggacagg gccttgagtg gattggagag atttatccta gaagtggtaa tgcttactac      180
aatgagaagt tcaaggtcaa ggccacactg actatagaca atcctccag cacagcgtac       240 atggaactcc gcagcctgac atctgaggat tctgcggtct atttctgtgg tggtaactac      300
tactggggcc aaggcaccac tctcacagtc tcctca                                336
```

```
<210> SEQ ID NO 4
<211> LENGTH: 112
<212> TYPE: PRT
<213> ORGANISM: Mus musculus

<400> SEQUENCE: 4
```

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Ala Tyr Tyr Asn Glu Lys Phe
    50                  55                  60

Lys Val Lys Ala Thr Leu Thr Ile Asp Lys Ser Ser Thr Ala Tyr
65                  70                  75                  80

```
Met Glu Leu Arg Ser Leu Thr Ser Glu Asp Ser Ala Val Tyr Phe Cys
            85                  90                  95

Gly Gly Asn Tyr Tyr Trp Gly Gln Gly Thr Thr Leu Thr Val Ser Ser
            100                 105                 110
```

<210> SEQ ID NO 5
<211> LENGTH: 16
<212> TYPE: PRT
<213> ORGANISM: Mus musculus

<400> SEQUENCE: 5

```
Lys Ser Ser Gln Ser Leu Leu His Ser Asp Gly Met Thr Tyr Leu Asn
1               5                   10                  15
```

<210> SEQ ID NO 6
<211> LENGTH: 7
<212> TYPE: PRT
<213> ORGANISM: Mus musculus

<400> SEQUENCE: 6

```
Leu Val Ser Lys Leu Asp Ser
1               5
```

<210> SEQ ID NO 7
<211> LENGTH: 9
<212> TYPE: PRT
<213> ORGANISM: Mus musculus

<400> SEQUENCE: 7

```
Trp Gln Gly Thr His Phe Pro Arg Thr
1               5
```

<210> SEQ ID NO 8
<211> LENGTH: 5
<212> TYPE: PRT
<213> ORGANISM: Mus musculus

<400> SEQUENCE: 8

```
Ser Tyr Gly Ile Ser
1               5
```

<210> SEQ ID NO 9
<211> LENGTH: 17
<212> TYPE: PRT
<213> ORGANISM: Mus musculus

<400> SEQUENCE: 9

```
Glu Ile Tyr Pro Arg Ser Gly Asn Ala Tyr Tyr Asn Glu Lys Phe Lys
1               5                   10                  15

Val
```

<210> SEQ ID NO 10
<211> LENGTH: 3
<212> TYPE: PRT
<213> ORGANISM: Mus musculus

<400> SEQUENCE: 10

```
Asn Tyr Tyr
1
```

<210> SEQ ID NO 11
<211> LENGTH: 717
<212> TYPE: DNA

<213> ORGANISM: Mus musculus

<400> SEQUENCE: 11

```
atgatgagtc ctgcccagtt cctgtttctg ttagtgctct ggattcggga aaccaacggt      60
gatgttgtgc tgacccagac tccactcact ttgtcggcta ccattggaca accagcctcc     120
atctcttgta agtcaagtca gagcctctta catagtgatg gaatgacata tttgaattgg     180
ttgttacaga ggccaggcca gtctccaaag cgcctgatct atctggtgtc taaactggac     240
tctggagtcc ctgacaggtt cactggcagt ggatcaggga cagatttcac actgaaaatc     300
agcagaatag aggctgaaga tttgggagtt tattattgct ggcaaggtac acattttcct     360
cggacgttcg gtggaggcac caagctggaa atcaaacggg ctgatgctgc accaactgta     420
tccatcttcc caccatccag tgagcagtta acatctggag gtgcctcagt cgtgtgcttc     480
ttgaacaact tctaccccaa agacatcaat gtcaagtgga gattgatgg cagtgaacga     540
caaaatggcg tcctgaacag ttggactgat caggacagca agacagcac ctacagcatg     600
agcagcaccc tcacgttgac caaggacgag tatgaacgac ataacagcta tcctgtgag     660
gccactcaca agacatcaac ttcacccatt gtcaagagct caacaggaa tgagtgt       717
```

<210> SEQ ID NO 12
<211> LENGTH: 239
<212> TYPE: PRT
<213> ORGANISM: Mus musculus

<400> SEQUENCE: 12

```
Met Met Ser Pro Ala Gln Phe Leu Phe Leu Leu Val Leu Trp Ile Arg
1               5                   10                  15

Glu Thr Asn Gly Asp Val Val Leu Thr Gln Thr Pro Leu Thr Leu Ser
            20                  25                  30

Ala Thr Ile Gly Gln Pro Ala Ser Ile Ser Cys Lys Ser Ser Gln Ser
        35                  40                  45

Leu Leu His Ser Asp Gly Met Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Ile Glu Ala Glu Asp Leu Gly Val Tyr Tyr
            100                 105                 110

Cys Trp Gln Gly Thr His Phe Pro Arg Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
```

<210> SEQ ID NO 13
<211> LENGTH: 1398
<212> TYPE: DNA
<213> ORGANISM: Mus musculus

<400> SEQUENCE: 13

| | | | | | |
|---|---|---|---|---|---|
| atggaatgga | tctggatcct | tctcttcatc | ctgtcaggaa | ctgcgggtgt | ccaatcccag | 60 |
| gttcagctgc | agcagtctgg | agctgagctg | gcgaggcctg | ggcctcagt | gaagctgtcc | 120 |
| tgcaaggctt | ctggctacac | cttcacaagc | tatggtatat | cctgggtgaa | acagagaact | 180 |
| ggacagggcc | ttgagtggat | tggagagatt | tatcctagaa | gtggtaatgc | ttactacaat | 240 |
| gagaagttca | aggtcaaggc | cacactgact | atagacaaat | cctccagcac | agcgtacatg | 300 |
| gaactccgca | gcctgacatc | tgaggattct | gcggtctatt | tctgtggtgg | taactactac | 360 |
| tggggccaag | gcaccactct | cacagtctcc | tcagccaaaa | caacagcccc | atcggtctat | 420 |
| ccactggccc | ctgtgtgtgg | aggtacaact | ggctcctcgg | tgactctagg | atgcctggtc | 480 |
| aagggttatt | tccctgagcc | agtgaccttg | acctggaact | ctggatccct | gtccagtggt | 540 |
| gtgcacacct | tcccagctct | cctgcagtct | ggcctctaca | ccctcagcag | ctcagtgact | 600 |
| gtaacctcga | acacctggcc | cagccagacc | atcacctgca | atgtggccca | cccggcaagc | 660 |
| agcaccaaag | tggacaagaa | aattgagccc | agagtgccca | taacacagaa | ccctgtcct | 720 |
| ccactcaaag | agtgtccccc | atgcgcagct | ccagacctct | ggggtggacc | atccgtcttc | 780 |
| atcttccctc | caaagatcaa | ggatgtactc | atgatctccc | tgagccccat | ggtcacatgt | 840 |
| gtggtggtgg | atgtgagcga | ggatgaccca | gacgtccaga | tcagctggtt | tgtgaacaac | 900 |
| gtggaagtac | acacagctca | gacacaaacc | catagagagg | attacaacag | tactctccgg | 960 |
| gtggtcagtg | ccctccccat | ccagcaccag | gactggatga | gtggcaagga | gttcaaatgc | 1020 |
| aaggtcaaca | acagagccct | cccatccccc | atcgagaaaa | ccatctcaaa | acccagaggg | 1080 |
| ccagtaagag | ctccacaggt | atatgtcttg | cctccaccag | cagaagagat | gactaagaaa | 1140 |
| gagttcagtc | tgacctgcat | gatcacaggc | ttcttacctg | ccgaaattgc | tgtggactgg | 1200 |
| accagcaatg | ggcgtacaga | gcaaaactac | aagaacaccg | caacagtcct | ggactctgat | 1260 |
| ggttcttact | tcatgtacag | caagctcaga | gtacaaaaga | gcacttggga | agaggaagt | 1320 |
| cttttcgcct | gctcagtggt | ccacgagggt | ctgcacaatc | accttacgac | taagaccatc | 1380 |
| tcccggtctc | tgggtaaa | | | | | 1398 |

<210> SEQ ID NO 14
<211> LENGTH: 466
<212> TYPE: PRT
<213> ORGANISM: Mus musculus

<400> SEQUENCE: 14

Met Glu Trp Ile Trp Ile Leu Leu Phe Ile Leu Ser Gly Thr Ala Gly
1               5                   10                  15

Val Gln Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Ser Tyr Gly Ile Ser Trp Val Lys Gln Arg Thr Gly Gln Gly Leu
    50                  55                  60

Glu Trp Ile Gly Glu Ile Tyr Pro Arg Ser Gly Asn Ala Tyr Tyr Asn

-continued

```
               65                  70                  75                  80
        Glu Lys Phe Lys Val Lys Ala Thr Leu Thr Ile Asp Lys Ser Ser Ser
                            85                  90                  95
        Thr Ala Tyr Met Glu Leu Arg Ser Leu Thr Ser Glu Asp Ser Ala Val
                           100                 105                 110
        Tyr Phe Cys Gly Gly Asn Tyr Tyr Trp Gly Gln Gly Thr Thr Leu Thr
                           115                 120                 125
        Val Ser Ser Ala Lys Thr Thr Ala Pro Ser Val Tyr Pro Leu Ala Pro
        130                 135                 140
        Val Cys Gly Gly Thr Thr Gly Ser Ser Val Thr Leu Gly Cys Leu Val
        145                 150                 155                 160
        Lys Gly Tyr Phe Pro Glu Pro Val Thr Leu Thr Trp Asn Ser Gly Ser
                           165                 170                 175
        Leu Ser Ser Gly Val His Thr Phe Pro Ala Leu Leu Gln Ser Gly Leu
                           180                 185                 190
        Tyr Thr Leu Ser Ser Ser Val Thr Val Thr Ser Asn Thr Trp Pro Ser
                           195                 200                 205
        Gln Thr Ile Thr Cys Asn Val Ala His Pro Ala Ser Ser Thr Lys Val
                           210                 215                 220
        Asp Lys Lys Ile Glu Pro Arg Val Pro Ile Thr Gln Asn Pro Cys Pro
        225                 230                 235                 240
        Pro Leu Lys Glu Cys Pro Pro Cys Ala Ala Pro Asp Leu Leu Gly Gly
                           245                 250                 255
        Pro Ser Val Phe Ile Phe Pro Pro Lys Ile Lys Asp Val Leu Met Ile
                           260                 265                 270
        Ser Leu Ser Pro Met Val Thr Cys Val Val Asp Val Ser Glu Asp
                           275                 280                 285
        Asp Pro Asp Val Gln Ile Ser Trp Phe Val Asn Asn Val Glu Val His
                           290                 295                 300
        Thr Ala Gln Thr Gln Thr His Arg Glu Asp Tyr Asn Ser Thr Leu Arg
        305                 310                 315                 320
        Val Val Ser Ala Leu Pro Ile Gln His Gln Asp Trp Met Ser Gly Lys
                           325                 330                 335
        Glu Phe Lys Cys Lys Val Asn Asn Arg Ala Leu Pro Ser Pro Ile Glu
                           340                 345                 350
        Lys Thr Ile Ser Lys Pro Arg Gly Pro Val Arg Ala Pro Gln Val Tyr
                           355                 360                 365
        Val Leu Pro Pro Pro Ala Glu Glu Met Thr Lys Lys Glu Phe Ser Leu
        370                 375                 380
        Thr Cys Met Ile Thr Gly Phe Leu Pro Ala Glu Ile Ala Val Asp Trp
        385                 390                 395                 400
        Thr Ser Asn Gly Arg Thr Glu Gln Asn Tyr Lys Asn Thr Ala Thr Val
                           405                 410                 415
        Leu Asp Ser Asp Gly Ser Tyr Phe Met Tyr Ser Lys Leu Arg Val Gln
                           420                 425                 430
        Lys Ser Thr Trp Glu Arg Gly Ser Leu Phe Ala Cys Ser Val Val His
                           435                 440                 445
        Glu Gly Leu His Asn His Leu Thr Thr Lys Thr Ile Ser Arg Ser Leu
                           450                 455                 460
        Gly Lys
        465

<210> SEQ ID NO 15
```

-continued

<211> LENGTH: 2222
<212> TYPE: DNA
<213> ORGANISM: Homo sapiens

<400> SEQUENCE: 15

```
agctggctca gggcgtccgc taggctcgga cgacctgctg agcctcccaa accgcttcca      60
taaggctttg ctttccaact tcagctacag tgttagctaa gtttggaaag aaggaaaaaa     120
gaaaatccct gggccccttt tcttttgttc tttgccaaag tcgtcgttgt agtcttttg      180
cccaaggctg ttgtgttttt agaggtgcta tctccagttc cttgcactcc tgttaacaag     240
cacctcagcg agagcagcag cagcgatagc agccgcagaa gagccagcgg ggtcgcctag     300
tgtcatgacc agggcgggag atcacaaccg ccagagagga tgctgtggat ccttggccga     360
ctacctgacc tctgcaaaat tccttctcta ccttggtcat tctctctcta cttggggaga     420
tcggatgtgg cactttgcgg tgtctgtgtt tctggtagag ctctatggaa acagcctcct     480
tttgacagca gtctacgggc tggtggtggc agggtctgtt ctggtcctgg gagccatcat     540
cggtgactgg gtggacaaga atgctagact taaagtggcc cagacctcgc tggtggtaca     600
gaatgtttca gtcatcctgt gtggaatcat cctgatgatg gttttcttac ataaacatga     660
gcttctgacc atgtaccatg gatgggttct cacttcctgc tatatcctga tcatcactat     720
tgcaaatatt gcaaatttgg ccagtactgc tactgcaatc acaatccaaa gggattggat     780
tgttgttgtt gcaggagaag acagaagcaa actagcaaat atgaatgcca caatacgaag     840
gattgaccag ttaaccaaca tcttagcccc catggctgtt ggccagatta tgacatttgg     900
ctccccagtc atcggctgtg ctttatttc gggatggaac ttggtatcca tgtgcgtgga     960
gtacgtcctg ctctggaagg tttaccagaa aaccccagct ctagctgtga agctggtct     1020
taaagaagag gaaactgaat tgaaacagct gaatttacac aaagatactg agccaaaacc    1080
cctggaggga actcatctaa tgggtgtgaa agactctaac atccatgagc ttgaacatga    1140
gcaagagcct acttgtgcct cccagatggc tgagcccttc cgtaccttcc gagatgatg     1200
ggtctcctac tacaaccagc ctgtgtttct ggctggcatg ggtcttgctt tcctttatat    1260
gactgtcctg ggctttgact gcatcaccac agggtacgcc tacactcagg gactgagtgg    1320
ttccatcctc agtattttga tgggagcatc agctataact ggaataatgg gaactgtagc    1380
tttttacttgg ctacgtcgaa aatgtggttt ggttcggaca ggtctgatct caggattggc    1440
acagctttcc tgtttgatct tgtgtgtgat ctctgtattc atgcctggaa gccccctgga    1500
cttgtccgtt tctccttttg aagatatccg atcaaggttc attcaaggag agtcaattac    1560
acctaccaag atacctgaaa ttacaactga aatatacatg tctaatgggt ctaattctgc    1620
taatattgtc ccggagacaa gtcctgaatc tgtgcccata atctctgtca gtctgctgtt    1680
tgcaggcgtc attgctgcta gaatcggtct ttggtccttt gatttaactg tgacacagtt    1740
gctgcaagaa aatgtaattg aatctgaaag aggcattata aatggtgtac agaactccat    1800
gaactatctt cttgatcttc tgcatttcat catggtcatc ctggctccaa atcctgaagc    1860
ttttggcttg ctcgtattga tttcagtctc ctttgtggca atgggccaca ttatgtattt    1920
ccgatttgcc caaaatactc tgggaaacaa gctctttgct tgcggtcctg atgcaaaaga    1980
agttaggaag gaaaatcaag caaatacatc tgttgtttga cagtttaa ctgttgctat       2040
cctgttacta gattatatag agcacatgtg cttattttgt actgcagaat tccaataaat    2100
ggctgggtgt tttgctctgt ttttaccaca gctgtgcctt gagaactaaa agctgtttag    2160
gaaacctaag tcagcagaaa ttaactgatt aatttcccctt atgttgaggc atggaaaaaa   2220
``` aa                                                                      2222

<210> SEQ ID NO 16
<211> LENGTH: 571
<212> TYPE: PRT
<213> ORGANISM: Homo sapiens

<400> SEQUENCE: 16

Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
            100                 105                 110

Val Phe Leu His Lys His Glu Leu Leu Thr Met Tyr His Gly Trp Val
        115                 120                 125

Leu Thr Ser Cys Tyr Ile Leu Ile Ile Thr Ile Ala Asn Ile Ala Asn
    130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Asn Ala Thr
                165                 170                 175

Ile Arg Arg Ile Asp Gln Leu Thr Asn Ile Leu Ala Pro Met Ala Val
            180                 185                 190

Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Val Leu Leu Trp
    210                 215                 220

Lys Val Tyr Gln Lys Thr Pro Ala Leu Ala Val Lys Ala Gly Leu Lys
225                 230                 235                 240

Glu Glu Glu Thr Glu Leu Lys Gln Leu Asn Leu His Lys Asp Thr Glu
                245                 250                 255

Pro Lys Pro Leu Glu Gly Thr His Leu Met Gly Val Lys Asp Ser Asn
            260                 265                 270

Ile His Glu Leu Glu His Glu Gln Glu Pro Thr Cys Ala Ser Gln Met
        275                 280                 285

Ala Glu Pro Phe Arg Thr Phe Arg Asp Gly Trp Val Ser Tyr Tyr Asn
    290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335

Leu Ser Gly Ser Ile Leu Ser Ile Leu Met Gly Ala Ser Ala Ile Thr
            340                 345                 350

Gly Ile Met Gly Thr Val Ala Phe Thr Trp Leu Arg Arg Lys Cys Gly
        355                 360                 365

```
Leu Val Arg Thr Gly Leu Ile Ser Gly Leu Ala Gln Leu Ser Cys Leu
    370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Ile Gln Gly Glu
                405                 410                 415

Ser Ile Thr Pro Thr Lys Ile Pro Glu Ile Thr Thr Glu Ile Tyr Met
                420                 425                 430

Ser Asn Gly Ser Asn Ser Ala Asn Ile Val Pro Glu Thr Ser Pro Glu
            435                 440                 445

Ser Val Pro Ile Ile Ser Val Ser Leu Leu Phe Ala Gly Val Ile Ala
    450                 455                 460

Ala Arg Ile Gly Leu Trp Ser Phe Asp Leu Thr Val Thr Gln Leu Leu
465                 470                 475                 480

Gln Glu Asn Val Ile Glu Ser Glu Arg Gly Ile Ile Asn Gly Val Gln
                485                 490                 495

Asn Ser Met Asn Tyr Leu Leu Asp Leu Leu His Phe Ile Met Val Ile
                500                 505                 510

Leu Ala Pro Asn Pro Glu Ala Phe Gly Leu Leu Val Leu Ile Ser Val
            515                 520                 525

Ser Phe Val Ala Met Gly His Ile Met Tyr Phe Arg Phe Ala Gln Asn
    530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
                565                 570

<210> SEQ ID NO 17
<211> LENGTH: 3773
<212> TYPE: DNA
<213> ORGANISM: Danio rerio

<400> SEQUENCE: 17
acgaggtgcg agcggctctg gccatttcgg gaattatatg ttttttattca catagttgtt      60 ctagaaaggt tatttctctc cgacttcagc tacagtgata gctaagtttg gagaggagaa     120
aagggagata ttcgtgattt gcgcaggaat atatttgcag cgaggattta ctttgcccga     180
gccttacaaa ggagttcaaa tcccggcgag aaaaaaacaa tcgataaaaa acgcacaatg     240
gacagccctg catcaaagaa acctcgctgt gagaggttcc gcgaattctt caagtctgca     300
aaattcctca tttacgtcgg acatgccctc tcgacatggg gggatcggat gtggaatttt     360
gctgtggctg tgtttctggt ggagctgtat ggcaatagtt tactcctgac agccgtgtat     420
ggactggtgg tcgcgggctc cgtgctctta ctgggcgcta ttattggtga ctgggttgac     480
aaaaacccca gattgaaagt ggcacagacg tctttggttg tccagaacag tgctgtcatt     540
ctctgtggtg cccttttgat ggctgttttc cagttcaaac aacagctttc tagcatgtat     600
gatggatggt tgctgacaac atgctacata atggtcatct ccattgctaa tatcgctaac     660
ctggccagca cagctatgtc catcaccatc caaagagact gggttgtggt tgtggctgga     720
gatgatcgga gcaaattggc agatatgaat gcaactgtca gaataattga ccagttgacc     780
aacattctgg caccgatgct gtgggccag atcatggcat ttggctcaca cttcattggc     840
tgtggtttta tctcgggctg gaacttgttc tccatgtgcc tggagtattt cctgctttgg     900
aaagtttatc agaaaactcc agcgcttgcc tttaaggcag acagaaagga tagcgatgac     960
```

```
caagagctga aacacctcaa catacaaaaa gaaattggaa acactgaaag cccggtcgaa    1020
gcctcccaac tgatgactga aagctccgag cccaagaagg acaccggctg ctgctaccaa    1080
atggcagagc ccatccgtac ctttaaagat ggctgggtag cctactacaa tcaatccatc    1140
ttcttcgccg gcatgtctct ggcttttccta tacatgaccg ttttgggctt cgactgcatc    1200
accacaggct atgcatacac tcagggcctg aatggctctg tgctcagtct cctcatggga    1260
gcctcagctg tatctgggat ctgtgggaca gtggccttca cctggatccg aaagaagtgc    1320
ggcctcatca ggacgggctt cattgctgga gtcacccagc tgtcctgcct cacgctgtgt    1380
gtagcatctg tcttcgcccc tggtagccct ttcgatctca gcgtctcgcc cttcaaagag    1440
gtcttaagac atctgtttgg agacagcggc tcgctgcgtg agagtcctac attcattcct    1500
acaactgaac ccccgattca ggccaacgtc accgttttg aggaagcccc cccagtagag    1560
tcctacatgt ctgttgggct ctctctttgcc ggtgttattg ctgctagagt tggtctttgg    1620
tccttcgact tgaccgtgac ccaactgatc aagagaatg tgattgagtc cgagagagga    1680
gtcatcaatg gcgtccagaa ctccatgaat tatcttctcg atctcctgca cttcatcatg    1740
gtcatccttg caccaaatcc tgaagccttt ggtcttcttg taatcatctc cgtttccttc    1800
gtggctatgg gacatatgat gtatttcagg tttgcttata aaagccttgg aagccgactc    1860
ttcctgttct gttcacccga gcagaagcca gatcccaaca ttccctcact tccaaactct    1920
gtatagcttt ttaaagagac cgtaggccat ttctacaaga gcgtggcttg ctgtgttctt    1980
tcagaacctt gccaggatcc catctgtttt actaacatgc atgcttttgc tgcttgcagt    2040
gctgtgcatt gagtaaatat cctctgccat aggctaaaat aacaaagaga aggagctctt    2100
cttagcatag catacttcac ttctcatatc atgttcaagg tgctgtaaaa atgccataga    2160
agcaaccgta ggaggaaata tatacatgga aactacggtt ctatcatgct ttaatgactt    2220
ttgtaagagc tccaaagcaa aaattagcat atttattcta ctttttacgta ttatattgtt    2280 tttttttttc aactttatgg tcgtagttaa ccttcagact ggttatgaca gttttgcaat    2340
gtgctctact tatgatagtg tagttttgta atgtttgtcc cttcttccaa gccttggtta    2400
aagtctcttt aatagctatt aagagtgcgc tagttataca ttcaggtaag cctatataat    2460
gcctatatat ttatatacac gtgtagtcag tattctttat ctcagcttcg gtggtgctac    2520
gttgtttcaa ctcttttgga aagccatgca ggcggtttat acatgtaacc aaagtggggtt    2580 ttttttggca tcacgtggaa gtgagggaat tgccgttttt ttatcgtgtt aaacattcca    2640
tattattatt attaccggtg tgatgatttc ttggagattt aggcgctgat aggctcccca    2700
tcgcagcaag agattttagc gctaggtatt tgtgctcctg tttgatttga aagtgatttt    2760
cgcacataat tcttgttttt atttgcaaag attgttacac atgcacttta catgattaat    2820
atacgttttc cattacgaaa caagcgcaac aagccctcag gtattacgat atttgcacaa    2880
tacacaaaac ctgtcgccga agttcacggc caggcaggaa atctgatatt tttacatgca    2940
aatttatttc aaaatgggat tttcaaagta cattaacctc aaacttcatg attttttacct    3000 tcctatataa gacaccacac ctcatacgct aatctagatt ttctataata caaagtaaag    3060
gttacagact gttctattag ctgagatgaa agccacaatc atagaagtac tactaacatc    3120
cttttaaaac cacagctggc tcgacataga tatatagata tatatatatg aggtgtttta    3180
taatagttgt gtaatattga tgttggacac cagcgggaat ccaccatatg cacagaacag    3240
agaagggatt attgagtcca gtgtgtgaac ggctggtttg cagcgcagct ggttccaaac    3300
```

-continued

```
acaggtgcca agtcacactt gacttgctaa gttagcgttt tctttaatgt gtgagaacta    3360
cttcatgagg ccccaacgaa cacactgtca gtctttcatt gtgtcagtct ttctgtgaat    3420
gtgaagcctt atttacatct gtaaaatatt tttttatatt cttatgttga ctagttttgt    3480
ttcaatcggg tttatcctcc tttgtaaggc cacagatttc ccccttttag acaagagaag    3540
taaacacatt tgcaataaat tgtactttcg acacccagtt gaatgtaaca gaagaaccta    3600
gattattctt tatataagca tattgattct gttcatgttt ggtggcatat ttgcaataat    3660
tgtggttcac actccatcgc agtgggagga ttatagaact ttagtcttgt attgtatctc    3720
acttcgactg aaataaacag atttgtatct aaaaaaaaaa aaaaaaaaaa aaa           3773
```

<210> SEQ ID NO 18
<211> LENGTH: 562
<212> TYPE: PRT
<213> ORGANISM: Danio rerio

<400> SEQUENCE: 18

```
Met Asp Ser Pro Ala Ser Lys Lys Pro Arg Cys Glu Arg Phe Arg Glu
1               5                   10                  15

Phe Phe Lys Ser Ala Lys Phe Leu Ile Tyr Val Gly His Ala Leu Ser
                20                  25                  30

Thr Trp Gly Asp Arg Met Trp Asn Phe Ala Val Ala Val Phe Leu Val
            35                  40                  45

Glu Leu Tyr Gly Asn Ser Leu Leu Leu Thr Ala Val Tyr Gly Leu Val
        50                  55                  60

Val Ala Gly Ser Val Leu Leu Gly Ala Ile Ile Gly Asp Trp Val
 65                 70                  75                  80

Asp Lys Asn Pro Arg Leu Lys Val Ala Gln Thr Ser Leu Val Val Gln
                85                  90                  95

Asn Ser Ala Val Ile Leu Cys Gly Ala Leu Leu Met Ala Val Phe Gln
                100                 105                 110

Phe Lys Gln Gln Leu Ser Ser Met Tyr Asp Gly Trp Leu Leu Thr Thr
            115                 120                 125

Cys Tyr Ile Met Val Ile Ser Ile Ala Asn Ile Ala Asn Leu Ala Ser
        130                 135                 140

Thr Ala Met Ser Ile Thr Ile Gln Arg Asp Trp Val Val Val Ala
145                 150                 155                 160

Gly Asp Asp Arg Ser Lys Leu Ala Asp Met Asn Ala Thr Val Arg Ile
                165                 170                 175

Ile Asp Gln Leu Thr Asn Ile Leu Ala Pro Met Leu Val Gly Gln Ile
            180                 185                 190

Met Ala Phe Gly Ser His Phe Ile Gly Cys Gly Phe Ile Ser Gly Trp
        195                 200                 205

Asn Leu Phe Ser Met Cys Leu Glu Tyr Phe Leu Leu Trp Lys Val Tyr
    210                 215                 220

Gln Lys Thr Pro Ala Leu Ala Phe Lys Ala Gly Gln Lys Asp Ser Asp
225                 230                 235                 240

Asp Gln Glu Leu Lys His Leu Asn Ile Gln Lys Glu Ile Gly Asn Thr
                245                 250                 255

Glu Ser Pro Val Glu Ala Ser Gln Leu Met Thr Glu Ser Glu Pro
            260                 265                 270

Lys Lys Asp Thr Gly Cys Cys Tyr Gln Met Ala Glu Pro Ile Arg Thr
        275                 280                 285

Phe Lys Asp Gly Trp Val Ala Tyr Tyr Asn Gln Ser Ile Phe Phe Ala
```

```
                   290                 295                 300
Gly Met Ser Leu Ala Phe Leu Tyr Met Thr Val Leu Gly Phe Asp Cys
305                 310                 315                 320

Ile Thr Thr Gly Tyr Ala Tyr Thr Gln Gly Leu Asn Gly Ser Val Leu
                325                 330                 335

Ser Leu Leu Met Gly Ala Ser Ala Val Ser Gly Ile Cys Gly Thr Val
                340                 345                 350

Ala Phe Thr Trp Ile Arg Lys Lys Cys Gly Leu Ile Arg Thr Gly Phe
            355                 360                 365

Ile Ala Gly Val Thr Gln Leu Ser Cys Leu Thr Leu Cys Val Ala Ser
        370                 375                 380

Val Phe Ala Pro Gly Ser Pro Phe Asp Leu Ser Val Ser Pro Phe Lys
385                 390                 395                 400

Glu Val Leu Arg His Leu Phe Gly Asp Ser Gly Ser Leu Arg Glu Ser
                405                 410                 415

Pro Thr Phe Ile Pro Thr Thr Glu Pro Pro Ile Gln Ala Asn Val Thr
                420                 425                 430

Val Phe Glu Glu Ala Pro Pro Val Glu Ser Tyr Met Ser Val Gly Leu
            435                 440                 445

Leu Phe Ala Gly Val Ile Ala Ala Arg Val Gly Leu Trp Ser Phe Asp
        450                 455                 460

Leu Thr Val Thr Gln Leu Ile Gln Glu Asn Val Ile Glu Ser Glu Arg
465                 470                 475                 480

Gly Val Ile Asn Gly Val Gln Asn Ser Met Asn Tyr Leu Leu Asp Leu
                485                 490                 495

Leu His Phe Ile Met Val Ile Leu Ala Pro Asn Pro Glu Ala Phe Gly
                500                 505                 510

Leu Leu Val Ile Ile Ser Val Ser Phe Val Ala Met Gly His Met Met
            515                 520                 525

Tyr Phe Arg Phe Ala Tyr Lys Ser Leu Gly Ser Arg Leu Phe Leu Phe
        530                 535                 540

Cys Ser Pro Glu Gln Lys Pro Asp Pro Asn Ile Pro Ser Leu Pro Asn
545                 550                 555                 560

Ser Val

<210> SEQ ID NO 19
<211> LENGTH: 2130
<212> TYPE: DNA
<213> ORGANISM: Mus musculus

<400> SEQUENCE: 19
agagcaggct gggggtctcc tgcggccggt ggatcctcca acccgctccc ataaggcttt      60
ggctttccaa cttcagctac agtgttagct aagtttggaa agaagacaaa aagaagaccc     120
cgtgacagct tgctgttgt tgtttgcctt agttgtcctt gggggtcttt cggcataagg      180
ctgttgtgct tatactggtg ctatcttcgg ttcctctcac tcctgtgaac aagctcccgg     240
gcaagagcag ctaaagctac cagcatcaga acaaacaagg ggagaacgcc tggtgtcatg     300
accaaggcaa gagatcaaac ccatcaggaa ggatgctgtg gatccttagc aaactacctg     360
acctcagcaa aattcctcct ctaccttggc cactctctct ccacttgggg ggatcggatg     420
tggcactttg cagtgtctgt gtttctggtg gaactctatg gaaacagcct tctcttgaca     480
gctgtctatg gactggtggt ggcaggctct gttctggtcc tggagccat cattggtgac     540 tgggtggata agaatgccag acttaaagtg gcccagacgt cactggtggt tcagaatgtg     600
```

```
tccgtcatcc tctgcggaat catcctgatg atggttttcc tacacaagaa tgagctcctg      660
accatgtacc atggatgggt ccttactgtc tgctacatcc tgatcatcac tattgcaaac      720
attgcaaatt tggccagtac tgccactgcg atcacaatcc aaagggactg gattgttgtt      780
gtggcaggag aaaacaggag cagattagca gacatgaatg ctaccattag aaggattgac      840
cagctaacca acatcctggc ccccatggct gtcggccaga ttatgacatt tggttctcca      900
gtcattggct gtggttttat ttccggttgg aatttggtgt ccatgtgtgt ggagtacttc      960
ttgctctgga aggtttacca aagaccccct gctctggctg taaaagctgc tctcaaggta     1020
gaggagtcag aactgaagca gctgacctca cctaaagata ctgagccaaa acctttggag     1080
ggaactcatc taatgggtga aaagactcc aacatccgtg aacttgaatg tgaacaagag     1140
cccacctgtg cctcccagat ggcagagccc ttccgcactt tccgagatgg atgggtctcc     1200
tactataacc agccagtgtt tctggctggc atgggcctgg ctttcctcta tatgacagtc     1260
ctgggctttg actgtatcac tacagggtac gcctacactc aggggctgag tggatccatc     1320 cttagtatt tgatgggagc atcagcaata actggaataa tgggaactgt ggccttcacc     1380
tggctacgtc gaaaatgtgg ccttgttcgg actggtctat tctcaggact agcccagctt     1440
tcctgtttaa tcttgtgtgt gatctccgta ttcatgcctg gaagcccctt ggacctgtct     1500
gtttctccat ttgaagatat ccgttctagg tttgtgaatg tggagccagt gtccccaact     1560
accaaaatac ctgagaccgt ctttacaaca gaaatgcata tgtccaacat gtctaatgtc     1620
catgagatga gtactaaacc catccccata gtctctgtca gcctgctgtt tgcaggagtc     1680
attgctgcta gaatcggtct ttggtccttt gatttgacgg tgacacagtt gctgcaagaa     1740
aatgtaattg aatctgaaag aggcattatc aatggtgtgc agaactccat gaactacctt     1800
cttgaccttc tgcatttcat catggtcatc ttggccccaa atcctgaagc ttttggcttg     1860
ctggtattga tttcagtctc ctttgtggca atgggacatc ttatgtattt ccgatttgcc     1920
cagaagactc tgggcaacca gatttttgtt tgtggtcctg atgaaaaaga agttacagat     1980
gaaaatcaac cgaatacatc tgttgtataa aaatagttta gctgtggccc ctgttactag     2040
attgtggaga gcatgtgtgc ttattttgta ctgcagaatc ccaataaatg cctgcatttc     2100
tctccaaaaa aaaaaaaaaa aaaaaaaaa                                       2130
```

<210> SEQ ID NO 20
<211> LENGTH: 570
<212> TYPE: PRT
<213> ORGANISM: Mus musculus

<400> SEQUENCE: 20

Met Thr Lys Ala Arg Asp Gln Thr His Gln Glu Gly Cys Cys Gly Ser
1               5                   10                  15

Leu Ala Asn Tyr Leu Thr Ser Ala Lys Phe Leu Leu Tyr Leu Gly His
                20                  25                  30

Ser Leu Ser Thr Trp Gly Asp Arg Met Trp His Phe Ala Val Ser Val
            35                  40                  45

Phe Leu Val Glu Leu Tyr Gly Asn Ser Leu Leu Leu Thr Ala Val Tyr
        50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

-continued

```
Val Val Gln Asn Val Ser Val Ile Leu Cys Gly Ile Ile Leu Met Met
            100             105             110

Val Phe Leu His Lys Asn Glu Leu Leu Thr Met Tyr His Gly Trp Val
        115             120             125

Leu Thr Val Cys Tyr Ile Leu Ile Ile Thr Ile Ala Asn Ile Ala Asn
        130             135             140

Leu Ala Ser Thr Ala Thr Ala Ile Thr Ile Gln Arg Asp Trp Ile Val
145             150             155             160

Val Val Ala Gly Glu Asn Arg Ser Arg Leu Ala Asp Met Asn Ala Thr
            165             170             175

Ile Arg Arg Ile Asp Gln Leu Thr Asn Ile Leu Ala Pro Met Ala Val
            180             185             190

Gly Gln Ile Met Thr Phe Gly Ser Pro Val Ile Gly Cys Gly Phe Ile
        195             200             205

Ser Gly Trp Asn Leu Val Ser Met Cys Val Glu Tyr Phe Leu Leu Trp
        210             215             220

Lys Val Tyr Gln Lys Thr Pro Ala Leu Ala Val Lys Ala Ala Leu Lys
225             230             235             240

Val Glu Glu Ser Glu Leu Lys Gln Leu Thr Ser Pro Lys Asp Thr Glu
            245             250             255

Pro Lys Pro Leu Glu Gly Thr His Leu Met Gly Glu Lys Asp Ser Asn
            260             265             270

Ile Arg Glu Leu Glu Cys Gly Gln Glu Pro Thr Cys Ala Ser Gln Met
            275             280             285

Ala Glu Pro Phe Arg Thr Phe Arg Asp Gly Trp Val Ser Tyr Tyr Asn
        290             295             300

Gln Pro Val Phe Leu Ala Gly Met Gly Leu Ala Phe Leu Tyr Met Thr
305             310             315             320

Val Leu Gly Phe Asp Cys Ile Thr Thr Gly Tyr Ala Tyr Thr Gln Gly
                325             330             335

Leu Ser Gly Ser Ile Leu Ser Ile Leu Met Gly Ala Ser Ala Ile Thr
            340             345             350

Gly Ile Met Gly Thr Val Ala Phe Thr Trp Leu Arg Arg Lys Cys Gly
        355             360             365

Leu Val Arg Thr Gly Leu Phe Ser Gly Leu Ala Gln Leu Ser Cys Leu
        370             375             380

Ile Leu Cys Val Ile Ser Val Phe Met Pro Gly Ser Pro Leu Asp Leu
385             390             395             400

Ser Val Ser Pro Phe Glu Asp Ile Arg Ser Arg Phe Val Asn Val Glu
            405             410             415

Pro Val Ser Pro Thr Thr Lys Ile Pro Glu Thr Val Phe Thr Thr Glu
            420             425             430

Met His Met Ser Asn Met Ser Asn Val His Glu Met Ser Thr Lys Pro
        435             440             445

Ile Pro Ile Val Ser Val Ser Leu Leu Phe Ala Gly Val Ile Ala Ala
        450             455             460

Arg Ile Gly Leu Trp Ser Phe Asp Leu Thr Val Thr Gln Leu Leu Gln
465             470             475             480

Glu Asn Val Ile Glu Ser Arg Gly Ile Ile Asn Gly Val Gln Asn
            485             490             495

Ser Met Asn Tyr Leu Leu Asp Leu Leu His Phe Ile Met Val Ile Leu
        500             505             510

Ala Pro Asn Pro Glu Ala Phe Gly Leu Leu Val Leu Ile Ser Val Ser
```

```
                515                 520                 525
Phe Val Ala Met Gly His Leu Met Tyr Phe Arg Phe Ala Gln Lys Thr
            530                 535                 540

Leu Gly Asn Gln Ile Phe Val Cys Gly Pro Asp Glu Lys Glu Val Thr
545                 550                 555                 560

Asp Glu Asn Gln Pro Asn Thr Ser Val Val
                565                 570

<210> SEQ ID NO 21
<211> LENGTH: 193
<212> TYPE: PRT
<213> ORGANISM: Homo sapiens

<400> SEQUENCE: 21

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 22
<211> LENGTH: 193
<212> TYPE: PRT
<213> ORGANISM: Homo sapiens

<400> SEQUENCE: 22

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80
```

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 23
<211> LENGTH: 301
<212> TYPE: DNA
<213> ORGANISM: Artificial Sequence
<220> FEATURE:
<223> OTHER INFORMATION: Synthetic Polynucleotide

<400> SEQUENCE: 23
tcggccccgc ctcctgccac cgcagattgg ccgctagccc tccccgagcg ccctgcctcc      60
gagggccggc gcaccataaa agaagccgcc ctagccacgt cccctcgcag ttcggcggtc     120
ccgcgggtct gtctcttgct tcaacagtgt ttggacggaa cagatccggg gactctcttc     180
cagcctccga ccgccctccg atttcctctc cgcttgcaac ctccgggacc atcttctcgg     240
ccatctcctg cttctgggac ctgccagcac cgttttttgtg gttagctcct tcttgccaac     300
c                                                                     301

<210> SEQ ID NO 24
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 24

Ala Lys Phe Val Ala Ala Trp Thr Leu Lys Ala Ala Ala
1               5                   10

<210> SEQ ID NO 25
<211> LENGTH: 321
<212> TYPE: DNA
<213> ORGANISM: Homo sapiens

<400> SEQUENCE: 25
tcctatgagt tgacacagcc accctcggtg tcagtgtccc ctggacagac ggccaggatc      60
acctgctctg gagatgaatt gccaaagcaa tatgcttatt ggtaccagca gaaggcaggc     120
caggcccctg taatggtgat tcataaagac agtgagaggc cctcagggat ccctgagcga     180
ttctctggct ccagcgcagg gacaattgtc acgttgacca tcagtggagt ccaggcagaa     240
gacgaggctg actattactg tcaatcacca gacagcagac gtactgtgat attcggcgga     300
gggaccaagc tgaccgtcct a                                               321

<210> SEQ ID NO 26
<211> LENGTH: 107
<212> TYPE: PRT
<213> ORGANISM: Homo sapiens

<400> SEQUENCE: 26

Ser Tyr Glu Leu Thr Gln Pro Pro Ser Val Ser Val Ser Pro Gly Gln
1               5                   10                  15

Thr Ala Arg Ile Thr Cys Ser Gly Asp Glu Leu Pro Lys Gln Tyr Ala
            20                  25                  30

Tyr Trp Tyr Gln Gln Lys Ala Gly Gln Ala Pro Val Met Val Ile His
        35                  40                  45

Lys Asp Ser Glu Arg Pro Ser Gly Ile Pro Glu Arg Phe Ser Gly Ser
    50                  55                  60

Ser Ala Gly Thr Ile Val Thr Leu Thr Ile Ser Gly Val Gln Ala Glu
65                  70                  75                  80

Asp Glu Ala Asp Tyr Tyr Cys Gln Ser Pro Asp Ser Arg Arg Thr Val
                85                  90                  95

Ile Phe Gly Gly Gly Thr Lys Leu Thr Val Leu
            100                 105

<210> SEQ ID NO 27
<211> LENGTH: 360
<212> TYPE: DNA
<213> ORGANISM: Homo sapiens

<400> SEQUENCE: 27
caggtgcagc tggtggagtc tgggggaggc gtggtccagc ctgggaggtc cctgagactc      60
tcctgtgcag cgtctggatt caccttcagt ggctatggca tgcactgggt ccgccaggct     120
ccaggcaggg ggctggagtg ggtggcagtt atatggcctg atggaactaa taaatactat     180
gcagactccg tgaagggccg attcaccatc tccagagaca attccaagaa caaactgtat     240
ctgcaaatga acagcctgag agccgaggac acggctgtgt attactgtgc gagaggggga     300
gcaacagcag ttttcggtat gaacgtctgg ggccaaggga ccacggtcac cgtctctagt     360

<210> SEQ ID NO 28
<211> LENGTH: 120
<212> TYPE: PRT
<213> ORGANISM: Homo sapiens

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Arg Gly Leu Glu Trp Val
        35                  40                  45

Ala Val Ile Trp Pro Asp Gly Thr Asn Lys Tyr Tyr Ala Asp Ser Val
    50                  55                  60

Lys Gly Arg Phe Thr Ile Ser Arg Asp Asn Ser Lys Asn Lys Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Thr Ala Val Phe Gly Met Asn Val Trp Gly Gln
            100                 105                 110

Gly Thr Thr Val Thr Val Ser Ser

<210> SEQ ID NO 29
<211> LENGTH: 11
<212> TYPE: PRT
<213> ORGANISM: Homo sapiens

<400> SEQUENCE: 29

Ser Gly Asp Glu Leu Pro Lys Gln Tyr Ala Tyr
1               5                   10

<210> SEQ ID NO 30
<211> LENGTH: 7
<212> TYPE: PRT
<213> ORGANISM: Homo sapiens

<400> SEQUENCE: 30

Lys Asp Ser Glu Arg Pro Ser
1               5

<210> SEQ ID NO 31
<211> LENGTH: 10
<212> TYPE: PRT
<213> ORGANISM: Homo sapiens

<400> SEQUENCE: 31

Gln Ser Pro Asp Ser Arg Arg Thr Val Ile
1               5                   10

<210> SEQ ID NO 32
<211> LENGTH: 5
<212> TYPE: PRT
<213> ORGANISM: Homo sapiens

<400> SEQUENCE: 32

Gly Tyr Gly Met His
1               5

<210> SEQ ID NO 33
<211> LENGTH: 17
<212> TYPE: PRT
<213> ORGANISM: Homo sapiens

<400> SEQUENCE: 33

Val Ile Trp Pro Asp Gly Thr Asn Lys Tyr Tyr Ala Asp Ser Val Lys
1               5                   10                  15

Gly

<210> SEQ ID NO 34
<211> LENGTH: 11
<212> TYPE: PRT
<213> ORGANISM: Homo sapiens

<400> SEQUENCE: 34

Gly Gly Ala Thr Ala Val Phe Gly Met Asn Val
1               5                   10

<210> SEQ ID NO 35
<211> LENGTH: 336
<212> TYPE: DNA
<213> ORGANISM: Homo sapiens

<400> SEQUENCE: 35
gatattgtga tgacccagac tccactctcc tcacctgtca cccttggtca gccggcctcc      60

```
atctcctgca ggtctagtca aagcctcgta cacagtgatg gaaacaccta cttgagttgg        120
cttcagcaga ggccaggcca gcctccaaga ctcctaattt ataagatttc taaccggttc        180
tctggggtcc cagacagatt cagtggcagt gggacaggga cagatttcac actgaaaatc        240 agcaggtgg aagctgagga tgtcgggtt tatttctgca tgcaagctac acaatttccg          300
tggacgttcg gccaagggac caaggtggaa atcaaa                                  336
```

<210> SEQ ID NO 36
<211> LENGTH: 112
<212> TYPE: PRT
<213> ORGANISM: Homo sapiens

<400> SEQUENCE: 36

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Thr Gly Thr Asp Phe Thr Leu Lys Ile
65                  70                  75                  80

Ser Arg Val Glu Ala Glu Asp Val Gly Val Tyr Phe Cys Met Gln Ala
                85                  90                  95

Thr Gln Phe Pro Trp Thr Phe Gly Gln Gly Thr Lys Val Glu Ile Lys
            100                 105                 110
```

<210> SEQ ID NO 37
<211> LENGTH: 381
<212> TYPE: DNA
<213> ORGANISM: Homo sapiens

<400> SEQUENCE: 37

```
caggtgcagt ggtgcaatc tggggctgag gtgaagaagc ctgggtcctc agtgaaggtc          60
tcctgcaagg cttctggata caccctcacc ggctactaca tgcactgggt gcgacaggcc        120
cctggacaag gcttgagtg gatgggatgg atcaaccctc acactggtgg caaaaactat        180
gcacagaggt ttcagggcag ggtcaccctg accagggaca cgtccgtcaa cacggcctac      240
atggagctga acaccttgag atctgacgac acggccgttt attactgtgc gagagatcct      300
agtctagtag tgactgggcc ttccttctac tactacggtt tggacgtctg gggccaaggg      360
accacggtca ccgtctctag t                                                 381
```

<210> SEQ ID NO 38
<211> LENGTH: 127
<212> TYPE: PRT
<213> ORGANISM: Homo sapiens

<400> SEQUENCE: 38

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Leu Thr Gly Tyr
            20                  25                  30

Tyr Met His Trp Val Arg Gln Ala Pro Gly Gln Gly Leu Glu Trp Met
        35                  40                  45
```

Gly Trp Ile Asn Pro His Thr Gly Gly Lys Asn Tyr Ala Gln Arg Phe
    50                  55                  60

Gln Gly Arg Val Thr Leu Thr Arg Asp Thr Ser Val Asn Thr Ala Tyr
65                  70                  75                  80

Met Glu Leu Asn Thr Leu Arg Ser Asp Asp Thr Ala Val Tyr Tyr Cys
                85                  90                  95

Ala Arg Asp Pro Ser Leu Val Val Thr Gly Pro Ser Phe Tyr Tyr Tyr
            100                 105                 110

Gly Leu Asp Val Trp Gly Gln Gly Thr Thr Val Thr Val Ser Ser
        115                 120                 125

<210> SEQ ID NO 39
<211> LENGTH: 16
<212> TYPE: PRT
<213> ORGANISM: Homo sapiens

<400> SEQUENCE: 39

Arg Ser Ser Gln Ser Leu Val His Ser Asp Gly Asn Thr Tyr Leu Ser
1               5                   10                  15

<210> SEQ ID NO 40
<211> LENGTH: 7
<212> TYPE: PRT
<213> ORGANISM: Homo sapiens

<400> SEQUENCE: 40

Lys Ile Ser Asn Arg Phe Ser
1               5

<210> SEQ ID NO 41
<211> LENGTH: 9
<212> TYPE: PRT
<213> ORGANISM: Homo sapiens

<400> SEQUENCE: 41

Met Gln Ala Thr Gln Phe Pro Trp Thr
1               5

<210> SEQ ID NO 42
<211> LENGTH: 5
<212> TYPE: PRT
<213> ORGANISM: Homo sapiens

<400> SEQUENCE: 42

Gly Tyr Tyr Met His
1               5

<210> SEQ ID NO 43
<211> LENGTH: 17
<212> TYPE: PRT
<213> ORGANISM: Homo sapiens

<400> SEQUENCE: 43

Trp Ile Asn Pro His Thr Gly Gly Lys Asn Tyr Ala Gln Arg Phe Gln
1               5                   10                  15

Gly

<210> SEQ ID NO 44
<211> LENGTH: 18
<212> TYPE: PRT
<213> ORGANISM: Homo sapiens

<400> SEQUENCE: 44

Asp Pro Ser Leu Val Val Thr Gly Pro Ser Phe Tyr Tyr Tyr Gly Leu
1               5                   10                  15

Asp Val

<210> SEQ ID NO 45
<211> LENGTH: 336
<212> TYPE: DNA
<213> ORGANISM: Homo sapiens

<400> SEQUENCE: 45
gatattgtga tgacccagac tccactctcc tcacctgtca cccttggtca gccggcctcc      60
atctcctgca ggtctagtca aagcctcgta tacagtgatg gaaacaccta cttgagttgg     120
cttcagcaga ggccaggcca gcctccaaga ctcctagttt ataagatttc taaccggttc     180
tctggggtcc cagacagatt cagtggcagt ggggcaggga cagatttcac attgaaaatc     240
agcagggtgg aagctgagga tgtcggggtt tattactgca tgcaagctac acaatttccg     300
tggacgttcg gccaagggac caaggtggaa atcaaa                               336

<210> SEQ ID NO 46
<211> LENGTH: 112
<212> TYPE: PRT
<213> ORGANISM: Homo sapiens

<400> SEQUENCE: 46

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Val Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Trp Thr Phe Gly Gln Gly Thr Lys Val Glu Ile Lys
            100                 105                 110

<210> SEQ ID NO 47
<211> LENGTH: 381
<212> TYPE: DNA
<213> ORGANISM: Homo sapiens

<400> SEQUENCE: 47
caggtgcagt tggtgcaatc tggggctgag gtgaagaagc ctgggtcctc agtgaaggtc      60
tcctgtaagg cttctggata caccctcacc ggctactaca tgcactgggt gcgacaggcc     120
cctggacaag gcttgagtg gatgggatgg atcaaccctc acactggtgg caaaaactat     180
gcacagaagt tcagggcag ggtcaccctg accaggaca cgtccatcaa cacagcctac      240
atggagctga cacccttgag atctgacgac acggccgtgt attactgtgc gagagatcct     300
agtatagcag tggctgggcc ttccttctac tactacggtt tggacgtctg gggccaaggg     360
accacggtca ccgtctctag t                                               381

<210> SEQ ID NO 48

```
<211> LENGTH: 127
<212> TYPE: PRT
<213> ORGANISM: Homo sapiens

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Leu Thr Gly Tyr
                20                  25                  30

Tyr Met His Trp Val Arg Gln Ala Pro Gly Gln Gly Leu Glu Trp Met
            35                  40                  45

Gly Trp Ile Asn Pro His Thr Gly Gly Lys Asn Tyr Ala Gln Lys Phe
        50                  55                  60

Gln Gly Arg Val Thr Leu Thr Arg Asp Thr Ser Ile Asn Thr Ala Tyr
65                  70                  75                  80

Met Glu Leu Asn Thr Leu Arg Ser Asp Asp Thr Ala Val Tyr Tyr Cys
                85                  90                  95

Ala Arg Asp Pro Ser Ile Ala Val Ala Gly Pro Ser Phe Tyr Tyr Tyr
                100                 105                 110

Gly Leu Asp Val Trp Gly Gln Gly Thr Thr Val Thr Val Ser Ser
            115                 120                 125

<210> SEQ ID NO 49
<211> LENGTH: 16
<212> TYPE: PRT
<213> ORGANISM: Homo sapiens

<400> SEQUENCE: 49

Arg Ser Ser Gln Ser Leu Val Tyr Ser Asp Gly Asn Thr Tyr Leu Ser
1               5                   10                  15

<210> SEQ ID NO 50
<211> LENGTH: 7
<212> TYPE: PRT
<213> ORGANISM: Homo sapiens

<400> SEQUENCE: 50

Lys Ile Ser Asn Arg Phe Ser
1               5

<210> SEQ ID NO 51
<211> LENGTH: 9
<212> TYPE: PRT
<213> ORGANISM: Homo sapiens

<400> SEQUENCE: 51

Met Gln Ala Thr Gln Phe Pro Trp Thr
1               5

<210> SEQ ID NO 52
<211> LENGTH: 5
<212> TYPE: PRT
<213> ORGANISM: Homo sapiens

<400> SEQUENCE: 52

Gly Tyr Tyr Met His
1               5

<210> SEQ ID NO 53
<211> LENGTH: 17
<212> TYPE: PRT
<213> ORGANISM: Homo sapiens
```

<400> SEQUENCE: 53

Trp Ile Asn Pro His Thr Gly Gly Lys Asn Tyr Ala Gln Lys Phe Gln
1               5                   10                  15

Gly

<210> SEQ ID NO 54
<211> LENGTH: 18
<212> TYPE: PRT
<213> ORGANISM: Homo sapiens

<400> SEQUENCE: 54

Asp Pro Ser Ile Ala Val Ala Gly Pro Ser Phe Tyr Tyr Tyr Gly Leu
1               5                   10                  15

Asp Val

<210> SEQ ID NO 55
<211> LENGTH: 336
<212> TYPE: DNA
<213> ORGANISM: Homo sapiens

<400> SEQUENCE: 55
gatattgtga tgacccagac tccactctcc tcacctgtca cccatggtca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttg     180
tctggggtcc cagacagatt cagtggcagt gggacaggga cagatttcac actgaaaatc     240
agcagggtgg aagctgagga tgtcggggtt tatgtctgca tgcaagctac acaatttccg     300
tggacgttcg gccaagggac caaggtggaa atcaaa                               336

<210> SEQ ID NO 56
<211> LENGTH: 112
<212> TYPE: PRT
<213> ORGANISM: Homo sapiens

<400> SEQUENCE: 56

Asp Ile Val Met Thr Gln Thr Pro Leu Ser Ser Pro Val Thr His Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Leu Ser Gly Val Pro
    50                  55                  60

Asp Arg Phe Ser Gly Ser Gly Thr Gly Thr Asp Phe Thr Leu Lys Ile
65                  70                  75                  80

Ser Arg Val Glu Ala Glu Asp Val Gly Val Tyr Val Cys Met Gln Ala
                85                  90                  95

Thr Gln Phe Pro Trp Thr Phe Gly Gln Gly Thr Lys Val Glu Ile Lys
            100                 105                 110

<210> SEQ ID NO 57
<211> LENGTH: 381
<212> TYPE: DNA
<213> ORGANISM: Homo sapiens

<400> SEQUENCE: 57
caggtgcagt tggtgcaatc tggggctgag gtgaagaagc ctgggtcctc agtgaaggtc      60

```
tcctgcaagg cttctggata caccctcacc ggctactaca tgcactgggt gcgccaggcc      120
cctggacaag ggcttgagtg gatgggatgg atcaaccctc acactggtgg caaaaactat      180
gcccagaagt ttcagggcag ggtcaccctg accagggaca cgtccatcaa cacggcctac      240
atggaactga acaccttgag atctgacgac acggccgtgt attactgtgc gcgagatcct      300
agtctagtag tgactgggcc ttccttctac tactacggtt tggacgtctg ggggccaaggg     360 accacggtca ccgtctctag t                                                381
```

<210> SEQ ID NO 58
<211> LENGTH: 127
<212> TYPE: PRT
<213> ORGANISM: Homo sapiens

<400> SEQUENCE: 58

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Leu Thr Gly Tyr
                20                  25                  30

Tyr Met His Trp Val Arg Gln Ala Pro Gly Gln Gly Leu Glu Trp Met
            35                  40                  45

Gly Trp Ile Asn Pro His Thr Gly Gly Lys Asn Tyr Ala Gln Lys Phe
        50                  55                  60

Gln Gly Arg Val Thr Leu Thr Arg Asp Thr Ser Ile Asn Thr Ala Tyr
65                  70                  75                  80

Met Glu Leu Asn Thr Leu Arg Ser Asp Asp Thr Ala Val Tyr Tyr Cys
                85                  90                  95

Ala Arg Asp Pro Ser Leu Val Val Thr Gly Pro Ser Phe Tyr Tyr Tyr
                100                 105                 110

Gly Leu Asp Val Trp Gly Gln Gly Thr Thr Val Thr Val Ser Ser
            115                 120                 125
```

<210> SEQ ID NO 59
<211> LENGTH: 16
<212> TYPE: PRT
<213> ORGANISM: Homo sapiens

<400> SEQUENCE: 59

```
Arg Ser Ser Gln Ser Leu Val His Ser Asp Gly Asn Thr Tyr Leu Ser
1               5                   10                  15
```

<210> SEQ ID NO 60
<211> LENGTH: 7
<212> TYPE: PRT
<213> ORGANISM: Homo sapiens

<400> SEQUENCE: 60

```
Lys Ile Ser Asn Arg Leu Ser
1               5
```

<210> SEQ ID NO 61
<211> LENGTH: 9
<212> TYPE: PRT
<213> ORGANISM: Homo sapiens

<400> SEQUENCE: 61

```
Met Gln Ala Thr Gln Phe Pro Trp Thr
1               5
```

<210> SEQ ID NO 62
<211> LENGTH: 5
<212> TYPE: PRT
<213> ORGANISM: Homo sapiens

<400> SEQUENCE: 62

Gly Tyr Tyr Met His
1               5

<210> SEQ ID NO 63
<211> LENGTH: 17
<212> TYPE: PRT
<213> ORGANISM: Homo sapiens

<400> SEQUENCE: 63

Trp Ile Asn Pro His Thr Gly Gly Lys Asn Tyr Ala Gln Lys Phe Gln
1               5                   10                  15

Gly

<210> SEQ ID NO 64
<211> LENGTH: 18
<212> TYPE: PRT
<213> ORGANISM: Homo sapiens

<400> SEQUENCE: 64

Asp Pro Ser Leu Val Val Thr Gly Pro Ser Phe Tyr Tyr Tyr Gly Leu
1               5                   10                  15

Asp Val

<210> SEQ ID NO 65
<211> LENGTH: 339
<212> TYPE: DNA
<213> ORGANISM: Homo sapiens

<400> SEQUENCE: 65
gacatcgtga tgacccagtc tccagactcc ctggctgtgt ctctgggcga gagggccacc      60
atcaactgca agtccagcca gagtatttta tacagctcca acaataagaa ctacttagca     120
tggtaccagc agaaactcgg acagcctcct aagttgctca tttacggggc atctacccgg     180
gaatccgggg tccctgaccg attcagtggc agcgggtctg ggacagattt cactctcacc     240
atcagtagcc tgcaggctga agatgtggca gtttattact gtcagcaata ctatttact      300 ccattctctt tcggccctgg gaccaaagtg gatatcgaa                            339

<210> SEQ ID NO 66
<211> LENGTH: 113
<212> TYPE: PRT
<213> ORGANISM: Homo sapiens

<400> SEQUENCE: 66

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
                20                  25                  30

Ser Asn Asn Lys Asn Tyr Leu Ala Trp Tyr Gln Gln Lys Leu Gly Gln
            35                  40                  45

Pro Pro Lys Leu Leu Ile Tyr Gly Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Phe Thr Pro Phe Ser Phe Gly Pro Gly Thr Lys Val Asp Ile
            100                 105                 110

Glu

<210> SEQ ID NO 67
<211> LENGTH: 366
<212> TYPE: DNA
<213> ORGANISM: Homo sapiens

<400> SEQUENCE: 67
gaggtgcagc tgttggagtc tgggggaggc ctggtacagc ctggggggtc tctgagactc    60
tcctgtgcag cctctggatt cacttttagc agctttgcca tgacctgggt ccgccaggct   120
ccagggaagg gctggagtg gtctcagct attggtggta gtggtaggaa cacatactac   180
gcagactccg tgaagggccg gttcaccatc tccagagaca attccaagaa cacgctgtac   240
ctgcaaatga gcagcctgag agccgaggac acggccgtat attactgtgc gaaagagggg   300
gctatggctc ggcctccgag gggttggac gtctggggcc aagggaccac ggtcaccgtc   360
tctagt                                                              366

<210> SEQ ID NO 68
<211> LENGTH: 122
<212> TYPE: PRT
<213> ORGANISM: Homo sapiens

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Thr Trp Val Arg Gln Ala Pro Gly Lys Gly Leu Glu Trp Val
        35                  40                  45

Ser Ala Ile Gly Gly Ser Gly Arg Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
            85                  90                  95

Ala Lys Glu Gly Ala Met Ala Arg Pro Pro Arg Gly Leu Asp Val Trp
            100                 105                 110

Gly Gln Gly Thr Thr Val Thr Val Ser Ser
        115                 120

<210> SEQ ID NO 69
<211> LENGTH: 17
<212> TYPE: PRT
<213> ORGANISM: Homo sapiens

<400> SEQUENCE: 69

Lys Ser Ser Gln Ser Ile Leu Tyr Ser Ser Asn Asn Lys Asn Tyr Leu
1               5                   10                  15

Ala

<210> SEQ ID NO 70
<211> LENGTH: 7
<212> TYPE: PRT

<213> ORGANISM: Homo sapiens

<400> SEQUENCE: 70

Gly Ala Ser Thr Arg Glu Ser
1               5

<210> SEQ ID NO 71
<211> LENGTH: 9
<212> TYPE: PRT
<213> ORGANISM: Homo sapiens

<400> SEQUENCE: 71

Gln Gln Tyr Tyr Phe Thr Pro Phe Ser
1               5

<210> SEQ ID NO 72
<211> LENGTH: 5
<212> TYPE: PRT
<213> ORGANISM: Homo sapiens

<400> SEQUENCE: 72

Ser Phe Ala Met Thr
1               5

<210> SEQ ID NO 73
<211> LENGTH: 17
<212> TYPE: PRT
<213> ORGANISM: Homo sapiens

<400> SEQUENCE: 73

Ala Ile Gly Gly Ser Gly Arg Asn Thr Tyr Tyr Ala Asp Ser Val Lys
1               5                   10                  15
Gly

<210> SEQ ID NO 74
<211> LENGTH: 13
<212> TYPE: PRT
<213> ORGANISM: Homo sapiens

<400> SEQUENCE: 74

Glu Gly Ala Met Ala Arg Pro Pro Arg Gly Leu Asp Val
1               5                   10

<210> SEQ ID NO 75
<211> LENGTH: 336
<212> TYPE: DNA
<213> ORGANISM: Homo sapiens

<400> SEQUENCE: 75

```
gatattgtga tgacccagac tccactctcc tcacctgtca cccttggtca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttccg     300
tggacgttcg gccaagggac caaggtggaa atcaaa                               336
```

<210> SEQ ID NO 76
<211> LENGTH: 112
<212> TYPE: PRT
<213> ORGANISM: Homo sapiens

<400> SEQUENCE: 76

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Trp Thr Phe Gly Gln Gly Thr Lys Val Glu Ile Lys
            100                 105                 110

<210> SEQ ID NO 77
<211> LENGTH: 381
<212> TYPE: DNA
<213> ORGANISM: Homo sapiens

<400> SEQUENCE: 77
caggtgcagt tggtgcaatc tggggctgag gtgaagaagc ctgggtcctc agtgaaggtc      60
tcctgcaagg cttctggata cacccteacc ggctactaca tgcactgggt gcgacaggcc     120
cctggacaag gcttgagtg gatgggatgg atcaaccctc acactggtgg caaaaactat     180
ggacagaagt ttcagggcag ggtcaccctg accagggaca cgtccatcaa cacagcctac     240
atggagctga acagcttgag atctgacgac acggccgtgt attactgtgc gagagatcct     300
agtatatcag tggctgggcc ttccttctac tacttcggtt tggacgtctg gggccaaggg     360
accacggtca ccgtctctag t                                                381

<210> SEQ ID NO 78
<211> LENGTH: 127
<212> TYPE: PRT
<213> ORGANISM: Homo sapiens

<400> SEQUENCE: 78

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Leu Thr Gly Tyr
            20                  25                  30

Tyr Met His Trp Val Arg Gln Ala Pro Gly Gln Gly Leu Glu Trp Met
        35                  40                  45

Gly Trp Ile Asn Pro His Thr Gly Gly Lys Asn Tyr Gln Lys Phe
    50                  55                  60

Gln Gly Arg Val Thr Leu Thr Arg Asp Thr Ser Ile Asn Thr Ala Tyr
65                  70                  75                  80

Met Glu Leu Asn Ser Leu Arg Ser Asp Asp Thr Ala Val Tyr Tyr Cys
                85                  90                  95

Ala Arg Asp Pro Ser Ile Ser Val Ala Gly Pro Ser Tyr Tyr Phe
            100                 105                 110

Gly Leu Asp Val Trp Gly Gln Gly Thr Thr Val Thr Val Ser Ser
        115                 120                 125

<210> SEQ ID NO 79

```
<211> LENGTH: 16
<212> TYPE: PRT
<213> ORGANISM: Homo sapiens

<400> SEQUENCE: 79

Arg Ser Ser Gln Ser Leu Val His Ser Asp Gly Asn Thr Tyr Leu Ser
1               5                   10                  15

<210> SEQ ID NO 80
<211> LENGTH: 7
<212> TYPE: PRT
<213> ORGANISM: Homo sapiens

<400> SEQUENCE: 80

Lys Ile Ser Asn Arg Phe Ser
1               5

<210> SEQ ID NO 81
<211> LENGTH: 9
<212> TYPE: PRT
<213> ORGANISM: Homo sapiens

<400> SEQUENCE: 81

Met Gln Ala Thr Gln Phe Pro Trp Thr
1               5

<210> SEQ ID NO 82
<211> LENGTH: 5
<212> TYPE: PRT
<213> ORGANISM: Homo sapiens

<400> SEQUENCE: 82

Gly Tyr Tyr Met His
1               5

<210> SEQ ID NO 83
<211> LENGTH: 17
<212> TYPE: PRT
<213> ORGANISM: Homo sapiens

<400> SEQUENCE: 83

Trp Ile Asn Pro His Thr Gly Gly Lys Asn Tyr Gly Gln Lys Phe Gln
1               5                   10                  15

Gly

<210> SEQ ID NO 84
<211> LENGTH: 18
<212> TYPE: PRT
<213> ORGANISM: Homo sapiens

<400> SEQUENCE: 84

Asp Pro Ser Ile Ser Val Ala Gly Pro Ser Phe Tyr Tyr Phe Gly Leu
1               5                   10                  15

Asp Val

<210> SEQ ID NO 85
<211> LENGTH: 336
<212> TYPE: DNA
<213> ORGANISM: Homo sapiens

<400> SEQUENCE: 85
gatattgtga tgacccagac tccattctct tcacctgtca cccttggaca gccggcctcc      60
atctcctgca ggtctagtca aagcctcgta cacagtgatg gaaacaccta cttgagttgg     120
```

```
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tatttctgca tgcaagctac acaatttcct    300
tggacgttcg gccaagggac caaggtggaa atcaaa                              336
```

<210> SEQ ID NO 86
<211> LENGTH: 112
<212> TYPE: PRT
<213> ORGANISM: Homo sapiens

<400> SEQUENCE: 86

```
Asp Ile Val Met Thr Gln Thr Pro Phe Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Phe Cys Met Gln Ala
                85                  90                  95

Thr Gln Phe Pro Trp Thr Phe Gly Gln Gly Thr Lys Val Glu Ile Lys
            100                 105                 110
```

<210> SEQ ID NO 87
<211> LENGTH: 372
<212> TYPE: DNA
<213> ORGANISM: Homo sapiens

<400> SEQUENCE: 87

```
caggtgcagt tggtgcagtc tggggctgag gtgaagaagc ccggggcctc agtgaaggtc     60
tcctgcaagg cttctggata caccctcacc ggctactatc tgcactgggt gcgacaggcc    120
cctggacaag agcttgagtg gatgggatgg atcaacccct tcactggtgc cacagactat    180
gcacagaagt tcagggcag ggtcaccatg acccgggaca cgtccatcaa tacagcccac    240
atggagctga gcaggctgag atctgacgac acggccgtgt attactgtgc gagagaccc    300 tctctacaaa attcctacca ttactacgtc atggacgttt ggggccaagg gaccacggtc    360
accgtctcta gt                                                        372
```

<210> SEQ ID NO 88
<211> LENGTH: 124
<212> TYPE: PRT
<213> ORGANISM: Homo sapiens

<400> SEQUENCE: 88

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Gly Tyr
            20                  25                  30

Tyr Leu His Trp Val Arg Gln Ala Pro Gly Gln Glu Leu Glu Trp Met
        35                  40                  45

Gly Trp Ile Asn Pro Phe Thr Gly Ala Thr Asp Tyr Ala Gln Lys Phe
    50                  55                  60
```

Gln Gly Arg Val Thr Met Thr Arg Asp Thr Ser Ile Asn Thr Ala His
65                  70                  75                  80

Met Glu Leu Ser Arg Leu Arg Ser Asp Asp Thr Ala Val Tyr Tyr Cys
                85                  90                  95

Ala Arg Asp Pro Ser Leu Gln Asn Ser Tyr His Tyr Tyr Val Met Asp
            100                 105                 110

Val Trp Gly Gln Gly Thr Thr Val Thr Val Ser Ser
        115                 120

<210> SEQ ID NO 89
<211> LENGTH: 16
<212> TYPE: PRT
<213> ORGANISM: Homo sapiens

<400> SEQUENCE: 89

Arg Ser Ser Gln Ser Leu Val His Ser Asp Gly Asn Thr Tyr Leu Ser
1               5                   10                  15

<210> SEQ ID NO 90
<211> LENGTH: 7
<212> TYPE: PRT
<213> ORGANISM: Homo sapiens

<400> SEQUENCE: 90

Lys Ile Ser Asn Arg Phe Ser
1               5

<210> SEQ ID NO 91
<211> LENGTH: 9
<212> TYPE: PRT
<213> ORGANISM: Homo sapiens

<400> SEQUENCE: 91

Met Gln Ala Thr Gln Phe Pro Trp Thr
1               5

<210> SEQ ID NO 92
<211> LENGTH: 5
<212> TYPE: PRT
<213> ORGANISM: Homo sapiens

<400> SEQUENCE: 92

Gly Tyr Tyr Leu His
1               5

<210> SEQ ID NO 93
<211> LENGTH: 17
<212> TYPE: PRT
<213> ORGANISM: Homo sapiens

<400> SEQUENCE: 93

Trp Ile Asn Pro Phe Thr Gly Ala Thr Asp Tyr Ala Gln Lys Phe Gln
1               5                   10                  15

Gly

<210> SEQ ID NO 94
<211> LENGTH: 15
<212> TYPE: PRT
<213> ORGANISM: Homo sapiens

<400> SEQUENCE: 94

Asp Pro Ser Leu Gln Asn Ser Tyr His Tyr Tyr Val Met Asp Val

<210> SEQ ID NO 95
<211> LENGTH: 336
<212> TYPE: DNA
<213> ORGANISM: Homo sapiens

<400> SEQUENCE: 95

```
gatgttgtga tgacccagac tccactctcc tcacctgtca cccttggtca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccgattc     180
tctggggtcc cagacagatt cagtggcagt ggggcaggga cagatttcac actgaaaatc     240
agcagggtgg aagctgagga tgtcggggtt tattactgca tgcaagctac acaatttccg     300
tggacgttcg gccaagggac caaggtggaa atcaaa                               336
```

<210> SEQ ID NO 96
<211> LENGTH: 112
<212> TYPE: PRT
<213> ORGANISM: Homo sapiens

<400> SEQUENCE: 96

```
Asp Val Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Trp Thr Phe Gly Gln Gly Thr Lys Val Glu Ile Lys
            100                 105                 110
```

<210> SEQ ID NO 97
<211> LENGTH: 381
<212> TYPE: DNA
<213> ORGANISM: Homo sapiens

<400> SEQUENCE: 97

```
caggtgcagt tggtgcaatc tggggctgag gtgaagaagc ctgggtcctc agtgaaggtc      60
tcctgcaagg cttctggata caccctcacc ggctactaca tgcactgggt gcgacaggcc     120
cctggacaag gcttgagtg gatgggatgg atcaaccctc acactggtgg caaaaactat     180
gcccagaagt ttcagggcag ggtcaccctg accaggggaca cgtccatcag cacagcctac     240
atggagctga acagcttgag atctgacgac acggccgtgt attactgtgc gagagatcct     300
agtttatcag tgactgggcc ttccttctac tactacggtt tggacgtctg gggccaaggg     360
accacggtca ccgtctctag t                                               381
```

<210> SEQ ID NO 98
<211> LENGTH: 127
<212> TYPE: PRT
<213> ORGANISM: Homo sapiens

```
<400> SEQUENCE: 98

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Leu Thr Gly Tyr
            20                  25                  30

Tyr Met His Trp Val Arg Gln Ala Pro Gly Gln Gly Leu Glu Trp Met
        35                  40                  45

Gly Trp Ile Asn Pro His Thr Gly Gly Lys Asn Tyr Ala Gln Lys Phe
    50                  55                  60

Gln Gly Arg Val Thr Leu Thr Arg Asp Thr Ser Ile Ser Thr Ala Tyr
65                  70                  75                  80

Met Glu Leu Asn Ser Leu Arg Ser Asp Asp Thr Ala Val Tyr Tyr Cys
                85                  90                  95

Ala Arg Asp Pro Ser Leu Ser Val Thr Gly Pro Ser Phe Tyr Tyr Tyr
            100                 105                 110

Gly Leu Asp Val Trp Gly Gln Gly Thr Thr Val Thr Val Ser Ser
        115                 120                 125

<210> SEQ ID NO 99
<211> LENGTH: 16
<212> TYPE: PRT
<213> ORGANISM: Homo sapiens

<400> SEQUENCE: 99

Arg Ser Ser Gln Ser Leu Val His Ser Asp Gly Asn Thr Tyr Leu Ser
1               5                   10                  15

<210> SEQ ID NO 100
<211> LENGTH: 7
<212> TYPE: PRT
<213> ORGANISM: Homo sapiens

<400> SEQUENCE: 100

Lys Ile Ser Asn Arg Phe Ser
1               5

<210> SEQ ID NO 101
<211> LENGTH: 9
<212> TYPE: PRT
<213> ORGANISM: Homo sapiens

<400> SEQUENCE: 101

Met Gln Ala Thr Gln Phe Pro Trp Thr
1               5

<210> SEQ ID NO 102
<211> LENGTH: 5
<212> TYPE: PRT
<213> ORGANISM: Homo sapiens

<400> SEQUENCE: 102

Gly Tyr Tyr Met His
1               5

<210> SEQ ID NO 103
<211> LENGTH: 17
<212> TYPE: PRT
<213> ORGANISM: Homo sapiens

<400> SEQUENCE: 103

Trp Ile Asn Pro His Thr Gly Gly Lys Asn Tyr Ala Gln Lys Phe Gln
```

```
1               5                  10                 15
Gly

<210> SEQ ID NO 104
<211> LENGTH: 18
<212> TYPE: PRT
<213> ORGANISM: Homo sapiens

<400> SEQUENCE: 104

Asp Pro Ser Leu Ser Val Thr Gly Pro Ser Phe Tyr Tyr Tyr Gly Leu
1               5                   10                  15

Asp Val

<210> SEQ ID NO 105
<211> LENGTH: 348
<212> TYPE: DNA
<213> ORGANISM: Homo sapiens

<400> SEQUENCE: 105
cagcctgtgc tgactcagcc accttctgca tcagcctccc tgggagcctc ggtcacactc     60
acctgcaccc tgagcagcgg ctacaataat tataaagtgg actggttcca gcagcgacca    120
gggaggggcc cccgttttgt gatgcgagtg ggcactggtg ggattgtggg atccaagggg    180
gatggcatcc ctgatcgctt ctcagtcttg ggctcaggcc tgaatcggta cctgaccatc    240
aagaacatcc aggaagagga tgagagtgac taccactgtg gggcagacca tgccagtggg    300
aacaacttcg tgtatgtctt cggaactggg accaaggtca ccgtcccta               348

<210> SEQ ID NO 106
<211> LENGTH: 116
<212> TYPE: PRT
<213> ORGANISM: Homo sapiens

<400> SEQUENCE: 106

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Asn Asn Tyr Lys
                20                  25                  30

Val Asp Trp Phe Gln Gln Arg Pro Gly Arg Gly Pro Arg Phe Val Met
            35                  40                  45

Arg Val Gly Thr Gly Gly Ile Val Gly Ser Lys Gly Asp Gly Ile Pro
        50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Ala Ser Gly Asn Asn Phe Val Tyr Val Phe Gly Thr Gly Thr Lys
            100                 105                 110

Val Thr Val Leu
        115

<210> SEQ ID NO 107
<211> LENGTH: 366
<212> TYPE: DNA
<213> ORGANISM: Homo sapiens

<400> SEQUENCE: 107
gaagtgcagg tggtggagtc tgggggaggc ttggtacagc ctgggggtc cctgagactc     60
```

```
tcctgtgcag cctctggatt caccttcagt agctatagcg tgaactgggt ccgccaggct    120
ccagggaagg gcctggagtg ggtctcatac attagtggta gtagtagtac cgtacactac    180
gcagactctg tgaagggccg attcaccatt tccagagaca ctgccaagaa ttcagtgtat    240
ctgcaactga acagcctgag agacgaggac acggctctgt attactgtgc gagatgggga    300
actcgtcagg ccactacttt cggtatggac gtctggggcc aagggaccac ggtcaccgtc    360
tctagt                                                               366
```

<210> SEQ ID NO 108
<211> LENGTH: 122
<212> TYPE: PRT
<213> ORGANISM: Homo sapiens

<400> SEQUENCE: 108

```
Glu Val Gln Val Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ser Val Asn Trp Val Arg Gln Ala Pro Gly Lys Gly Leu Glu Trp Val
        35                  40                  45

Ser Tyr Ile Ser Gly Ser Ser Ser Thr Val His Tyr Ala Asp Ser Val
    50                  55                  60

Lys Gly Arg Phe Thr Ile Ser Arg Asp Thr Ala Lys Asn Ser Val Tyr
65                  70                  75                  80

Leu Gln Leu Asn Ser Leu Arg Asp Glu Asp Thr Ala Leu Tyr Tyr Cys
                85                  90                  95

Ala Arg Trp Gly Thr Arg Gln Gly His Tyr Phe Gly Met Asp Val Trp
            100                 105                 110

Gly Gln Gly Thr Thr Val Thr Val Ser Ser
        115                 120
```

<210> SEQ ID NO 109
<211> LENGTH: 12
<212> TYPE: PRT
<213> ORGANISM: Homo sapiens

<400> SEQUENCE: 109

```
Thr Leu Ser Ser Gly Tyr Asn Asn Tyr Lys Val Asp
1               5                  10
```

<210> SEQ ID NO 110
<211> LENGTH: 12
<212> TYPE: PRT
<213> ORGANISM: Homo sapiens

<400> SEQUENCE: 110

```
Val Gly Thr Gly Gly Ile Val Gly Ser Lys Gly Asp
1               5                  10
```

<210> SEQ ID NO 111
<211> LENGTH: 13
<212> TYPE: PRT
<213> ORGANISM: Homo sapiens

<400> SEQUENCE: 111

```
Gly Ala Asp His Ala Ser Gly Asn Asn Phe Val Tyr Val
1               5                  10
```

<210> SEQ ID NO 112

```
<211> LENGTH: 5
<212> TYPE: PRT
<213> ORGANISM: Homo sapiens

<400> SEQUENCE: 112

Ser Tyr Ser Val Asn
1               5

<210> SEQ ID NO 113
<211> LENGTH: 17
<212> TYPE: PRT
<213> ORGANISM: Homo sapiens

<400> SEQUENCE: 113

Tyr Ile Ser Gly Ser Ser Ser Thr Val His Tyr Ala Asp Ser Val Lys
1               5                   10                  15

Gly

<210> SEQ ID NO 114
<211> LENGTH: 13
<212> TYPE: PRT
<213> ORGANISM: Homo sapiens

<400> SEQUENCE: 114

Trp Gly Thr Arg Gln Gly His Tyr Phe Gly Met Asp Val
1               5                   10

<210> SEQ ID NO 115
<211> LENGTH: 5
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 115

Gly Tyr Xaa Met His
1               5

<210> SEQ ID NO 116
<211> LENGTH: 5
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 116

Gly Tyr Tyr Xaa His
1               5

<210> SEQ ID NO 117
<211> LENGTH: 17
<212> TYPE: PRT
<213> ORGANISM: Homo sapiens
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 117
```

```
Trp Ile Asn Pro His Thr Gly Gly Lys Asn Tyr Xaa Gln Xaa Phe Gln
1               5                   10                  15

Gly

<210> SEQ ID NO 118
<211> LENGTH: 18
<212> TYPE: PRT
<213> ORGANISM: Homo sapiens
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 118

Asp Pro Ser Xaa Xaa Val Xaa Gly Pro Ser Phe Tyr Tyr Xaa Gly Leu
1               5                   10                  15

Asp Val

<210> SEQ ID NO 119
<211> LENGTH: 7
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 119

Lys Ile Ser Asn Arg Xaa Ser
1               5

<210> SEQ ID NO 120
<211> LENGTH: 990
<212> TYPE: DNA
<213> ORGANISM: Homo sapiens

<400> SEQUENCE: 120
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcggaggga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
```

-continued

```
gccgtggagt gggagagcaa tgggcagccg agaacaact  acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 121
<211> LENGTH: 330
<212> TYPE: PRT
<213> ORGANISM: Homo sapiens

<400> SEQUENCE: 121

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 122
<211> LENGTH: 978
<212> TYPE: DNA
<213> ORGANISM: Homo sapiens

<400> SEQUENCE: 122

```
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag cgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct cctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaa                                                  978
```

<210> SEQ ID NO 123
<211> LENGTH: 326
<212> TYPE: PRT
<213> ORGANISM: Homo sapiens

<400> SEQUENCE: 123

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160
```

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 124
<211> LENGTH: 321
<212> TYPE: DNA
<213> ORGANISM: Homo sapiens

<400> SEQUENCE: 124
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgcccc tcaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                              321

<210> SEQ ID NO 125
<211> LENGTH: 107
<212> TYPE: PRT
<213> ORGANISM: Homo sapiens

<400> SEQUENCE: 125

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 126
<211> LENGTH: 318
<212> TYPE: DNA
<213> ORGANISM: Homo sapiens

<400> SEQUENCE: 126
ggtcagccca aggccaaccc cactgtcact ctgttcccgc cctcctctga ggagctccaa     60
gccaacaagg ccacactagt gtgtctgatc agtgacttct acccgggagc tgtgacagtg    120
gcctggaagg cagatggcag ccccgtcaag gcgggagtgg agaccaccaa accctccaaa    180
cagagcaaca caagtacgc ggccagcagc tacctgagcc tgacgcccga gcagtggaag    240
tcccacagaa gctacagctg ccaggtcacg catgaaggga gcaccgtgga agacagtg     300 gcccctacag aatgttca                                                 318

<210> SEQ ID NO 127
<211> LENGTH: 106
<212> TYPE: PRT
<213> ORGANISM: Homo sapiens

<400> SEQUENCE: 127

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 128
<211> LENGTH: 318
<212> TYPE: DNA
<213> ORGANISM: Homo sapiens

<400> SEQUENCE: 128
ggtcagccca aggctgcccc ctcggtcact ctgttcccgc cctcctctga ggagcttcaa     60
gccaacaagg ccacactggt gtgtctcata agtgacttct acccgggagc cgtgacagtg    120
gcctggaagg cagatagcag ccccgtcaag gcgggagtgg agaccaccac accctccaaa    180
caaagcaaca caagtacgc ggccagcagc tatctgagcc tgacgcctga gcagtggaag    240
tcccacagaa gctacagctg ccaggtcacg catgaaggga gcaccgtgga agacagtg     300 gcccctacag aatgttca                                                 318

<210> SEQ ID NO 129
<211> LENGTH: 106
<212> TYPE: PRT
<213> ORGANISM: Homo sapiens -continued

<400> SEQUENCE: 129

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 130
<211> LENGTH: 318
<212> TYPE: DNA
<213> ORGANISM: Homo sapiens

<400> SEQUENCE: 130
ggtcagccca aggctgcccc ctcggtcact ctgttcccac cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tacctgagcc tgacgcctga gcagtggaag     240
tcccacagaa gctacagctg ccaggtcacg catgaaggga gcaccgtgga agacagtg       300
gcccctacag aatgttca                                                   318

<210> SEQ ID NO 131
<211> LENGTH: 106
<212> TYPE: PRT
<213> ORGANISM: Homo sapiens

<400> SEQUENCE: 131

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 132
<211> LENGTH: 318
<212> TYPE: DNA
<213> ORGANISM: Homo sapiens

<400> SEQUENCE: 132

```
ggtcagccca aggctgcccc atcggtcact ctgttcccgc cctcctctga ggagcttcaa    60
gccaacaagg ccacactggt gtgcctgatc agtgacttct acccgggagc tgtgaaagtg   120
gcctggaagg cagatggcag ccccgtcaac acgggagtgg agaccaccac accctccaaa   180
cagagcaaca acaagtacgc ggccagcagc tacctgagcc tgacgcctga gcagtggaag   240
tcccacagaa gctacagctg ccaggtcacg catgaaggga gcaccgtgga gaagacagtg   300
gcccctgcag aatgtgca                                                 318
```

<210> SEQ ID NO 133
<211> LENGTH: 106
<212> TYPE: PRT
<213> ORGANISM: Homo sapiens

<400> SEQUENCE: 133

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ala
            100                 105

<210> SEQ ID NO 134
<211> LENGTH: 318
<212> TYPE: DNA
<213> ORGANISM: Homo sapiens

<400> SEQUENCE: 134

```
ggtcagccca aggctgcccc ctcggtcact ctgttcccac cctcctctga ggagcttcaa    60
gccaacaagg ccacactggt gtgtctcgta agtgacttct acccgggagc cgtgacagtg   120
gcctggaagg cagatggcag ccccgtcaag gtgggagtgg agaccaccaa accctccaaa   180
caaagcaaca acaagtatgc ggccagcagc tacctgagcc tgacgcccga gcagtggaag   240
tcccacagaa gctacagctg ccgggtcacg catgaaggga gcaccgtgga gaagacagtg   300
gcccctgcag aatgctct                                                 318
```

<210> SEQ ID NO 135
<211> LENGTH: 106
<212> TYPE: PRT
<213> ORGANISM: Homo sapiens

<400> SEQUENCE: 135

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

-continued

```
Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
                100                 105

<210> SEQ ID NO 136
<211> LENGTH: 17
<212> TYPE: PRT
<213> ORGANISM: Homo sapiens
<220> FEATURE:
<221> NAME/KEY: misc_feature
<222> LOCATION: (12)..(12)
<223> OTHER INFORMATION: wherein  X is A, G, K, R, any combination
      thereof, or conservative substitution thereof;
<220> FEATURE:
<221> NAME/KEY: misc_feature
<222> LOCATION: (14)..(14)
<223> OTHER INFORMATION: wherein  X is A, G, K, R, any combination
      thereof, or conservative substitution thereof;

<400> SEQUENCE: 136

Trp Ile Asn Pro His Thr Gly Gly Lys Asn Tyr Xaa Gln Xaa Phe Gln
1               5                   10                  15

Gly

<210> SEQ ID NO 137
<211> LENGTH: 18
<212> TYPE: PRT
<213> ORGANISM: Homo sapiens
<220> FEATURE:
<221> NAME/KEY: misc_feature
<222> LOCATION: (4)..(5)
<223> OTHER INFORMATION: wherein X is A, F, I, L, V, S, T, Y any
      combination thereof, or conservative substitution thereof
<220> FEATURE:
<221> NAME/KEY: misc_feature
<222> LOCATION: (7)..(7)
<223> OTHER INFORMATION: wherein X is A, F, I, L, V, S, T, Y any
      combination thereof, or conservative substitution thereof
<220> FEATURE:
<221> NAME/KEY: misc_feature
<222> LOCATION: (14)..(14)
<223> OTHER INFORMATION: wherein X is A, F, I, L, V, S, T, Y any
      combination thereof, or conservative substitution thereof

<400> SEQUENCE: 137

Asp Pro Ser Xaa Xaa Val Xaa Gly Pro Ser Phe Tyr Tyr Xaa Gly Leu
1               5                   10                  15

Asp Val
```

FERROPORTIN ANTIBODIES AND METHODS OF USE

CROSS-REFERENCE TO RELATED APPLICATIONS

This application is a continuation of U.S. Ser. No. 12/863,737, filed Jun. 6, 2011, which is a national phase entry of International Application No. PCT/US2009/031851, filed Jan. 23, 2009, which claims the benefit of priority of U.S. Provisional Application No. 61/121,729, filed Dec. 11, 2008 and the benefit of priority of U.S. Provisional Application No. 61/023,693, filed Jan. 25, 2008. The disclosure of each priority application is hereby incorporated by reference in its entirety.

REFERENCE TO THE SEQUENCE LISTING

The present application contains a Sequence Listing which has been submitted electronically in ASCII format and is hereby incorporated by reference in its entirety. Said ASCII copy, created on Sep. 24, 2015, is named A-1393-US-CNT_ST25.txt and is 103,239 bytes in size.

FIELD OF THE INVENTION

The invention relates to ferroportin antibodies and uses thereof.

BACKGROUND

Iron is an essential trace element required for growth and development of all living organisms. Iron content in mammals is regulated by controlling iron absorption, iron recycling, and release of iron from the cells in which it is stored. Iron release is controlled by ferroportin, a major iron export protein located on the cell surface of enterocytes, macrophages and hepatocytes, the main cells capable of releasing iron into plasma. Ferroportin, also known as MTP1 or Ferroportin-1, is a multipass transmembrane protein that mediates cellular iron efflux (Donovan et al., Nature, 403: 776-781, 2000; Abboud et al., J. Biol. Chem., 275:19906-19912, 2000). Ferroportin is highly expressed in duodenal enterocytes and macrophages of the reticuloendothelial system where it is involved in transport of iron from the diet and the recycling of iron from senescent red blood cells, respectively (Yang et al., J. Biol. Chem., 277:39786-39791, 2002). Ferroportin is negatively regulated by the iron-regulatory hormone hepcidin. Hepcidin has been shown to bind ferroportin, resulting in internalization and degradation of ferroportin (Nemeth et al., Blood, 107:328-333, 2006; Nemeth et al., *Science,* 306:2090-2093, 2004; de Domenico et al., Mol. Biol. Cell., 8:2569-2578, 2007). This mechanism blocks the release of iron from macrophages, hepatocytes and enterocytes (Knutson et al., Proc. Natl. Acad. Sci. USA, 102:1324-1328, 2008; Nemeth et al., Blood, 107:328-333, 2006; Knutson et al., Blood, 102:4191-4197, 2003).

Ferroportin is important for iron efflux as demonstrated in transgenic mice: deletion of ferroportin is embryonically lethal whereas inactivation of ferroportin by a conditional knockout results in increased iron storage in enterocytes, macrophages and hepatocytes (Donovan et al., Cell. Metab., 1:191-200, 2005). Thomas and Oates, Gut, 2004; 53; 44-49, reported that a polyclonal antibody generated using a rat ferroportin peptide sequence Genbank Accession No. AAK77858 (predicted to be between transmembrane domains 3 and 4) reduced cellular iron uptake but had no effect on iron release.

SUMMARY OF THE INVENTION

Various embodiments of the invention provide antibodies, including monoclonal antibodies, that bind human ferroportin, methods of producing such antibodies, methods of using such antibodies for detecting ferroportin, pharmaceutical formulations including such antibodies, methods of preparing the pharmaceutical formulations, and methods of treating patients with the pharmaceutical formulations, including combination therapy with erythropoiesis stimulators and/or iron chelators as described below. Nucleic acids encoding such antibodies, vectors and recombinant host cells comprising such nucleic acids, and methods of producing such antibodies are also provided.

In one aspect, the antibody is an antibody, for example, an isolated monoclonal antibody, that binds to an extracellular domain of ferroportin (SEQ ID NO: 16), with the desired affinity. In some embodiments, the antibody's affinity kd for cells expressing ferroportin is about $10^{-6}$ M or less, or about $10^{-7}$ M or less, or about $10^{-8}$ M or less, or about $10^{-9}$ M or less. In some embodiments, the extracellular domain of ferroportin comprises an amino acid sequence selected from the group consisting of amino acids 46-60, 116-126, 204-205, 325-342, 394-449, 513-517, 35-57, 116-124, 332-340, 393-449 and 515-518 of SEQ ID NO: 16 and fragments thereof at least 4, 5, 6, 7, 8, 9, 10, 11 or 12 amino acids in length. In some embodiments, the antibody inhibits internalization and/or degradation of ferroportin. In some embodiments, the antibody inhibits hepcidin-mediated internalization or degradation of ferroportin. In one embodiment, the antibody decreases intracellular iron concentration and/or increases circulating iron concentration at an $EC_{50}$ of about $10^{-6}$ M or less, or about $10^{-7}$ M or less, or about $10^{-8}$ M or less, or about $10^{-9}$ M or less. In other embodiments, the antibody exhibits the property in mammals of increasing red blood cell count (number) or hemoglobin or hematocrit levels, and/or normalizing reticulocyte count, reticulocyte mean cell volume and/or reticulocyte hemoglobin content.

In various embodiments, the antibody binds to a fragment of ferroportin comprising at least five, ten, fifteen or more amino acids located within amino acids 393-449 of SEQ ID NO: 16, or an epitope within or of this fragment. In some embodiments, the antibody binds to an epitope of ferroportin that comprises at least one, two, three, four, five, six or more amino acids located within amino acids 439-449 of SEQ ID NO: 16. In some embodiments, the antibody binds to a fragment of ferroportin that comprises amino acids ANIVPETSPES (amino acids 439-449 of SEQ ID NO: 16), or an epitope within or of this fragment. Epitopes may be entirely within the fragment, or epitopes of the fragment may comprise one, two, three, four, five or six amino acids within the fragment and one or more amino acids outside the fragment. In some embodiments, the antibody binds to a fragment of ferroportin that comprises amino acids NIVPETSPES (amino acids 440-449 of SEQ ID NO: 16), or an epitope within or of this fragment. In some embodiments, the antibody binds to a fragment of ferroportin that comprises amino acids IVPETSPESV (amino acids 441-450 of SEQ ID NO: 16), or an epitope within or of this fragment. In some embodiments, the antibody binds to a fragment of ferroportin that comprises amino acids VPETSPESVP (amino acids 442-451 of SEQ ID NO: 16), or an epitope within or of this fragment. In some embodiments, the antibody binds to a fragment of ferroportin that comprises amino acids PETSPESVPI (amino acids 443-452 of SEQ ID NO: 16), or an epitope within or of this fragment. In some embodiments, the antibody binds to a fragment of ferroportin that comprises amino acids TSPESVPIIS (amino acids 445-454 of SEQ ID NO: 16), or an epitope within or of this fragment. In some embodiments, the antibody binds to a fragment of ferroportin that comprises amino acids ANIVPETSP (amino acids 439-447 of SEQ ID NO: 16), or an epitope within or of this fragment. In some embodiments, the antibody binds to a fragment of ferroportin that comprises amino acids IVPETSPES (amino acids 441-449 of SEQ ID NO: 16), or an epitope within or of this fragment. In some embodiments, the antibody binds to a fragment of ferroportin that comprises amino acids ANIVPETS (amino acids 439-446 of SEQ ID NO: 16), or an epitope within or of this fragment. In some embodiments, the antibody binds to a fragment of ferroportin that comprises amino acids IVPETSPE (amino acids 441-448 of SEQ ID NO: 16), or an epitope within or of this fragment. In some embodiments, the antibody binds to a fragment of ferroportin that comprises amino acids IVPETSP (amino acids 441-447 of SEQ ID NO: 16), or an epitope within or of this fragment. In some embodiments, the antibody binds to a fragment of ferroportin that comprises amino acids PETSPES (amino acids 443-449 of SEQ ID NO: 16), or an epitope within or of this fragment. In some embodiments, the antibody binds to a fragment of ferroportin that comprises amino acids LVELYGNSLL (amino acids 50-69 of SEQ ID NO: 16), or an epitope within or of this fragment. In some embodiments, the antibody binds to a fragment of ferroportin that comprises amino acids FLVELYGNSL (amino acids 49-68 of SEQ ID NO: 16), or an epitope within or of this fragment. In some embodiments, the antibody binds to a fragment of ferroportin that comprises amino acids VELYGNSLLL (amino acids 51-70 of SEQ ID NO: 16), or an epitope within or of this fragment. In some embodiments, the antibody binds to a fragment of ferroportin that comprises amino acids ELYGNSLLLT (amino acids 52-71 of SEQ ID NO: 16), or an epitope within or of this fragment. In some embodiments, the antibody binds to a fragment of ferroportin that comprises amino acids LYGNSLLLTA (amino acids 53-72 of SEQ ID NO: 16), or an epitope within or of this fragment. In some embodiments, the antibody binds to a fragment of ferroportin that comprises amino acids LAFLYMTVLG (amino acids 314-323 of SEQ ID NO: 16), or an epitope within or of this fragment. In some embodiments, the antibody binds to a fragment of ferroportin that comprises amino acids AFLYMTVLGF (amino acids 315-324 of SEQ ID NO: 16), or an epitope within or of this fragment. In some embodiments, the antibody binds to a fragment of ferroportin that comprises amino acids FLYMTVLGFD (amino acids 316-325 of SEQ ID NO: 16), or an epitope within or of this fragment. In some embodiments, the antibody binds to a fragment of ferroportin that comprises amino acids IQGESITPTKIPEIT (amino acids 413-427 of SEQ ID NO: 16), or an epitope within or of this fragment. In some embodiments, the antibody binds to a fragment of ferroportin that comprises amino acids IQGESITPTK (amino acids 413-422 of SEQ ID NO: 16), or an epitope within or of this fragment. In some embodiments, the antibody binds to a fragment of ferroportin that comprises amino acids QGESITPTKI (amino acids 414-423 of SEQ ID NO: 16), or an epitope within or of this fragment. In some embodiments, the antibody binds to a fragment of ferroportin that comprises amino acids GESITPTKIP (amino acids 415-424 of SEQ ID NO: 16), or an epitope within or of this fragment. In some embodiments, the antibody binds to a fragment of ferroportin that comprises amino acids ESITPTKIPE (amino acids 416-425 of SEQ ID NO: 16), or an epitope within or of this fragment. In some embodiments, the antibody binds to a fragment of ferroportin that comprises amino acids SITPTKIPEI (amino acids 417-426 of SEQ ID NO: 16), or an epitope within or of this fragment. In some embodiments, the antibody binds to a fragment of ferroportin that comprises amino acids ITPTKIPEIT (amino acids 418-427 of SEQ ID NO: 16), or an epitope within or of this fragment. In some embodiments, the antibody binds to a fragment of ferroportin that comprises amino acids DGWVSYYNQP (amino acids 297-306 of SEQ ID NO: 16), or an epitope within or of this fragment. In some embodiments, the antibody binds to a fragment of ferroportin that comprises amino acids ITTEIYMSNGSNS (amino acids 426-438 of SEQ ID NO: 16), or an epitope within or of this fragment. In some embodiments, the antibody binds to a fragment of ferroportin that comprises amino acids TEIYMSNGSNSA (amino acids 428-439 of SEQ ID NO: 16), or an epitope within or of this fragment. In some embodiments, the antibody binds to a fragment of ferroportin that comprises amino acids ITTEIYMSNG (amino acids 426-435 of SEQ ID NO: 16), or an epitope within or of this fragment. In some embodiments, the antibody binds to a fragment of ferroportin that comprises amino acids TTEIYMSNGS (amino acids 427-436 of SEQ ID NO: 16), or an epitope within or of this fragment. In some embodiments, the antibody binds to a fragment of ferroportin that comprises amino acids TEIYMSNGSN (amino acids 428-437 of SEQ ID NO: 16), or an epitope within or of this fragment. In some embodiments, the antibody binds to a fragment of ferroportin that comprises amino acids EIYMSNGSNS (amino acids 429-438 of SEQ ID NO: 16), or an epitope within or of this fragment. In some embodiments, the antibody binds to a fragment of ferroportin that comprises amino acids IYMSNGSNSA (amino acids 430-439 of SEQ ID NO: 16), or an epitope within or of this fragment. In some embodiments, the antibody binds to a fragment of ferroportin that comprises amino acids YHGWVLTSCY (amino acids 124-133 of SEQ ID NO: 16), or an epitope within or of this fragment. In some embodiments, the antibody binds to a fragment of ferroportin that comprises amino acids RDGWVSYYNQ (amino acids 296-305 of SEQ ID NO: 16), or an epitope within or of this fragment. In some embodiments, the antibody binds to a fragment of ferroportin that comprises amino acids EIYMSNG (amino acids 429-435 of SEQ ID NO; 16), or an epitope within or of this fragment. In some embodiments, the antibody binds to a fragment of ferroportin that comprises amino acids IYMSNGSN (amino acids 430-437 of SEQ ID NO: 16), or an epitope within or of this fragment. In some embodiments, the antibody binds to a fragment of ferroportin that comprises amino acids ITPTK (amino acids 418-422 of SEQ ID NO: 16), or an epitope within or of this fragment.

In various embodiments monoclonal antibodies can include any of antibodies 31A5, 37A2, 37B9, 37C8, 37G8, 38A4, 38C8, 38D2, 38E3 and 38G6 or antibodies that retain any one, two, three, four, five, or six of CDRH1, CDRH2, CDRH3, CDRL1, CDRL2 or CDRL3 of such antibodies, optionally including one or two mutations in such CDR(s), or antibodies that retain a light or heavy chain variable region of any of such antibodies, or antibodies that retain all heavy chain CDRs and/or all light chain CDRs of any of such antibodies, or antibodies that bind to the same epitope on human ferroportin as antibodies 31A5, 37A2, 37B9, 37C8, 37G8, 38A4, 38C8, 38D2, 38E3 and 38G6, or that compete with such antibodies for binding to human ferroportin by at least 75%.

Various embodiments also provide nucleic acids encoding any of the monoclonal antibodies described herein, vectors comprising such nucleic acid sequences, and host cells comprising such nucleic acids or vectors. In a related aspect, methods for recombinant production of such monoclonal antibodies are provided which include culturing the aforementioned host cell such that the nucleic acid is expressed to produce the antibody, and optionally recovering the antibody from the host cell or culture medium. In a related embodiment, an isolated antibody or agent produced by the aforementioned method is provided. Such antibodies are optionally conjugated to additional therapeutic, cytotoxic, or diagnostic moieties.

In some embodiments, the anti-ferroportin antibodies are produced by (a) administering to a mammal a nucleic acid encoding ferroportin (SEQ ID NO: 16), optionally (b) administering to said mammal the same or a different nucleic acid nucleic acid encoding ferroportin (SEQ ID NO: 16), optionally (c) administering to said mammal a composition comprising cell membrane expressing ferroportin, and (d) obtaining cells expressing antibody from said mammal.

In another aspect, a method is provided of detecting human ferroportin in a sample, comprising contacting a sample from a human with any of the aforementioned antibodies under conditions that allow binding of the antibody to human ferroportin, and detecting the bound antibody. In one embodiment, a first antibody to ferroportin is immobilized on a solid support, as a capture reagent, and a second antibody to ferroportin is used as a detection reagent. In a related aspect, the amount of ferroportin in the sample is quantitated by measuring the amount of the bound antibody.

In another aspect, pharmaceutical compositions are provided comprising a therapeutically effective amount of any of the antibodies described herein and a pharmaceutically acceptable carrier, diluent or excipient. Also provided is the use of such antibodies in preparation of a medicament for treatment of a human with a disorder of iron homeostasis, including but not limited to an elevated level of hepcidin, a hepcidin-related disorder, or anemia. It is understood that co-administration methods involving administration of antibodies with a second therapeutic agent, as described herein, encompass not only the use of the antibody in preparation of a medicament for co-administration with the second therapeutic agent, but also the use of the second therapeutic agent in preparation of a medicament for co-administration with the antibody.

Various embodiments further provide methods of using such antibodies, for example, to treat a mammal with a disorder of iron homeostasis, or a hepcidin-related disorder, or, or a mammal with anemia, by administering a therapeutically effective amount of such antibody. In exemplary embodiments, the mammal is a human suffering from a condition selected from the group consisting of African iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, cirrhosis of liver, classic hemochromatosis, collagen-induced arthritis (CIA), conditions with hepcidin excess (elevated hepcidin), congenital dyserythropoietic anemia, congestive heart failure, Crohn's disease, diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, gracile syndrome, H. pyelori infection or other bacterial infections, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hereditary hemochromatosis, HIV or other viral illnesses, Huntington's disease, hyperferritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, osteoarthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, Wilson's disease and/or cardiac disorders associated with iron overload.

In yet another aspect, methods are provided for treating a mammal with a disorder of iron homeostasis by administration of (a) an aforementioned anti-ferroportin antibody or specific binding agent; and (b) an erythropoiesis stimulator, in therapeutically effective amounts. Exemplary erythropoiesis stimulators include erythropoietin, erythropoietin agonist variants, and peptides or antibodies that bind and activate erythropoietin receptor. Erythropoiesis stimulators include, but are not limited to, epoetin alfa, epoetin beta, epoetin delta, epoetin omega, epoetin iota, epoetin zeta, and analogs thereof, mimetic peptides, mimetic antibodies and HIF inhibitors (see U.S. Patent Publication No. 2005/0020487, the disclosure of which is incorporated by reference in its entirety). In particular, erythropoietin includes, but is not limited to, erythropoietin as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; 7,217,689; PCT publication nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and US publication nos. US 2002/0155998; US 2003/0077753; US 2003/0082749; US 2003/0143202; US 2004/0009902; US 2004/0071694; US 2004/0091961; US 2004/0143857; US 2004/0157293; US 2004/0175379; US 2004/0175824; US 2004/0229318; US 2004/0248815; US 2004/0266690; US 2005/0019914; US 2005/0026834; US 2005/0096461; US 2005/0107297; US 2005/0107591; US 2005/0124045; US 2005/0124564; US 2005/0137329; US 2005/0142642; US 2005/0143292; US 2005/0153879; US 2005/0158822; US 2005/0158832; US 2005/0170457; US 2005/0181359; US 2005/0181482; US 2005/0192211; US 2005/0202538; US 2005/0227289; US 2005/0244409; US 2006/0088906; and US 2006/0111279. In certain exemplary embodiments, the erythropoiesis stimulator is selected from the group consisting of human erythropoietin (SEQ ID NO: 21) and darbepoetin alfa (SEQ ID NO: 22). Exemplary forms of anemia that may be treated according to such methods include anemia of inflammation, anemia of cancer, chemotherapy induced anemia, iron deficiency anemia, a disorder of iron homeostasis, ferroportin disease, or anemia resulting from kidney disease. Also provided are methods of treating a mammal with anemia that is hypo-responsive, or even resistant, to therapy with an erythropoiesis stimulator, comprising administering a therapeutically effective amount of an anti-ferroportin antibody or specific binding agent.

In another related aspect, kits for treating a disorder of iron homeostasis, or a disorder associated with elevated hepcidin levels, or a hepcidin-related disorder, or a disorder of iron homeostasis, or a mammal with anemia, are also provided. In one exemplary embodiment, the kit includes (a) an anti-ferroportin antibody or specific binding agent, and (b) an erythropoiesis stimulator, and optionally, iron or an iron chelator. In another exemplary embodiment, the kit includes an anti-ferroportin antibody or specific binding agent, and a label attached to or packaged with the container, the label describing use of the anti-ferroportin antibody or specific binding agent, with an erythropoiesis stimulator. In yet another exemplary embodiment, the kit includes an erythropoiesis stimulator and a label attached to or packaged with the container, the label describing use of the erythropoiesis stimulator with an anti-ferroportin antibody or specific binding agent. Also provided is the use of an anti-ferroportin antibody or specific binding agent in the preparation of a medicament for administration with an erythropoiesis stimulator, as well as use of an erythropoiesis stimulator in the preparation of a medicament for administration with an anti-ferroportin antibody or specific binding agent. In any of these kits or uses, an anti-ferroportin antibody or specific binding agent and the erythropoiesis stimulator can be in separate vials or can be combined together in a single pharmaceutical composition. In yet another embodiment, the anti-ferroportin antibody or specific binding agent the erythropoiesis stimulator, or both, can be combined with iron or an iron chelator in a single pharmaceutical composition or can be in separate vials.

Also provided is a method of selecting a treatment regimen for a subject in need of treatment comprising (a) screening the subject for a decreased level of circulating iron or an elevated level of hepcidin; (b) prescribing to said subject any of the aforementioned antibodies and optionally prescribing an erythropoiesis stimulator and/or iron and/or iron chelator to said subject. In some embodiments, the screening comprises obtaining a biological sample and determining the level of iron or hepcidin in said sample.

Various embodiments provide combination therapies for the treatment of a disorder of iron homeostasis or iron overload. In some embodiments, the combination therapy comprises administering to a subject in need of treatment an anti-ferroportin antibody or specific binding agent and an erythropoiesis stimulator in therapeutically-effective amounts. In some embodiments, the combination therapy comprises administering to a subject in need of treatment an anti-ferroportin antibody or specific binding agent and iron in therapeutically-effective amounts. In some embodiments, the combination therapy comprises administering to a subject in need of treatment, e.g. suffering from iron overload, an anti-ferroportin antibody or specific binding agent and an iron chelator in therapeutically-effective amounts. In some embodiments, the combination therapy comprises administering to a subject in need of treatment an anti-ferroportin antibody or specific binding agent and an anti-hepcidin antibody in therapeutically-effective amounts. In some embodiments, the anti-ferroportin antibody or specific binding agent and other agent in the combination therapy are formulated into one composition. In some embodiments, the anti-ferroportin antibody or specific binding agent and other agent in the combination therapy are formulated into separate compositions.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention can include, as an additional aspect, all embodiments of the invention narrower in scope in any way than the variations defined by specific paragraphs herein. For example, certain aspects of the invention that are described as a genus, and it should be understood that every member of a genus can be, individually, an aspect of the invention. Also, aspects described as a genus or selecting a member of a genus, should be understood to embrace combinations of two or more members of the genus.

It should be understood that while various embodiments in the specification are presented using "comprising" language, under various circumstances, a related embodiment may also be described using "consisting of" or "consisting essentially of" language. It is to be noted that the term "a" or "an", refers to one or more, for example, "an immunoglobulin molecule," is understood to represent one or more immunoglobulin molecules. As such, the terms "a" (or "an"), "one or more," and "at least one" can be used interchangeably herein.

It should also be understood that when describing a range of values, the characteristic being described could be an individual value found within the range. For example, "a pH from about pH 4 to about pH 6," could be, but is not limited to, pH 4, 4.2, 4.6, 5.1 5.5 etc. and any value in between such values. Additionally, "a pH from about pH 4 to about pH 6," should not be construed to mean that the pH of a formulation in question varies 2 pH units in the range from pH 4 to pH 6 during storage, but rather a value may be picked in that range for the pH of the solution, and the pH remains buffered at about that pH. In some embodiments, when the term "about" is used, it means the recited number plus or minus 5%, 10%, 15% or more of that recited number. The actual variation intended is determinable from the context. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE FIGURES

FIG. 6 provides the heavy chain CDRs for antibodies 37A2 (SEQ ID NOs: 32-34), 37B9 (SEQ ID NOs: 42-44), 37C8 (SEQ ID NOs: 52-54), 37G8 (SEQ ID NOs: 62-64), 38A4 (SEQ ID NOs: 72-74), 38C8 (SEQ ID NOs: 82-84), 38D2 (SEQ ID NOs: 92-94), 38E3 (SEQ ID NOs: 102-104) and 38G6 (SEQ ID NOs: 112-114).

FIG. 7 provides the light chain CDRs for antibodies 37A2 (SEQ ID NOs: 29-31), 37B9 (SEQ ID NOs: 39-41), 37C8 (SEQ ID NOs: 49-51), 37G8 (SEQ ID NOs: 59-61), 38A4 (SEQ ID NOs: 69-71), 38C8 (SEQ ID NOs: 79-81), 38D2 (SEQ ID NOs: 89-91), 38E3 (SEQ ID NOs: 99-101) and 38G6 (SEQ ID NOs: 109-111).

FIG. 8A provides the cDNA and amino acid sequences of the heavy and light variable regions of antibodies 38G6 and 38E3.

FIG. 8B provides the cDNA and amino acid sequences of the heavy and light variable regions of antibodies 38D2 and 38C8.

FIG. 8C provides the cDNA and amino acid sequences of the heavy and light variable regions of antibodies 38A4 and 37G8.

FIG. 8D provides the cDNA and amino acid sequences of the heavy and light variable regions of antibodies 37C8 and 37B9.

FIG. 8E provides the cDNA and amino acid sequences of the heavy and light variable regions of antibody 37A2.

FIG. 9 demonstrates that functional and non-functional anti-ferroportin antibodies recognize similar epitopes on ferroportin.

DETAILED DESCRIPTION

Figure 1:
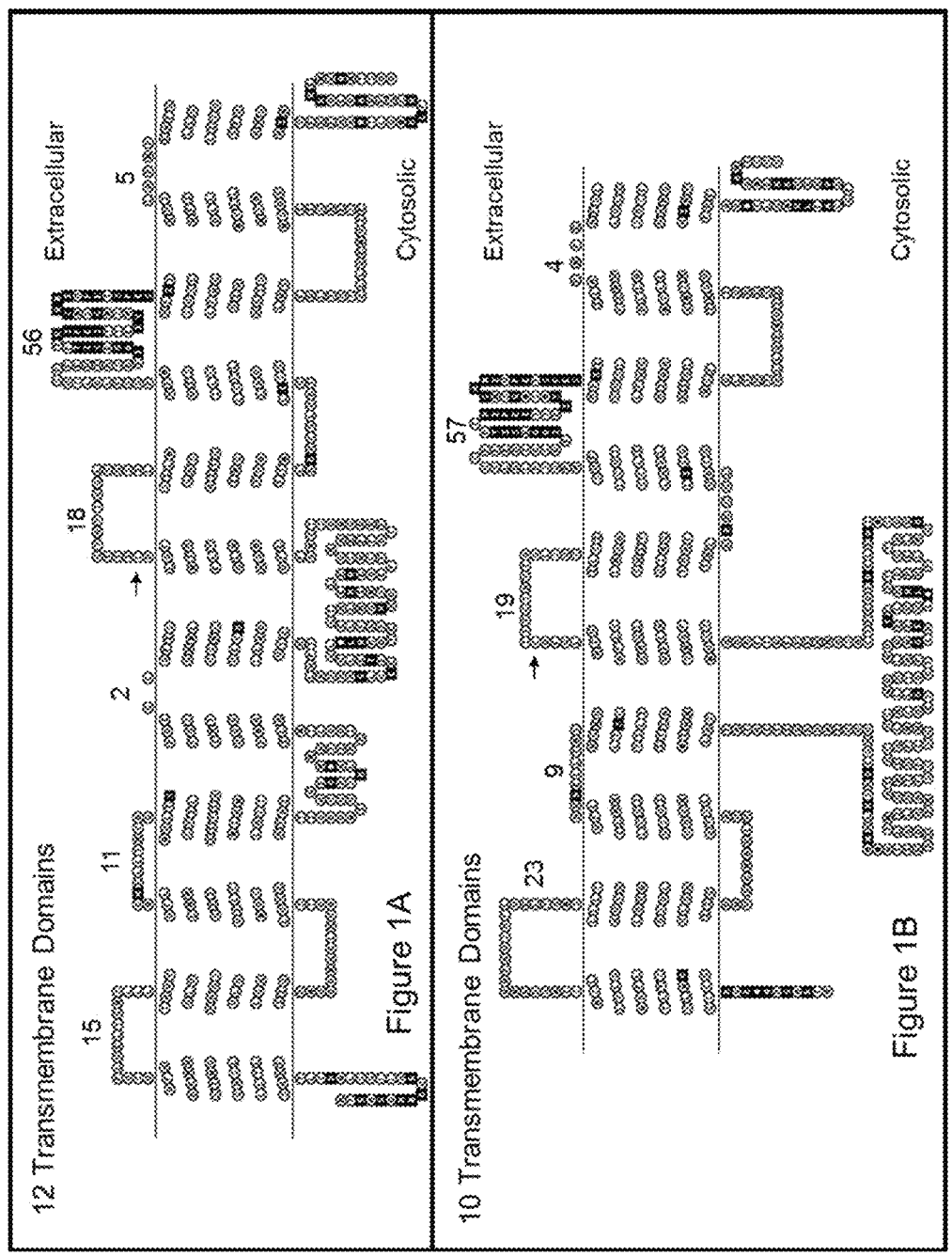
FIGS. 1A and 1B show two schematic depictions of the ferroportin transmembrane and extracellular domains.

Ferroportin (SEQ ID NO: 16) is a multi-transmembrane protein predicted to have either ten or twelve transmembrane domains. Based on topology diagrams, fewer than 20% of the residues are predicted to be extracellular, and the longest extracellular loop is predicted to be only 57 residues long. FIG. 1 shows two schematic depictions of the ferroportin transmembrane and extracellular domains. In FIG. 1A, the extracellular domains correspond to amino acids 46-60 (loop 1), 116-126 (loop 2), 204-205 and 325-342 (loop 3), 394-449 (loop 4) and 513-517 (loop 5) of SEQ ID NO: 16. In FIG. 1B, the extracellular domains correspond to amino acids 35-57 (loop 1), 116-124 (loop 2), 332-340 (loop 3), 393-449 (loop 4) and 515-518 (loop 5) of SEQ ID NO: 16.

Embodiments of the invention provide monoclonal antibodies that bind to ferroportin, or loops 1, 2, 3 and 4 of ferroportin (as depicted in FIG. 1A or 1B), or fragments thereof, with high affinity. Other embodiments of the invention provide antibodies, such as monoclonal antibodies, that can preserve ferroportin activity and increase circulating iron levels, either in subjects with normal iron homeostasis or in subjects at risk of or suffering from disorders of iron homeostasis, including disorders arising from elevated levels of hepcidin. In some embodiments, the antibodies disclosed herein inhibit the effects of hepcidin on ferroportin surface expression. In some embodiments, the antibodies disclosed herein prevent internalization and degradation of ferroportin, including hepcidin-mediated degradation of ferroportin, thereby maintaining iron homeostasis.

I. Anti-Ferroportin Antibodies and Specific Binding Agents

The term "antibody" is used in the broadest sense and includes fully assembled antibodies, monoclonal antibodies, polyclonal antibodies, multispecific antibodies (including bispecific antibodies), antibody fragments that can bind an antigen (including, Fab', F'(ab)$_2$, Fv, single chain antibodies, diabodies), and recombinant peptides comprising the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity.

In some embodiments, the antibodies exhibit desirable characteristics such as binding affinity as measured by $K_D$ (equilibrium dissociation constant) for ferroportin in the range of $1 \times 10^{-6}$ M or less, or ranging down to $10^{-16}$ M or lower, (e.g., about $10^{-7}$, $10^{-8}$, $10^{-9}$, $10^{-10}$, $10^{-11}$, $10^{-12}$, $10^{-13}$, $10^{-14}$, $10^{-15}$, $10^{-16}$ M or less). Higher or better affinity is characterized by a lower $K_D$. An estimate of the equilibrium dissociation constant can be determined by monitoring antibody binding to ferroportin-expressing cells over a range of antibody concentrations. To determine antibody binding affinity, a HEK 293 cell line engineered to inducibly express human ferroportin is plated at 50,000 cells per well of a 96-well black-walled, clear-bottom poly-D-lysine coated plate (Becton-Dickinson, Franklin Lakes N.J.) plate and induced, using a 10 μg/mL final concentration of doxycycline in a Tet-inducible system, to express ferroportin in the presence of ferric citrate. Upon removal of the induction reagent the cells' medium is then replaced with increasing amounts of antibody in cold DMEM 10% FBS 1× penicillin/streptomycin/glutamine and incubated for 30 minutes at 4° C. After this, the cells are gently washed four times with 200 μL/well cold PBS and incubated with a saturating concentration (5 μg/mL) of an anti-mouse H+L AlexaFluor 488 conjugate (Invitrogen Inc, Carlsbad Calif.) and incubated in the dark for 30 minutes at 4° C. Once this is completed the cells are then washed four times with 200 µL/well cold PBS, left in 100 µL/well cold PBS, and read immediately for relative fluorescence intensity on a fluorimeter such as a Perkin-Elmer Envision (Perkin-Elmer, Waltham Mass.). From the fluorescence intensity data, a binding curve is then established, the $EC_{50}$ of which then represents an approximate $K_D$.

In other embodiments, the antibodies exhibit specificity for ferroportin. As used herein, an antibody is "specific for" or "specifically binds" human ferroportin when it has a significantly higher binding affinity for, and consequently is capable of distinguishing, human ferroportin compared to other unrelated proteins in different families. In some embodiments, such antibodies may also cross-react with ferroportin of other species, such as mouse, rat, or primate ferroportin; while in other embodiments, the antibodies bind only to human or primate ferroportin and not significantly to rodent ferroportin.

In yet other embodiments, the antibodies are capable of promoting ferroportin preservation. "Ferroportin preservation" or "preservation of ferroportin activity" as used herein refers to the ability to increase or maintain iron efflux regulated by ferroportin and can be detected as a relatively increased level of iron efflux in the presence of the antibody that promotes ferroportin preservation, compared to the level of iron efflux in the absence of that antibody. For example, in the presence of an antibody that promotes ferroportin preservation, iron efflux may be increased, intracellular iron levels may be decreased, and/or circulating iron levels may be increased. In some embodiments, ferroportin preservation can occur in normal cells and normal subjects. In other embodiments, ferroportin preservation can occur in the presence of molecules, e.g., hepcidin, that would otherwise alter iron efflux regulated by ferroportin. In some embodiments, ferroportin preservation occurs in the presence of an amount of human hepcidin effective to degrade ferroportin by 100% or about 99%, or about 98%, or about 97%, or about 96%, or about 95% or about 94%, or about 93%, or about 92%, or about 91%, or about 90%, or about 85%, or about 80%, or about 75% or lower. In some embodiments, ferroportin preservation can occur in cells or subjects having a disorder of iron homeostasis. In some embodiments, the antibody decreases intracellular iron concentration and/or increases circulating iron concentration at an $EC_{50}$ of about $10^{-6}$ M or less, or about $10^{-7}$ M or less, or about $10^{-8}$ M or less, or about $10^{-9}$ M or less. The ability of antibodies to preserve ferroportin activity and/or maintain iron efflux can be detected by assays such as those set forth in Example 3. In various embodiments, in the presence of hepcidin, the antibody decreases intracellular iron concentration and/or increases circulating iron concentration at an $IC_{50}$ of about $10^{-6}$ M or less, or about $10^{-7}$ M or less, or about $10^{-8}$ M or less, or about $10^{-9}$ M or less In some embodiments, antibodies are provided that inhibit (or neutralize) internalization and/or degradation of ferroportin, including hepcidin-dependent internalization and/or degradation, in vitro and preferably also in vivo. The ability of antibodies to inhibit ferroportin internalization and/or degradation can be detected by assays such as those set forth in Example 6. In exemplary aspects, the monoclonal antibodies inhibit (or neutralize) the degradation of ferroportin that occurs in response to high iron levels (and/or inflammation). In some embodiments, the binding of hepcidin to ferroportin is not inhibited by the ferroportin-preserving antibodies disclosed herein.

Anti-ferroportin antibodies capable of ferroportin preservation are therapeutically useful for disorders of iron homeostasis and are expected to increase serum iron levels and/or improve red blood cell number or characteristics as measured through one or more markers, for example, ferritin/iron levels, red blood cell count, red blood cell characteristics (hemoglobin content and/or cell volume), early red blood cell characteristics (reticulocyte numbers, hemoglobin content or cell volume) (Clinical Hematology, third edition, Lippincott, Williams and Wilkins; editor Mary L. Turgeon, 1999), or iron transport.

In specific exemplary embodiments, the invention contemplates:

1) a monoclonal antibody that retains any one, two, three, four, five, or six of CDRH1, CDRH2, CDRH3, CDRL1, CDRL2 or CDRL3 of antibodies 31A5, 37A2, 37B9, 37C8, 37G8, 38A4, 38C8, 38D2, 38E3 and 38G6, optionally including one or two mutations in such CDR(s);

2) a monoclonal antibody that retains all of CDRH1, CDRH2, CDRH3, or the heavy chain variable region of antibodies 31A5, 37A2, 37B9, 37C8, 37G8, 38A4, 38C8, 38D2, 38E3 and 38G6, optionally including one or two mutations in such CDR(s);

3) a monoclonal antibody that retains all of CDRL1, CDRL2, CDRL3, or the light chain variable region of antibodies 31A5, 37A2, 37B9, 37C8, 37G8, 38A4, 38C8, 38D2, 38E3 and 38G6, optionally including one or two mutations in such CDR(s), 4) a monoclonal antibody that binds to the same linear or three-dimensional epitope of ferroportin as antibodies 31A5, 37A2, 37B9, 37C8, 37G8, 38A4, 38C8, 38D2, 38E3 and 38G6, e.g. as determined through X-ray crystallography or other biophysical or biochemical techniques such as deuterium exchange mass spectrometry, alanine scanning and peptide fragment ELISA, 5) a monoclonal antibody that binds to a peptide consisting of amino acid residues 393-446 of ferroportin (SEQ ID NO: 16), and in some embodiments that does not bind to amino acid residues 75-96, 152-183, 330-338 or 542-571 of SEQ ID NO: 16, 6) a monoclonal antibody that binds to a peptide consisting of amino acid residues 439-449 of ferroportin (SEQ ID NO: 16), and 7) a monoclonal antibody that competes with any one of antibodies 31A5, 37A2, 37B9, 37C8, 37G8, 38A4, 38C8, 38D2, 38E3 and 38G6 for binding to human ferroportin by more than about 75%, more than about 80%, or more than about 81%, 82%, 83%, 84%, 85%, 86%, 87%, 88%, 89%, 90%, 91%, 92%, 93%, 94% or 95%.

In one embodiment, the antibody comprises at least one, two, three, four, five or all of the amino acid sequences selected from the group consisting of SEQ ID NOs: 5-10 (31A5 CDRs). In another embodiment, the antibody comprises at least one, two, three, four, five or all of the amino acid sequences selected from the group consisting of SEQ ID NOs: 29-34 (37A2 CDRs). In another embodiment, the antibody comprises at least one, two, three, four, five or all of the amino acid sequences selected from the group consisting of SEQ ID NOs: 39-44 (37B9 CDRs). In yet another embodiment, the antibody comprises at least one, two, three, four, five or all of the amino acid sequences selected from the group consisting of SEQ ID NOs: 49-54 (37C8 CDRs). In another embodiment, the antibody comprises at least one, two, three, four, five or all of the amino acid sequences selected from the group consisting of SEQ ID NOs: 59-64 (37G8 CDRs). In another embodiment, the antibody comprises at least one, two, three, four, five or all of the amino acid sequences selected from the group consisting of SEQ ID NOs: 69-74 (38A4 CDRs). In another embodiment, the antibody comprises at least one, two, three, four, five or all of the amino acid sequences selected from the group consisting of SEQ ID NOs: 79-84 (38C8 CDRs). In another embodiment, the antibody comprises at least one, two, three, four, five or all of the amino acid sequences selected from the group consisting of SEQ ID NOs: 89-94 (38D2 CDRs). In another embodiment, the antibody comprises at least one, two, three, four, five or all of the amino acid sequences selected from the group consisting of SEQ ID NOs: 99-104 (38E3 CDRs). In yet another embodiment, the antibody comprises at least one, two, three, four, five or all of the amino acid sequences selected from the group consisting of SEQ ID NOs: 109-114 (38G6 CDRs).

In some embodiments, the antibody comprises all three light chain CDRs, all three heavy chain CDRs, or all six CDRs. In some exemplary embodiments, two light chain CDRs from an antibody may be combined with a third light chain CDR from a different antibody. Alternatively, a CDRL1 from one antibody can be combined with a CDRL2 from a different antibody and a CDRL3 from yet another antibody, particularly where the CDRs are highly homologous. Similarly, two heavy chain CDRs from an antibody may be combined with a third heavy chain CDR from a different antibody; or a CDRH1 from one antibody can be combined with a CDRH2 from a different antibody and a CDRH3 from yet another antibody, particularly where the CDRs are highly homologous. FIG. 6 provides the heavy chain CDRs for antibodies 37A2 (SEQ ID NOs: 32-34), 37B9 (SEQ ID NOs: 42-44), 37C8 (SEQ ID NOs: 52-54), 37G8 (SEQ ID NOs: 62-64), 38A4 (SEQ ID NOs: 72-74), 38C8 (SEQ ID NOs: 82-84), 38D2 (SEQ ID NOs: 92-94), 38E3 (SEQ ID NOs: 102-104) and 38G6 (SEQ ID NOs: 112-114). FIG. 7 provides the light chain CDRs for antibodies 37A2 (SEQ ID NOs: 29-31), 37B9 (SEQ ID NOs: 39-41), 37C8 (SEQ ID NOs: 49-51), 37G8 (SEQ ID NOs: 59-61), 38A4 (SEQ ID NOs: 69-71), 38C8 (SEQ ID NOs: 79-81), 38D2 (SEQ ID NOs: 89-91), 38E3 (SEQ ID NOs: 99-101) and 38G6 (SEQ ID NOs: 109-111).

Consensus CDRs may also be used. In one embodiment, the antibody comprises one or more of the amino acid sequences selected from the group consisting of SEQ ID NO: 42 (GYYMH, heavy chain CDR1 from antibodies 37B9, 37C8, 37G8, 38C8 and 38E3), SEQ ID NO: 115 (GYXMH, heavy chain CDR1 consensus from 37A2, 37B9, 37C8, 37G8, 38C8, and 38E3), SEQ ID NO: 116 (GYYXH, heavy chain CDR1 consensus from 37B9, 37C8, 37G8, 38C8, 38D2 and 38E3), SEQ ID NO: 117 (WINPHTGGKNYXQXFQG, heavy chain CDR2 consensus for antibodies 37B9, 37C8, 37G8, 38C8 and 38E3), SEQ ID NO: 118 (DPSXXVXGPSFYYXGLDV, heavy chain CDR3 consensus for antibodies 37B9, 37C8, 37G8, 38C8 and 38E3), SEQ ID NO: 119 (KISNRXS, light chain CDR2 consensus for antibodies 37B9, 37C8, 37G8, 38C8 and 38E3): wherein X is any amino acid.

In various embodiments, the antibody comprises WINPHTGGKNYX$_1$QX$_2$FQG (SEQ ID NO:136), wherein X$_1$ and X$_2$ is any amino acid; or X$_1$ and X$_2$ is A, G, K, or R, any combination thereof, or conservative substitution thereof; or X$_1$ is A or G or conservative substitution thereof, and X$_2$ is any amino acid; or X$_1$ is any amino acid and X$_2$ is K or R or conservative substitution thereof, or X$_1$ is A or G or conservative substitution thereof and X$_2$ is K or R or conservative substitution thereof.

In various other embodiments, the antibody comprises the amino acid sequence WINPHTGGKNYX$_1$QX$_2$FQG (SEQ ID NO:136), wherein X$_1$ and X$_2$ is A, G, K, R, any combination thereof, or conservative substitution thereof; and the amino acid sequence DPSX$_1$X$_2$VX$_3$GPSFYYX$_4$GLDV (SEQ ID NO:137), wherein X$_1$, X$_2$, X$_3$ and X$_4$ is A, F, I, L, V, S, T, Y any combination thereof, or conservative substitution thereof.

In various embodiments, the antibody comprises the amino acid sequence DPSX$_1$X$_2$VX$_3$GPSFYYX$_4$GLDV (SEQ ID NO:137), wherein X$_1$, X$_2$, X$_3$ and X$_4$ is any amino acid; or X$_1$, X$_2$, X$_3$ and X$_4$ is A, F, I, L, V, S, T, Y, any combination thereof, or conservative substitution thereof; or X$_1$ is I or L or conservative substitution thereof and X$_2$, X$_3$ and X$_4$ is any amino acid; or X$_2$ is A, V, or S or conservative substitution thereof and X$_1$, X$_3$ and X$_4$ is any amino acid; or X$_3$ is A or T or conservative substitution thereof and X$_1$, X$_2$ and X$_4$ is any amino acid; or X$_4$ is Y or F or conservative substitution thereof and X$_1$, X$_2$ and X$_3$ is any amino acid; or X$_1$ is I or L or conservative substitution thereof, X$_2$ is A V or S or conservative substitution thereof, and X$_3$ and X$_4$ is any amino acid; or X$_1$ is any amino acid, X$_2$ is A, V or S or conservative substitution thereof, X$_3$ is A or T or conservative substitution thereof and X$_4$ is any amino acid; or X$_1$ and X$_2$ is any amino acid, X$_3$ is A or T or conservative substitution thereof and X$_4$ is Y or F or conservative substitution thereof; or X$_1$, X$_2$ and X3 is any amino acid, and X$_4$ is Y or F or conservative substitution thereof; or X$_1$ is I or L or conservative substitution thereof, X$_2$ is A, V, or S or conservative substitution thereof, X$_3$ is A or T or conservative substitution thereof and X$_4$ is Y or F or conservative substitution thereof; X$_2$ and X$_3$ is any amino acid, X$_1$ is I or L or conservative substitution thereof and X$_4$ is Y or F or conservative substitution thereof; or X$_1$ and X$_2$ is any amino acid, X$_3$ is A or T or conservative substitution thereof and X$_4$ is Y or F or conservative substitution thereof; or X$_1$ and X$_3$ is any amino acid, X$_2$ is A, V or S or conservative substitution thereof and X$_4$ is Y or F or conservative substitution thereof; or X$_1$ and X$_4$ is any amino acid, X$_2$ is A, V or S or conservative substitution thereof and X$_3$ is A or T or conservative substitution thereof; or X$_1$, X$_2$, and X$_3$ is any amino acid and X$_4$ is Y or F or conservative substitution thereof; or X$_1$, X$_2$, and X$_4$ is any amino acid and X$_3$ is A or T or conservative substitution thereof; or X$_1$, X$_3$, and X$_4$ is any amino acid and X$_2$ is A, V, or S or conservative substitution thereof, or X$_2$, X$_3$, and X$_4$ is any amino acid and X$_1$ is I or L or conservative substitution thereof; or X$_1$ is I or L or conservative substitution thereof, X$_2$ is any amino acid, X$_3$ is A or T or conservative substitution thereof and X$_4$ is any amino acid.

Any one of the consensus CDRs disclosed herein may be combined with two other CDRs from the same chain (e.g. heavy or light) of any of antibodies, e.g. to form a suitable heavy or light chain variable region.

In yet another embodiment, the antibody comprises the heavy and/or light chain variable region of antibody 31A5, e.g., SEQ ID NO: 4 (31A5 heavy chain variable region), and/or SEQ ID NO: 2 (31A5 light chain variable region). In another embodiment, the antibody comprises the heavy and/or light chain variable region of antibody 37A2, e.g., SEQ ID NO: 28 (37A2 heavy chain variable region) and/or SEQ ID NO: 26 (37A2 light chain variable region). In another embodiment, the antibody comprises the heavy and/or light chain variable region of antibody 37B9, e.g., SEQ ID NO: 38 (37B9 heavy chain variable region) and/or SEQ ID NO: 36 (37B9 light chain variable region). In another embodiment, the antibody comprises the heavy and/or light chain variable region of antibody 37C8, e.g., SEQ ID NO: 48 (37C8 heavy chain variable region) and/or SEQ ID NO: 46 (37C8 light chain variable region). In another embodiment, the antibody comprises the heavy and/or light chain variable region of antibody 37G8, e.g., SEQ ID NO: 58 (37G8 heavy chain variable region) and/or SEQ ID NO: 56 (37G8 light chain variable region). In another embodiment, the antibody comprises the heavy and/or light chain variable region of antibody 38A4, e.g., SEQ ID NO: 68 (38A4 heavy chain variable region) and/or SEQ ID NO: 66 (38A4 light chain variable region). In another embodiment, the antibody comprises the heavy and/or light chain variable region of antibody 38C8, e.g., SEQ ID NO: 78 (38C8 heavy chain variable region) and/or SEQ ID NO: 76 (38C8 light chain variable region). In yet another embodiment, the antibody comprises the heavy and/or light chain variable region of antibody 38D2, e.g., SEQ ID NO: 88 (38D2 heavy chain variable region) and/or SEQ ID NO: 86 (38D2 light chain variable region). In another embodiment, the antibody comprises the heavy and/or light chain variable region of antibody 38E3, e.g., SEQ ID NO: 98 (38E3 heavy chain variable region) and/or SEQ ID NO: 96 (38E3 light chain variable region). In another embodiment, the antibody comprises the heavy and/or light chain variable region of antibody 38G6, e.g., SEQ ID NO: 108 (38G6 heavy chain variable region) and/or SEQ ID NO: 106 (38G6 light chain variable region).

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to an amino acid sequence selected from the group consisting of SEQ ID NOs: 4 (31A5 heavy chain variable region), 2 (31A5 light chain variable region, 28 (37A2 heavy chain variable region), 26 (37A2 light chain variable region), 38 (37B9 heavy chain variable region), 36 (37B9 light chain variable region), 48 (37C8 heavy chain variable region), 46 (37C8 light chain variable region), 58 (37G8 heavy chain variable region), 56 (37G8 light chain variable region), 68 (38A4 heavy chain variable region), 66 (38A4 light chain variable region), 78 (38C8 heavy chain variable region), 76 (38C8 light chain variable region), 88 (38D2 heavy chain variable region), 86 (38D2 light chain variable region), 98 (38E3 heavy chain variable region), 96 (38E3 light chain variable region), 108 (38G6 heavy chain variable region) and 106 (38G6 light chain variable region), the polypeptide further comprising at least one, two, three, four, five or more of the amino acid sequences set forth in SEQ ID NOs: 5-10 (31A5 CDRs), 29-34 (37A2), 39-44 (37B9), 49-54 (37C8), 59-64 (37G8), 69-74 (38A4), 79-84 (38C8), 89-94 (38D2), 99-104 (38E3), and 109-114 (38G6). In some embodiments, the polypeptide with percentage identity to the light chain variable region may comprise one, two or three of the light chain CDRs. In other embodiments, the polypeptide with percentage identity to the heavy chain variable region may comprise one, two, or three of the heavy chain CDRs. In any of the foregoing embodiments, the polypeptide can include a sequence comprising one or two modifications to any of the amino acid sequences set forth in SEQ ID NOs: 5-10 (31A5 CDRs), 29-34 (37A2), 39-44 (37B9), 49-54 (37C8), 59-64 (37G8), 69-74 (38A4), 79-84 (38C8), 89-94 (38D2), 99-104 (38E3), and 109-114 (38G6).

Also contemplated is an antibody that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to heavy and light chain variable regions of an antibody selected from the group consisting of 34G3, 37A2, 37B9, 37C8, 37G8, 38A4, 38C8, 38D2, 38D6, 38E3 and 38G6 is specifically contemplated. the polypeptide further comprising at least one or more of the CDRs selected from the group consisting of 31A5 CDRs, 37A2 CDRs, 37B9 CDRs, 37C8 CDRs), 37G8 CDRs), 38A4 CDRs, 38C8 CDRs, 38D2 CDRs, 38E3 CDRs and 38G6 CDRs. In any of the foregoing embodiments, the polypeptide includes a sequence comprising one or two modifications to a CDR selected from the group consisting of 31A5 CDRs, 37A2 CDRs, 37B9 CDRs, 37C8 CDRs, 37G8 CDRs, 38A4 CDRs, 38C8 CDRs, 38D2 CDRs, 38E3 CDRs and 38G6 CDRs.

The cDNA and amino acid sequences for the full length light and heavy chains of antibody 31A5 is also provided. The cDNA sequence encoding the full length light chain of antibody 31A5, including the constant region, is set forth in SEQ ID NO: 11. The amino acid sequence of the full length light chain of antibody 31A5, including the constant region, is set forth in SEQ ID NO: 12 (of which residues 1-20 correspond to the signal peptide and the remainder is the mature polypeptide) The cDNA sequence encoding the full length heavy chain of antibody 31A5, including the constant region, is set forth in SEQ ID NO: 13. The amino acid sequence of the full length heavy chain of antibody 31A5, including the constant region, is set forth in SEQ ID NO: 14 (of which residues 1-17 correspond to the signal peptide and the remainder is the mature polypeptide).

In another embodiment, the antibody comprises the heavy chain variable region of any of antibodies 34G3, 37A2, 37B9, 37C8, 37G8, 38A4, 38C8, 38D2, 38E3 and 38G6 and optionally comprises a constant region selected from the group consisting of a human IgG1 heavy chain constant region (SEQ ID NOs: 120-121) and a human IgG2 heavy chain constant region (SEQ ID NOs: 122-123). In another exemplary embodiment, the antibody comprises the light chain variable region of any of antibodies 37B9, 37C8, 37G8, 38A4, 38C8, 38D2 and 38E3 and optionally comprises a human kappa light chain constant region (SEQ ID NOs: 124-125). In another exemplary embodiment, the antibody comprises the light chain variable region of any of antibodies 37A2 and 38G6 and optionally comprises a constant region selected from the group consisting of a human lambda light chain constant region type C1 (SEQ ID NOs: 126-127), a human lambda light chain constant region type C2 (SEQ ID NOs: 128-129), a human lambda light chain constant region type C3 (SEQ ID NOs: 130-131), a human lambda light chain constant region type C6 (SEQ ID NOs: 132-133) and a human lambda light chain constant region type C7 (SEQ ID NO: 134-135).

The term "monoclonal antibody" as used herein refers to an antibody, as that term is defined herein, obtained from a population of substantially homogeneous antibodies, i.e., the individual antibodies comprising the population are identical except for possible naturally occurring mutations or alternative post-translational modifications that may be present in minor amounts, whether produced from hybridomas or recombinant DNA techniques. Nonlimiting examples of monoclonal antibodies include mouse, rabbit, rat, chicken, chimeric, humanized, or human antibodies, fully assembled antibodies, multispecific antibodies (including bispecific antibodies), antibody fragments that can bind an antigen (including, Fab', F'(ab)$_2$, Fv, single chain antibodies, diabodies), maxibodies, nanobodies, and recombinant peptides comprising the foregoing as long as they exhibit the desired biological activity, or variants or derivatives thereof. Humanizing or modifying antibody sequence to be more human-like is described in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun 28:489 498 (1991); Padlan, Molec. Immunol. 31(3):169 217 (1994); and Kettleborough, C. A. et al., Protein Eng. 4(7):773 83 (1991); Co, M. S., et al. (1994), J. Immunol. 152, 2968-2976); Studnicka et al. Protein Engineering 7: 805-814 (1994); each of which is incorporated herein by reference in its entirety. One method for isolating human monoclonal antibodies is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. Another method for isolating human monoclonal antibodies uses transgenic animals that have no endogenous immunoglobulin production and are engineered to contain human immunoglobulin loci. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); WO 91/10741, WO 96/34096, WO 98/24893, or U.S. patent application publication nos. 20030194404, 20030031667 or 20020199213; each incorporated herein by reference in its entirety.

An "isolated" antibody refers to an antibody, as that term is defined herein, that has been identified and separated from a component of its natural environment. Contaminant components of its natural environment are materials that would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody, and most preferably more than 99% by weight, (2) to a degree sufficient to obtain at least 15 residues of N-terminal or internal amino acid sequence, or (3) to homogeneity by SDS-PAGE under reducing or nonreducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" ("V") region of about 100 to 110 or more amino acids primarily responsible for antigen recognition. The carboxy-terminal portion of each chain defines a constant region and the constant regions of the heavy chains are primarily responsible for effector function Immunoglobulins can be assigned to different classes depending on the amino acid sequence of the constant domain of their heavy chains. Heavy chains are classified as mu ($\mu$), delta ($\delta$), gamma ($\gamma$), alpha ($\alpha$), and epsilon ($\epsilon$), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activity. Human light chains are classified as kappa ($\kappa$) and lambda ($\lambda$) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

Allotypes are variations in antibody sequence, often in the constant region, that can be immunogenic and are encoded by specific alleles in humans. Allotypes have been identified for five of the human IGHC genes, the IGHG1, IGHG2, IGHG3, IGHA2 and IGHE genes, and are designated as G1m, G2m, G3m, A2m, and Em allotypes, respectively. At least 18 Gm allotypes are known: nG1m(1), nG1m(2), G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5). There are two A2m allotypes A2m(1) and A2m(2).

For a detailed description of the structure and generation of antibodies, see Roth, D. B., and Craig, N. L., Cell, 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "hypervariable" region refers to amino acid residues from a complementarity determining region or CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, $5^{th}$ Ed. Public Health Service, National Institutes of Health, Bethesda, Md. (1991)). Even a single CDR may recognize and bind antigen, although with a lower affinity than the entire antigen-binding site containing all of the CDRs.

An alternative definition of residues from a hypervariable "loop" is described by Chothia et al., J. Mol. Biol, 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or FR residues are those variable region residues other than the hypervariable region residues.

"Antibody fragments" comprise a portion of an intact immunoglobulin, preferably an antigen-binding or variable region of the intact antibody, and include multispecific (bispecific, trispecific, etc.) antibodies formed from antibody fragments. Fragments of immunoglobulins may be produced by recombinant DNA techniques or by enzymatic or chemical cleavage of intact antibodies.

Nonlimiting examples of antibody fragments include Fab, Fab', F(ab')$_2$, Fv (variable region), domain antibodies (dAb, containing a VH domain) (Ward et al., Nature 341:544-546, 1989), complementarity determining region (CDR) fragments, single-chain antibodies (scFv, containing VH and VL domains on a single polypeptide chain) (Bird et al., Science 242:423-426, 1988, and Huston et al., Proc. Natl. Acad. Sci. USA 85:5879-5883, 1988, optionally including a polypeptide linker; and optionally multispecific, Gruber et al., J. Immunol. 152: 5368 (1994)), single chain antibody fragments, diabodies (VH and VL domains on a single polypeptide chain that pair with complementary VL and VH domains of another chain) (EP 404,097; WO 93/11161; and Hollinger et al., Proc. Natl. Acad. Sci. USA, 90:6444-6448 (1993)), triabodies, tetrabodies, minibodies (scFv fused to CH3 via a peptide linker (hingeless) or via an IgG hinge) (Olafsen, et al., Protein Eng Des Sel. 2004 April; 17(4):315-23), linear antibodies (tandem Fd segments (VH-CH1-VH-CH1) (Zapata et al., Protein Eng., 8(10):1057-1062 (1995)); chelating recombinant antibodies (crAb, which can bind to two adjacent epitopes on the sane antigen) (Neri et al., J Mol Biol. 246:367-73, 1995), bibodies (bispecific Fab-scFv) or tribodies (trispecific Fab-(scFv)(2)) (Schoonjans et al., J Immunol. 165:7050-57, 2000; Willems et al., J Chromatogr B Analyt Technol Biomed Life Sci. 786:161-76, 2003), intrabodies (Biocca, et al., EMBO J. 9:101-108, 1990; Colby et al., Proc Natl Acad Sci USA. 101:17616-21, 2004) which may also comprise cell signal sequences which retain or direct the antibody intracellularly (Mhashilkar et al, EMBO J 14:1542-51, 1995; Wheeler et al., FASEB J. 17:1733-5, 2003), transbodies (cell-permeable antibodies containing a protein transduction domain (PTD) fused to scFv (Heng et al., Med Hypotheses. 64:1105-8, 2005), nanobodies (approximately 15 kDa variable domain of the heavy chain) (Cortez-Retamozo et al., Cancer Research 64:2853-57, 2004), small modular immunopharmaceuticals (SMIPs) (WO 03/041600, U.S. Patent publication 20030133939 and US Patent Publication 20030118592), an antigen-binding-domain immunoglobulin fusion protein, a camelized antibody (in which VH recombines with a constant region that contains hinge, CH1, CH2 and CH3 domains) (Desmyter et al., J. Biol. Chem. 276:26285-90, 2001; Ewert et al., Biochemistry 41:3628-36, 2002; U.S. Patent Publication Nos. 20050136049 and 20050037421), a VHH containing antibody, heavy chain antibodies (HCAbs, homodimers of two heavy chains having the structure H2L2), or variants or derivatives thereof, and polypeptides that contain at least a portion of an immunoglobulin that is sufficient to confer specific antigen binding to the polypeptide, such as a CDR sequence, as long as the antibody retains the desired biological activity.

The term "variant," when used in connection with antibodies, refers to a polypeptide sequence of an antibody that contains at least one amino acid substitution, deletion, or insertion in the variable region or the portion equivalent to the variable region, provided that the variant retains the desired binding affinity or biological activity. In addition, the antibodies as described herein may have amino acid modifications in the constant region to modify effector function of the antibody, including half-life or clearance, ADCC and/or CDC activity. Such modifications can enhance pharmacokinetics or enhance the effectiveness of the antibody in treating cancer, for example. See Shields et al., J. Biol. Chem., 276(9):6591-6604 (2001), incorporated by reference herein in its entirety. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

The term "modification" when used in connection with antibodies or polypeptides described herein, includes but is not limited to, one or more amino acid change (including substitutions, insertions or deletions); chemical modifications that do not interfere with ferroportin-binding activity; covalent modification by conjugation to therapeutic or diagnostic agents; labeling (e.g., with radionuclides or various enzymes); covalent polymer attachment such as pegylation (derivatization with polyethylene glycol) and insertion or substitution by chemical synthesis of non-natural amino acids. In some embodiments, modified polypeptides (including antibodies) of the invention will retain the binding properties of unmodified molecules of the invention.

The term "derivative" when used in connection with antibodies or polypeptides of the invention refers to antibodies or polypeptides that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. In some embodiments, derivatives of the invention will retain the binding properties of underivatized molecules of the invention.

Methods for making bispecific or other multispecific antibodies are known in the art and include chemical cross-linking, use of leucine zippers (Kostelny et al., J. Immunol. 148:1547-1553, 1992); diabody technology (Hollinger et al., Proc. Natl. Acad. Sci. USA 90:6444-48, 1993); scFv dimers (Gruber et al., J. Immunol. 152: 5368, 1994), linear antibodies (Zapata et al., Protein Eng. 8:1057-62, 1995); and chelating recombinant antibodies (Neri et al., J Mol Biol. 246:367-73, 1995).

Thus, a variety of compositions comprising one, two, and/or three CDRs of a heavy chain variable region or a light chain variable region of an antibody may be generated by techniques known in the art.

A. Recombinant Production of Antibodies

Isolated nucleic acids encoding monoclonal antibodies described herein are also provided, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

Relevant amino acid sequence from an immunoglobulin of interest may be determined by direct protein sequencing, and suitable encoding nucleotide sequences can be designed according to a universal codon table. Alternatively, genomic or cDNA encoding the monoclonal antibodies may be isolated and sequenced from cells producing such antibodies using conventional procedures (e.g., by using oligonucleotide probes that are capable of binding specifically to genes encoding the heavy and light chains of the monoclonal antibodies).

Cloning is carried out using standard techniques (see, e.g., Sambrook et al. (2001) Molecular Cloning: A Laboratory Guide, 3$^{rd}$ Ed., Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

The sequence encoding an entire variable region of the immunoglobulin polypeptide may be determined; however, it will sometimes be adequate to sequence only a portion of a variable region, for example, the CDR-encoding portion. Sequencing is carried out using standard techniques (see, e.g., Sambrook et al. (2001) Molecular Cloning: A Laboratory Guide, 3$^{rd}$ Ed., Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the antibody where, for example, the nucleic acid molecule is in a chromosomal location different from that of natural cells.

Once isolated, the DNA may be operably linked to expression control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

Expression control sequences refer to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the antibody), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Exemplary host cells include prokaryote, yeast, or higher eukaryote cells (i.e., a multicellular organism). Prokaryotic host cells include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas*, and *Streptomyces*. Eukaryotic microbes such as filamentous fungi or yeast are suitable cloning or expression hosts for recombinant polypeptides or antibodies. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris*, *Schizosaccharomyces pombe*; *Kluyveromyces*, *Yarrowia*; *Candida*; *Trichoderma reesia*; *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Host cells for the expression of glycosylated polypeptide or antibody can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

Vertebrate host cells are also suitable hosts, and recombinant production of polypeptide or antibody from such cells has become routine procedure. Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., J. Gen Virol. 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68 (1982)); MRC 5 cells or FS4 cells; or mammalian myeloma cells.

Host cells are transformed or transfected with the above-described nucleic acids or vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of antibodies.

The host cells used to produce an antibody described herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration.

The antibody can be purified using, for example, hydroxylapatite chromatography, cation or anion exchange chromatography, or preferably affinity chromatography, using the antigen of interest or protein A or protein G as an affinity ligand. Protein A can be used to purify antibodies that are based on human $\gamma 1$, $\gamma 2$, or $\gamma 4$ heavy chains (Lindmark et al., J. Immunol. Meth. 62: 1-13 (1983)). Protein G is recommended for all mouse isotypes and for human $\gamma 3$ (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered.

B. Chimeric and Humanized Antibodies

Because chimeric or humanized antibodies are less immunogenic in humans than the parental rodent monoclonal antibodies, they can be used for the treatment of humans with far less risk of anaphylaxis. Thus, these antibodies are contemplated in therapeutic applications that involve in vivo administration to a human.

For example, a mouse antibody on repeated in vivo administration in a human either alone or as a conjugate will bring about an immune response in the recipient, sometimes called a HAMA response (Human Anti-Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using the methods of genetic engineering to make the antibody binding structure more human like.

The phrase "chimeric antibody," as used herein, refers to an antibody containing sequence derived from two different antibodies which typically originate from different species. Most typically, chimeric antibodies comprise variable Ig domains of a rodent monoclonal antibody fused to human constant Ig domains. Such antibodies can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). Although some chimeric monoclonal antibodies have proved less immunogenic in humans, the rodent variable Ig domains can still lead to a significant human anti-rodent response.

The phrase "humanized antibody" refers to an antibody derived from a non-human antibody, typically a rodent monoclonal antibody. Alternatively, a humanized antibody may be derived from a chimeric antibody.

Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering"). These methods are disclosed in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65-92 (1988); Verhoeyer et al., Science 239:1534-1536 (1988); Padlan, Molec. Immun 28:489-498 (1991); Padlan, Molec. Immunol. 31(3):169 217 (1994); and Kettleborough, C. A. et al., Protein Eng. 4(7): 773-83 (1991) each of which is incorporated herein by reference in its entirety.

CDR grafting involves introducing one or more of the six CDRs from the mouse heavy and light chain variable Ig domains into the appropriate framework regions of a human variable Ig domain. This technique (Riechmann, L., et al., Nature 332, 323 (1988)), utilizes the conserved framework regions (FR1-FR4) as a scaffold to support the CDR loops which are the primary contacts with antigen. A significant disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen-binding site (e.g., Co, M. S., et al. (1994), J. Immunol. 152, 2968-2976).

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors (See, e.g., U.S. Pat. Nos. 5,530,101 and 5,585,089).

A number of humanizations of mouse monoclonal antibodies by rational design have been reported (See, for example, 20020091240 published Jul. 11, 2002, WO 92/11018 and U.S. Pat. No. 5,693,762, U.S. Pat. No. 5,766,866.

C. Human Engineered™ Antibodies

The phrase "Human Engineered™ antibody" refers to an antibody derived from a non-human antibody, typically a rodent monoclonal antibody or possibly a chimeric antibody. Human Engineering™ of antibody variable domains has been described by Studnicka (See, for example, Studnicka et al. U.S. Pat. No. 5,766,886; Studnicka et al. Protein Engineering 7: 805-814, 1994) as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position.

Variable regions of the light and heavy chains of a rodent antibody can be Human Engineered™ by substituting human amino acids at positions determined to be unlikely to adversely effect either antigen binding or protein folding, but likely to reduce immunogenicity in a human environment. Although any human variable region can be used, including an individual VH or VL sequence or a human consensus VH or VL sequence or an individual or consensus human germline sequence, generally a human sequence with highest identity or homology to the rodent sequence is used to minimize the number of substitutions. The amino acid residues at any number of the low risk positions, or at all of the low risk positions, can be changed. For example, at each low risk position where the aligned murine and human amino acid residues differ, an amino acid modification is introduced that replaces the rodent residue with the human residue. In addition, the amino acid residues at any number or all of the moderate risk positions can be changed. In exemplary embodiments, all of the low and moderate risk positions are changed from rodent to human sequence.

Synthetic genes containing modified heavy and/or light chain variable regions are constructed and linked to human γ heavy chain and/or kappa light chain constant regions. Any human heavy chain and light chain constant regions of any class or subclass may be used in combination with the Human Engineered™ antibody variable regions.

D. Antibodies from Transgenic Animals Engineered to Contain Human Immunoglobulin Loci Antibodies to ferroportin can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein.

See also Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. No. 5,591,669, U.S. Pat. No. 5,589,369, U.S. Pat. No. 5,545,807; and U.S Patent Application No. 20020199213. U.S. Patent Application No. 20030092125 describes methods for biasing the immune response of an animal to the desired epitope. Human antibodies may also be generated by in vitro activated B cells (see U.S. Pat. Nos. 5,567,610 and 5,229,275).

E. Antibody Production by Phage Display Techniques

The development of technologies for making repertoires of recombinant human antibody genes, and the display of the encoded antibody fragments on the surface of filamentous bacteriophage, has provided another means for generating human-derived antibodies. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. The antibodies produced by phage technology are usually produced as antigen-binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated.

Phage display techniques can also be used in an approach for the humanization of rodent monoclonal antibodies, called "guided selection" (see Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); and, Winter, G., et al., Annu. Rev. Immunol. 12, 433-455 (1994); U.S. patent application no. 20020004215 and WO92/01047; U.S. patent application no. 20030190317 published Oct. 9, 2003 and U.S. Pat. No. 6,054,287; U.S. Pat. No. 5,877,293.

Watkins, "Screening of Phage-Expressed Antibody Libraries by Capture Lift," Methods in Molecular Biology, Antibody Phage Display: Methods and Protocols 178: 187-193, and U.S. Patent Application Publication No. 20030044772 published Mar. 6, 2003 describes methods for screening phage-expressed antibody libraries or other binding molecules by capture lift, a method involving immobilization of the candidate binding molecules on a solid support.

F. Antibody Fragments

As noted above, antibody fragments comprise a portion of an intact full length antibody, preferably an antigen-binding or variable region of the intact antibody, and include linear antibodies and multispecific antibodies formed from antibody fragments. Nonlimiting examples of antibody fragments include Fab, Fab', F(ab')2, Fv, Fd, domain antibody (dAb), complementarity determining region (CDR) fragments, single-chain antibodies (scFv), single chain antibody fragments, diabodies, triabodies, tetrabodies, minibodies, linear antibodies, chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen-binding to the polypeptide, such as a CDR sequence, as long as the antibody retains the desired biological activity. Such antigen fragments may be produced by the modification of whole antibodies or synthesized de novo using recombinant DNA technologies or peptide synthesis.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., Science, 242:423-426, 1988, and Huston et al., Proc. Natl. Acad. Sci. USA, 85:5879-5883, 1988). An Fd fragment consists of the $V_H$ and $C_H1$ domains.

Additional antibody fragments include a domain antibody (dAb) fragment (Ward et al., Nature, 341:544-546, 1989) which consists of a $V_H$ domain.

"Linear antibodies" comprise a pair of tandem Fd segments ($V_H$-$C_H1$-$V_H$-$C_H1$) which form a pair of antigen-binding regions. Linear antibodies can be bispecific or monospecific (Zapata et al. Protein Eng. 8:1057-62 (1995)).

A "minibody" consisting of scFv fused to CH3 via a peptide linker (hingeless) or via an IgG hinge has been described in Olafsen, et al., Protein Eng Des Sel. 2004 April; 17(4):315-23.

The term "maxibody" refers to bivalent scFvs covalently attached to the Fc region of an immunoglobulin, see, for example, Fredericks et al, Protein Engineering, Design & Selection, 17:95-106 (2004) and Powers et al., Journal of Immunological Methods, 251:123-135 (2001).

Functional heavy-chain antibodies devoid of light chains are naturally occurring in certain species of animals, such as nurse sharks, wobbegong sharks and Camelidae, such as camels, dromedaries, alpacas and llamas. The antigen-binding site is reduced to a single domain, the $VH_H$ domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelized $V_{HH}$ reportedly recombines with IgG2 and IgG3 constant regions that contain hinge, CH2, and CH3 domains and lack a CH1 domain. Classical $V_H$-only fragments are difficult to produce in soluble form, but improvements in solubility and specific binding can be obtained when framework residues are altered to be more $VH_H$-like. (See, e.g., Reichman, et al., J. Immunol. Methods, 1999, 231:25-38.) Camelized $V_{HH}$ domains have been found to bind to antigen with high affinity (Desmyter et al., J. Biol. Chem., 276:26285-90, 2001) and possess high stability in solution (Ewert et al., Biochemistry, 41:3628-36, 2002). Methods for generating antibodies having camelized heavy chains are described in, for example, in U.S. Patent Publication Nos. 20050136049 and 20050037421. Alternative scaffolds can be made from human variable-like domains that more closely match the shark V-NAR scaffold and may provide a framework for a long penetrating loop structure.

Because the variable domain of the heavy-chain antibodies is the smallest fully functional antigen-binding fragment with a molecular mass of only 15 kDa, this entity is referred to as a nanobody (Cortez-Retamozo et al., Cancer Research, 64:2853-57, 2004). A nanobody library may be generated from an immunized dromedary as described in Conrath et al., (Antimicrob Agents Chemother, 45: 2807-12, 2001).

Intrabodies are single chain antibodies which demonstrate intracellular expression and can manipulate intracellular protein function (Biocca, et al., EMBO J., 9:101-108, 1990; Colby et al., Proc Natl Acad Sci USA., 101:17616-21, 2004). Intrabodies, which comprise cell signal sequences which retain the antibody contruct in intracellular regions, may be produced as described in Mhashilkar et al (EMBO J, 14:1542-51, 1995) and Wheeler et al. (FASEB J., 17:1733-5. 2003). Transbodies are cell-permeable antibodies in which a protein transduction domains (PTD) is fused with single chain variable fragment (scFv) antibodies Heng et al., (Med Hypotheses., 64:1105-8, 2005).

Further contemplated are antibodies that are SMIPs or binding domain immunoglobulin fusion proteins specific for target protein. These constructs are single-chain polypeptides comprising antigen-binding domains fused to immunoglobulin domains necessary to carry out antibody effector functions. See e.g., WO03/041600, U.S. Patent publication 20030133939 and US Patent Publication 20030118592.

G. Multivalent Antibodies

In some embodiments, it may be desirable to generate multivalent or even a multispecific (e.g., bispecific, trispecific, etc.) monoclonal antibody. Such antibody may have binding specificities for at least two different epitopes of the target antigen, or alternatively it may bind to two different molecules, e.g. to the target antigen and to a cell surface protein or receptor. For example, a bispecific antibody may include an arm that binds to the target and another arm that binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the target-expressing cell. As another example, bispecific antibodies may be used to localize cytotoxic agents to cells which express target antigen. These antibodies possess a target-binding arm and an arm which binds the cytotoxic agent (e.g., saporin, anti-interferon-60, vinca alkaloid, ricin A chain, methotrexate or radioactive isotope hapten). Multispecific antibodies can be prepared as full length antibodies or antibody fragments.

Additionally, the anti-ferroportin antibodies disclosed herein can also be constructed to fold into multivalent forms, which may improve binding affinity, specificity and/or increased half-life in blood. Multivalent forms of anti-ferroportin antibodies can be prepared by techniques known in the art.

Bispecific or multispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques. Another method is designed to make tetramers by adding a streptavidin-coding sequence at the C-terminus of the scFv. Streptavidin is composed of four subunits, so when the scFv-streptavidin is folded, four subunits associate to form a tetramer (Kipriyanov et al., Hum Antibodies Hybridomas 6(3): 93-101 (1995), the disclosure of which is incorporated herein by reference in its entirety).

According to another approach for making bispecific antibodies, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO 96/27011 published Sep. 6, 1996.

Techniques for generating bispecific or multispecific antibodies from antibody fragments have also been described in the literature. For example, bispecific or trispecific antibodies can be prepared using chemical linkage. Brennan et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. Better et al., Science 240: 1041-1043 (1988) disclose secretion of functional antibody fragments from bacteria (see, e.g., Better et al., Skerra et al. Science 240: 1038-1041 (1988)). For example, Fab'-SH fragments can be directly recovered from *E. coli* and chemically coupled to form bispecific antibodies (Carter et al., Bio/Technology 10:163-167 (1992); Shalaby et al., J. Exp. Med. 175:217-225 (1992)).

Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecfic antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific or multispecific antibody fragments directly from recombinant cell culture have also been described. For example, bispecific antibodies have been produced using leucine zippers, e.g., GCN4. (See generally Kostelny et al., J. Immunol. 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

Diabodies, described above, are one example of a bispecific antibody. See, for example, Hollinger et al., Proc. Natl. Acad. Sci. USA, 90:6444-6448 (1993). Bivalent diabodies can be stabilized by disulfide linkage.

Stable monospecific or bispecific Fv tetramers can also be generated by noncovalent association in (scFv$_2$)$_2$ configuration or as bis-tetrabodies. Alternatively, two different scFvs can be joined in tandem to form a bis-scFv.

Another strategy for making bispecific antibody fragments by the use of single-chain Fv (sFv) dimers has also been reported. See Gruber et al., J. Immunol. 152: 5368 (1994). One approach has been to link two scFv antibodies with linkers or disulfide bonds (Mallender and Voss, J. Biol. Chem. 269:199-2061994, WO 94/13806, and U.S. Pat. No. 5,989,830, the disclosures of which are incorporated herein by reference in their entireties).

Alternatively, the bispecific antibody may be a "linear antibody" produced as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen-binding regions. Linear antibodies can be bispecific or monospecific.

Antibodies with more than two valencies are also contemplated. For example, trispecific antibodies can be prepared. (Tutt et al., J. Immunol. 147:60 (1991)).

A "chelating recombinant antibody" is a bispecific antibody that recognizes adjacent and non-overlapping epitopes of the target antigen, and is flexible enough to bind to both epitopes simultaneously (Neri et al., *J Mol Biol.* 246:367-73, 1995).

Production of bispecific Fab-scFv ("bibody") and trispecific Fab-(scFv)(2) ("tribody") are described in Schoonjans et al. (J Immunol., 165:7050-57, 2000) and Willems et al. (J. Chromatogr. B. Analyt. Technol. Biomed. Life Sci., 786: 161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab.

In yet another method, dimers, trimers, and tetramers are produced after a free cysteine is introduced in the parental protein. A peptide-based cross linker with variable numbers (two to four) of maleimide groups was used to cross link the protein of interest to the free cysteines (Cochran et al., Immunity 12(3): 241-50 (2000), the disclosure of which is incorporated herein in its entirety).

II. Specific Binding Agents

Other ferroportin-specific binding agents can be prepared, for example, based on CDRs from an antibody or by screening libraries of diverse peptides or organic chemical compounds for peptides or compounds that exhibit the desired binding properties for human ferroportin. Ferroportin-specific binding agents include peptides containing amino acid sequences that are at least 80%, 81%, 82%, 83%, 84%, 85%, 86%, 87%, 88%, 89%, 90%, 91%, 92%, 93%, 94%, 95%, 96%, 97%, 98%, 99% or more identical to one or more CDRs of human antibody 31A5 (SEQ ID NOs: 5-10), human antibody 37A2 (SEQ ID NOs: 29-34), human antibody 37B9 (SEQ ID NOs: 39-44), human antibody 37C8 (SEQ ID NOs: 49-54) human antibody 37G8 (SEQ ID NOs: 59-64), human antibody 38A4 (SEQ ID NOs: 69-74), human antibody 38C8 (SEQ ID NOs: 79-84), human antibody 38D2 (SEQ ID NOs: 89-94), human antibody 38E3 (SEQ ID NOs: 99-104) or human antibody 38G6 (SEQ ID NOs: 109-114).

Ferroportin-specific binding agents also include peptibodies. The term "peptibody" refers to a molecule comprising an antibody Fc domain attached to at least one peptide. The production of peptibodies is generally described in PCT publication WO 00/24782, published May 4, 2000. Any of these peptides may be linked in tandem (i.e., sequentially), with or without linkers. Peptides containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized, for example, the carboxyl terminus may be capped with an amino group, cysteines may be capped, or amino acid residues may substituted by moieties other than amino acid residues (see, e.g., Bhatnagar et al., J. Med. Chem. 39: 3814-9 (1996), and Cuthbertson et al., J. Med. Chem. 40: 2876-82 (1997), which are incorporated by reference herein in their entirety). The peptide sequences may be optimized, analogous to affinity maturation for antibodies, or otherwise altered by alanine scanning or random or directed mutagenesis followed by screening to identify the best binders. (Lowman, Ann. Rev. Biophys. Biomol. Struct., 26: 401-24, 1997). Various molecules can be inserted into the specific binding agent structure, e.g., within the peptide portion itself or between the peptide and vehicle portions of the specific binding agents, while retaining the desired activity of specific binding agent. One can readily insert, for example, molecules such as an Fc domain or fragment thereof, polyethylene glycol or other related molecules such as dextran, a fatty acid, a lipid, a cholesterol group, a small carbohydrate, a peptide, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of, for example, a desired molecule in between two consecutive amino acids, optionally joined by a suitable linker.

The development of ferroportin peptibodies is also contemplated. The interaction of a protein ligand with its receptor often takes place at a relatively large interface.

However, as demonstrated for human growth hormone and its receptor, only a few key residues at the interface contribute to most of the binding energy. (Clackson et al., Science, 267: 383-6, 1995). The bulk of the protein ligand merely displays the binding epitopes in the right topology or serves functions unrelated to binding. Thus, molecules of only "peptide" length (generally 2 to 40 amino acids) can bind to the receptor protein of a given large protein ligand. Such peptides may mimic the bioactivity of the large protein ligand ("peptide agonists") or, through competitive binding, inhibit the bioactivity of the large protein ligand ("peptide antagonists").

Phage display technology has emerged as a powerful method in identifying such peptide agonists and antagonists. See, for example, Scott et al. Science 249: 386 (1990); Devlin et al., Science 249: 404 (1990); U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference in its entirety). In peptide phage display libraries, random peptide sequences can be displayed by fusion with coat proteins of filamentous phage. The displayed peptides can be affinity-eluted against an antibody-immobilized extracellular domain of a receptor, if desired. The retained phage may be enriched by successive rounds of affinity purification and repropagation. The best binding peptides may be sequenced to identify key residues within one or more structurally related families of peptides. See, e.g., Cwirla et al., Science 276: 1696-9 (1997), in which two distinct families were identified. The peptide sequences may also suggest which residues may be safely replaced by alanine scanning or by mutagenesis at the DNA level. Mutagenesis libraries may be created and screened to further optimize the sequence of the best binders. (Lowman, Ann. Rev. Biophys. Biomol. Struct., 26: 401-24, 1997).

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed. See, e.g., Takasaki et al., Nature Biotech 15: 1266-70 (1997). These analytical methods may also be used to investigate the interaction between a receptor protein and peptides selected by phage display, which may suggest further modification of the peptides to increase binding affinity.

Other methods compete with phage display in peptide research. A peptide library can be fused to the carboxyl terminus of the lac repressor and expressed in *E. coli*. Another *E. coli*-based method allows display on the cell's outer membrane by fusion with a peptidoglycan-associated lipoprotein (PAL). Hereinafter, these and related methods are collectively referred to as "*E. coli* display." In another method, translation of random RNA is halted prior to ribosome release, resulting in a library of polypeptides with their associated RNA still attached. Hereinafter, this and related methods are collectively referred to as "ribosome display." Other methods employ chemical linkage of peptides to RNA. See, e.g., Roberts and Szostak, Proc Natl Acad Sci USA, 94: 12297-303 (1997). Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells and Lowman, Curr. Opin. Biotechnol., 3: 355-62 (1992).

Other cell display techniques for peptide libraries include surface display on a yeast, such as *Saccharomyces cerevisiae* (Boder and Wittrup, Nat. Biotechnol. 15:553-557, 1997). Thus, for example, antibodies can be displayed on the surface of *S. cerevisiae* via fusion to the α-agglutinin yeast adhesion receptor, which is located on the yeast cell wall. This method provides the possibility of selecting repertoires by flow cytometry. By staining the cells by fluorescently labeled antigen and an anti-epitope tag reagent, the yeast cells can be sorted according to the level of antigen-binding on the cell surface. Yeast display platforms can also be combined with phage (see, e.g., Van den Beucken et al., FEBS Lett. 546:288-294, 2003).

Conceptually, one may discover peptide mimetics of any protein using phage display and the other methods mentioned above. These methods have been used for epitope mapping, for identification of critical amino acids in protein-protein interactions, and as leads for the discovery of new therapeutic agents. See, e.g., Cortese et al., Curr. Opin. Biotech. 7: 616-21 (1996). Peptide libraries are now being used most often in immunological studies, such as epitope mapping. See Kreeger, The Scientist 10(13):19-20(1996).

Sources for compounds that may be screened for ability to bind to or modulate (i.e., increase or decrease) the activity of ferroportin include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are microorganisms (including bacteria and fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and (non-naturally occurring) variants thereof. For a review, see Science, 282:63-68 (1998).

Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol., 8:701-707 (1997). For reviews and examples of peptidomimetic libraries, see Al-Obeidi et al., Mol. Biotechnol., 9(3):205-23 (1998); Hruby et al., Curr Opin Chem Biol., 1(1):114-19 (1997); Dorner et al., Bioorg Med Chem., 4(5):709-15 (1996) (alkylated dipeptides).

Ferroportin-specific binding agents also include scaffolding proteins, as described by Hays et al., Trends In Biotechnology, 23(10):514-522 (2005), herein incorporated by reference in its entirety, and Avimer protein technology, as described in US Publication Nos. 2006-0286603 and 2006-0223114, both herein incorporated by reference in their entireties.

III. Production of Antibody Variants and Derivatives

The anti-ferroportin antibodies of the invention can readily be modified by techniques well-known to one of ordinary skill in the art. Potential mutations include insertion, deletion or substitution of one or more residues. Insertions or deletions are preferably in the range of about 1 to 5 amino acids, more preferably 1 to 3, and most preferably 1 or 2 amino acids.

Deletion variants are polypeptides wherein at least one amino acid residue of any amino acid sequence is removed. Deletions can be effected at one or both termini of the protein, or with removal of one or more residues within (i.e., internal to) the polypeptide. Methods for preparation of deletion variants are routine in the art. See, e.g., Sambrook et al. (2001) Molecular Cloning: A Laboratory Guide, $3^{rd}$ ed., Cold Spring Harbor Press, the disclosure of which is incorporated herein by reference in its entirety.

Amino acid sequence insertions include amino- and/or carboxyl-terminal fusions ranging in length from one residue to polypeptides containing hundreds or more residues, as well as internal sequence insertions of one or more amino acids. As with any of the different variant types described herein, insertional variants can be designed such that the resulting polypeptide retains the same biological properties or exhibits a new physical, chemical and/or biological property not associated with the parental polypeptide from which it was derived. Methods for preparation of insertion variants are also routine and well known in the art (Sambrook et al., supra).

Fusion proteins comprising an antibody disclosed herein (or one, two, three, four, five, or all of the CDRs of the antibody disclosed herein) and a heterologous polypeptide, are a specific type of insertion variant contemplated by the invention. Non-limiting examples of heterologous polypeptides which can be fused to polypeptides of interest include proteins with long circulating half-life, such as, but not limited to, immunoglobulin constant regions (e.g., Fc region); marker sequences that permit identification of the polypeptide of interest; sequences that facilitate purification of the polypeptide of interest; and sequences that promote formation of multimeric proteins.

Methods of making antibody fusion proteins are well known in the art. See, e.g., U.S. Pat. No. 6,306,393, the disclosure of which is incorporated herein by reference in its entirety. In certain embodiments of the invention, fusion proteins are produced which may include a flexible linker, which connects the chimeric scFv antibody to the heterologous protein moiety. Appropriate linker sequences are those that do not affect the ability of the resulting fusion protein to be recognized and bind the epitope specifically bound by the V domain of the protein (see, e.g., WO 98/25965, the disclosure of which is incorporated herein by reference in its entirety).

Substitution variants are those in which at least one residue in the polypeptide amino acid sequence is removed and a different residue is inserted in its place. Modifications in the biological properties of the polypeptide or antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. In certain embodiments of the invention, substitution variants are designed, i.e., one or more specific (as opposed to random) amino acid residues are substituted with a specific amino acid residue. Typical changes of these types include conservative substitutions and/or substitution of one residue for another based on similar properties of the native and substituting residues.

Conservative substitutions are shown in Table 1. The most conservative substitution is found under the heading of "preferred substitutions." If such substitutions result in no change in biological activity, then more substantial changes may be introduced and the products screened.

TABLE 1

| Original | Exemplary | Preferred Residue Substitutions |
|---|---|---|
| Ala (A) | val; leu; ile | val |
| Arg (R) | lys; gln; asn | lys |
| Asn (N) | gln; his; asp, lys; gln | gln |
| Asp (D) | glu; asn | glu |
| Cys (C) | ser; ala | ser |
| Gln (Q) | asn; glu | asn |
| Glu (E) | asp; gln | asp |
| Gly (G) | ala | |
| His (H) | asn; gln; lys; arg | |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Amino acid residues which share common side-chain properties are often grouped as follows.
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

A. Antibody Variants

In certain instances, antibody variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated.

In order to determine which antibody amino acid residues are important for epitope recognition and binding, alanine scanning mutagenesis can be performed to produce substitution variants. See, e.g., Cunningham et al., Science, 244: 1081-1085 (1989), the disclosure of which is incorporated herein by reference in its entirety. In this method, individual amino acid residues are replaced one-at-a-time with an alanine residue and the resulting anti-ferroportin antibody is screened for its ability to bind its specific epitope relative to the unmodified antibody. Modified antibodies with reduced binding capacity are sequenced to determine which residue was changed, indicating its significance in binding or biological properties.

Substitution variants of antibodies can be prepared by affinity maturation wherein random amino acid changes are introduced into the parent antibody sequence. See, for example, Ouwehand et al., Vox Sang 74 (Suppl 2):223-232, 1998; Rader et al., Proc. Natl. Acad. Sci. USA 95:8910-8915, 1998; Dall'Acqua et al., Curr. Opin. Struct. Biol. 8:443-450, 1998, the disclosures of which are incorporated herein by reference in their entireties. Affinity maturation involves preparing and screening the anti-ferroportin antibodies, or variants thereof and selecting from the resulting variants those that have modified biological properties, such as increased binding affinity relative to the parent anti-ferroportin antibody. A convenient way for generating substitutional variants is affinity maturation using phage display. Briefly, several hypervariable region sites are mutated to generate all possible amino substitutions at each site. The variants thus generated are expressed in a monovalent fashion on the surface of filamentous phage particles as fusions to the gene III product of M13 packaged within each particle. The phage-displayed variants are then screened for their biological activity (e.g., binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., J. Mol. Biol., 260, 359-68, 1996), and saturation mutagenesis (Nishimiya et al., J. Biol. Chem., 275:12813-20, 2000; Chowdhury, P. S. Methods Mol. Biol., 178, 269-85, 2002) are typical examples of stochastic mutagenesis methods (Rajpal et al., Proc Natl Acad Sci USA., 102:8466-71, 2005). Nonstochastic techniques often use alanine-scanning or site-directed mutagenesis to generate limited collections of specific muteins. Some methods are described in further detail below.

Affinity Maturation Via Panning Methods—

Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (Cancer Immunol Immunother., 50:163-71, 2001). Methods of affinity maturation using phage display technologies are described elsewhere herein and known in the art (see e.g., Daugherty et al., Proc Natl Acad Sci USA., 97:2029-34, 2000).

Look-Through Mutagenesis—

Look-through mutagenesis (LTM) (Rajpal et al., Proc Natl Acad Sci USA., 102:8466-71, 2005) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all muteins. After positive selection, clones with improved binding are sequenced, and beneficial mutations are mapped.

Error-Prone PCR—

Error-prone PCR involves the randomization of nucleic acids between different selection rounds. The randomization occurs at a low rate by the intrinsic error rate of the polymerase used but can be enhanced by error-prone PCR (Zaccolo et al., J. Mol. Biol. 285:775-783, 1999) using a polymerase having a high intrinsic error rate during transcription (Hawkins et al., J Mol Biol. 226:889-96, 1992). After the mutation cycles, clones with improved affinity for the antigen are selected using routine methods in the art. Techniques utilizing gene shuffling and directed evolution may also be used to prepare and screen anti-ferroportin antibodies, or variants thereof, for desired activity. For example, Jermutus et al., Proc Natl Acad Sci USA., 98(1): 75-80 (2001) showed that tailored in vitro selection strategies based on ribosome display were combined with in vitro diversification by DNA shuffling to evolve either the off-rate or thermodynamic stability of scFvs; Fermer et al., Tumour Biol. 2004 January-April; 25(1-2):7-13 reported that use of phage display in combination with DNA shuffling raised affinity by almost three orders of magnitude. Dougherty et al., Proc Natl Acad Sci USA. 2000 Feb. 29; 97(5):2029-2034 reported that (i) functional clones occur at an unexpectedly high frequency in hypermutated libraries, (ii) gain-of-function mutants are well represented in such libraries, and (iii) the majority of the scFv mutations leading to higher affinity correspond to residues distant from the binding site.

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, they are subjected to screening as described herein and antibodies with superior properties in one or more relevant assays may be selected for further development.

B. Antibody with Modified Carbohydrate

Antibody variants can also be produced that have a modified glycosylation pattern relative to the parent antibody, for example, adding or deleting one or more of the carbohydrate moieties bound to the specific binding agent or antibody, and/or adding or deleting one or more glycosylation sites in the specific binding agent or antibody.

Glycosylation of polypeptides, including antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to a specific binding agent or antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to a specific binding agent or antibody by inserting or substituting one or more serine or threonine residues to the sequence of the original specific binding agent or antibody.

C. Altered Effector Function

Cysteine residue(s) may be removed or introduced in the Fc region of an antibody or Fc-containing polypeptide, thereby eliminating or increasing interchain disulfide bond formation in this region. A homodimeric specific binding agent or antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric specific binding agents or antibodies may also be prepared using heterobifunctional cross-linkers as described in Wolff et al., Cancer Research 53: 2560-2565 (1993). Alternatively, a specific binding agent or antibody can be engineered which has dual Fc regions and may thereby have enhanced complement lysis and ADCC capabilities. See Stevenson et al., Anti-Cancer Drug Design, 3: 219-230 (1989).

It has been shown that sequences within the CDR can cause an antibody to bind to MHC Class II and trigger an unwanted helper T-cell response. A conservative substitution can allow the specific binding agent or antibody to retain binding activity yet reduce its ability to trigger an unwanted T-cell response. It is also contemplated that one or more of the N-terminal 20 amino acids of the heavy or light chain are removed.

In some embodiments, the invention also contemplates production of antibody molecules with altered carbohydrate structure resulting in altered effector activity, including antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., Biotechnol Bioeng. 2004 Sep. 5; 87(5):614-22). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., Mol Immunol. 1989 December; 26(12):1113-23). Some host cell strains, e.g. Lec13 or rat hybridoma YB2/0 cell line naturally produce antibodies with lower fucosylation levels. Shields et al., J Biol Chem. 2002 Jul. 26; 277(30):26733-40; Shinkawa et al., J Biol Chem. 2003 Jan. 31; 278(5):3466-73. An increase in the level of bisected carbohydrate, e.g. through recombinantly producing antibody in cells that overexpress GnTIII enzyme, has also been determined to increase ADCC activity. Umana et al., Nat Biotechnol. 1999 February; 17(2):176-80. It has been predicted that the absence of only one of the two fucose residues may be sufficient to increase ADCC activity. (Ferrara et al., J Biol Chem. 2005 Dec. 5).

D. Other Covalent Modifications

Covalent modifications of an antibody are also included within the scope of this invention. They may be made by chemical synthesis or by enzymatic or chemical cleavage of the polypeptide or antibody, if applicable. Other types of covalent modifications can be introduced by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-13-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R—N.dbd.C.dbd.N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the specific binding agent or antibody. These procedures are advantageous in that they do not require production of the polypeptide or antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the specific binding agent or antibody may be accomplished chemically or enzymatically. Chemical deglycosylation requires exposure of the specific binding agent or antibody to the compound trifluoromethanesulfonic acid, or an equivalent compound. This treatment results in the cleavage of most or all sugars except the linking sugar (N-acetylglucosamine or N-acetylgalactosamine), while leaving the specific binding agent or antibody intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on a specific binding agent or antibody can be achieved by the use of a variety of endo- and exo-glycosidases as described by Thotakura et al. Meth. Enzymol. 138: 350 (1987).

Another type of covalent modification of the antibody or specific binding agent disclosed herein comprises linking the specific binding agent or antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

IV. Screening Methods for Antibodies or Specific Binding Agents

Methods of identifying antibodies which bind ferroportin, which cross-block exemplary antibodies herein, and/or which inhibit ferroportin activity are also provided.

Antibodies may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

To initially screen for antibodies which bind to the desired epitope on the target antigen, a routine cross-blocking assay such as that described in Antibodies, A Laboratory Manual, Cold Spring Harbor Laboratory, Ed Harlow and David Lane (1988) and Harlow, Edward, and David Lane. *Using Antibodies: A Laboratory Manual.* Cold Spring Harbor, N.Y.: Cold Spring Harbor Laboratory Press, 1999, can be performed. Routine competitive binding assays may also be used, in which the unknown antibody is characterized by its ability to inhibit binding of target to a target-specific antibody of the invention. Intact antigen, fragments thereof such as the extracellular domain, or linear epitopes can be used. Epitope mapping is described in Champe et al., J. Biol. Chem. 270: 1388-1394 (1995).

In one variation of an in vitro binding assay, a method is provided comprising (a) contacting an immobilized ferroportin with a candidate antibody and (b) detecting binding of the candidate antibody to the ferroportin. In an alternative embodiment, the candidate antibody is immobilized and binding of ferroportin is detected Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

Antibodies that inhibit or neutralize human ferroportin activity may be identified by contacting ferroportin with an antibody, comparing ferroportin activity in the presence and absence of the test antibody, and determining whether the presence of the antibody decreases activity of the ferroportin. The biological activity of a particular antibody, or combination of antibodies, may be evaluated in vivo using a suitable animal model, including any of those described herein.

In exemplary embodiments, the invention includes high throughput screening (HTS) assays to identify antibodies that interact with or inhibit biological activity (i e, inhibit phosphorylation, dimerization, ligand induced-receptor activation, or intracellular signaling, etc.) of target antigen. HTS assays permit screening of large numbers of compounds in an efficient manner. Cell-based HTS systems are contemplated to investigate the interaction between target antigen and its binding partners. HTS assays are designed to identify "hits" or "lead compounds" having the desired property, from which modifications can be designed to improve the desired property.

In another embodiment of the invention, high throughput screening for antibody fragments or CDRs with 1, 2, 3 or more modifications to amino acids within the CDRs having suitable binding affinity to a target antigen polypeptide is employed.

V. Detection of Ferroportin

Also provided are methods for detecting ferroportin. To determine the presence or absence of ferroportin in a sample, a biological sample from a patient is contacted with one or more of the anti-ferroportin antibodies disclosed herein under conditions and for a time sufficient to allow immunocomplexes to form Immunocomplexes formed between an anti-ferroportin antibody and ferroportin in the biological sample are then detected. The amount of ferroportin in the sample is quantitated by measuring the amount of the immunocomplex formed between the antibody and ferroportin.

Various immunoassays known in the art can be used, including but are not limited to: competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radio-isotope labels, for example), Western analysis, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. Antibodies: A Laboratory Manual (1988) by Harlow & Lane or and Harlow, Edward, and David Lane. *Using Antibodies: A Laboratory Manual*. Cold Spring Harbor, N.Y.: Cold Spring Harbor Laboratory Press, 1999, or more recent editions; Immunoassays: A Practical Approach, Oxford University Press, Gosling, J. P. (ed.) (2001) or more recent editions; and/or Current Protocols in Molecular Biology (Ausubel et al.), which is regularly updated. Examples of such assays usually involve the antibody attached to a surface or matrix, a biological sample expected to contain ferroportin as described above is added and time allowed for a complex to form; suitable washing procedures to remove unbound complex, followed by either the addition of a second antibody to allow detection of the complex (a sandwich ELISA) or a detectable version of ferroportin to detect free ferroportin binding sites on the antibody surface (a competition ELISA).

Within other methods, a biological sample obtained from a patient is tested for the level of ferroportin. The biological sample is incubated with one or more of the anti-ferroportin antibodies disclosed herein under conditions and for a time sufficient to allow immunocomplexes to form Immunocomplexes formed between the ferroportin and antibodies in the biological sample that specifically bind to the ferroportin are then detected. A biological sample for use within such methods may be any sample obtained from a patient that is expected to contain ferroportin. Suitable biological samples include blood cells, other cells, and biopsy tissue samples, e.g. liver, spleen or duodenum. Suitable antibodies include antibodies from human cells, rodent, rabbit, goat, camel, or any other species.

The biological sample is incubated with antibodies in a reaction mixture under conditions and for a time sufficient to permit immunocomplexes to form between ferroportin and antibodies that are immunospecific for ferroportin. For example, a biological sample and one or more anti-ferroportin antibodies may be incubated at 4° C. for 24-48 hours.

Following the incubation, the reaction mixture is tested for the presence of immunocomplexes. Detection of immunocomplexes formed between an anti-ferroportin antibody and ferroportin present in the biological sample may be accomplished by a variety of known techniques, such as radioimmunoassays (RIA) and enzyme linked immunosorbent assays (ELISA). Suitable assays are well known in the art and are amply described in the scientific and patent literature (Harlow and Lane, 1988). Assays that may be used include, but are not limited to, the double monoclonal antibody sandwich immunoassay technique (U.S. Pat. No. 4,376,110); monoclonal-polyclonal antibody sandwich assays (Wide et al., 1970); the "western blot" method (U.S. Pat. No. 4,452,901); immunoprecipitation of labeled ligand (Brown et al., 1980); enzyme-linked immunosorbent assays (Raines and Ross, 1982); immunocytochemical techniques, including the use of fluorochromes (Brooks et al., 1980); and neutralization of activity (Bowen-Pope et al., 1984). Other immunoassays include, but are not limited to, those described in U.S. Pat. Nos. 3,817,827; 3,850,752; 3,901,654; 3,935,074; 3,984,533; 3,996,345; 4,034,074; and 4,098,876.

For detection purposes, an anti-ferroportin antibody may either be labeled or unlabeled. Unlabeled antibodies may be used in agglutination assays or in combination with labeled detection reagents that bind to the immunocomplexes (e.g., anti-immunoglobulin, Protein G, Protein A or a lectin and secondary antibodies, or antigen-binding fragments thereof, capable of binding to the antibodies that specifically bind to the ferroportin). If the anti-ferroportin antibody is labeled, the reporter group may be any suitable reporter group known in the art, including radioisotopes, fluorescent groups (e.g. fluorescein or rhodamine), luminescent groups, enzymes, biotin and dye particles. Labels that are themselves directly detectable include fluorescent or luminescent dyes, metals or metal chelates, electrochemical labels, radionuclides (e.g., 32P, 14C, 125I, 3H, or 131I), magnetic labels or beads (e.g., DYNABEADS), paramagnetic labels, or colorimetric labels (e.g., colloidal gold, colored glass or plastic beads). Such detectable labels may be directly conjugated to the anti-ferroportin antibody or detection reagent or may be associated with a bead or particle that is attached to the anti-ferroportin antibody or detection reagent. Labels that are detectable through binding of a labeled specific binding partner include biotin, digoxigenin, maltose, oligohistidine, 2,4-dinitrobenzene, phenylarsenate, ssDNA, or dsDNA). Indirect labels that can be indirectly detected by their production of a detectable reaction product include various enzymes well known in the art, such as alkaline phosphatase, horseradish peroxidase, β-galactosidase, xanthine oxidase, glucose oxidase or other saccharide oxidases, or luciferases, which cleave appropriate substrate to form a colored or fluorescent reaction product.

Within certain assays, an unlabeled anti-ferroportin antibody is immobilized on a solid support, for use as a "capture agent" (or reagent) that captures the ferroportin within a biological sample. The solid support may be any material known to those of ordinary skill in the art to which the antibody may be attached. For example, the solid support may be a test well in a microtiter plate or a nitrocellulose or other suitable membrane. Alternatively, the support may be a tube, bead, particle or disc, such as glass, fiberglass, latex or a plastic material such as polyethylene, polypropylene, polystyrene or polyvinylchloride or a porous matrix. Other materials include agarose, dextran, polyacrylamide, nylon, Sephadex, cellulose or polysaccharides. The support may also be a magnetic particle or a fiber optic sensor, such as those disclosed, for example, in U.S. Pat. No. 5,359,681. The immobilized anti-ferroportin antibody may be a polyclonal antibody, or one or more monoclonal antibodies such as those described herein, or a combination of polyclonal and one or more monoclonal antibodies. The antibody may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent) Immobilization by adsorption to a well in a microtiter plate or to a membrane is contemplated. In such cases, adsorption may be achieved by contacting the anti-ferroportin antibody, in a suitable buffer, with the solid support for a suitable amount of time. The contact time varies with temperature, but is typically between about 1 hour and about 1 day. In general, contacting a well of a plastic microtiter plate (including polystyrene or polyvinylchloride) with an amount of peptide ranging from about 10 ng to about 10 µg, and preferably about 100 ng to about 1 µg, is sufficient to immobilize an adequate amount of peptide.

Following immobilization, the remaining protein binding sites on the support are typically blocked. Any suitable blocking agent known to those of ordinary skill in the art, including bovine serum albumin, Tween™ 20™ (Sigma Chemical Co., St. Louis, Mo.), heat-inactivated normal goat serum (NGS), or BLOTTO (buffered solution of nonfat dry milk which also contains a preservative, salts, and an antifoaming agent) can be used. The support is then incubated with a biological sample suspected of containing ferroportin. The sample can be applied neat, or, more often, it can be diluted, usually in a buffered solution which contains a small amount (0.1%-5.0% by weight) of protein, such as BSA, NGS, or BLOTTO. In general, an appropriate contact time (i.e., incubation time) is a period of time that is sufficient to detect the presence of antibody or an antigen-binding fragment that is immunospecific for the ferroportin within a sample containing ferroportin. Preferably, the contact time is sufficient to achieve a level of binding that is at least about 95% of that achieved at equilibrium between bound and unbound antibody or antibody fragment. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween™ 20. A detection reagent that binds to the ferroportin in the immunocomplexes (formed by binding of the capture agent and the ferroportin from the sample) may then be added. Such detection reagent may be a polyclonal antibody, or one or more monoclonal antibodies such as those described herein, or a combination of polyclonal and one or more monoclonal antibodies such as those described herein or an antigen-binding fragment of any antibody. The detection reagent may be directly labeled, i.e., comprises at least a first detectable label or "reporter" molecule. Alternatively, the detection reagent may be an unlabeled anti-ferroportin antibody. This unlabeled anti-ferroportin (primary) antibody is then detected by the binding of a labeled secondary antibody or reagent to the primary antibody. For example, if the primary antibody is a murine immunoglobulin, the secondary antibody may be a labeled anti-murine immunoglobulin antibody. Similarly, if the primary antibody is a rabbit immunoglobulin, the secondary antibody may be a labeled anti-rabbit immunoglobulin antibody.

The detection reagent is incubated with the immunocomplex for an amount of time sufficient to detect the bound antibody or antigen-binding fragment thereof. An appropriate amount of time may generally be determined by assaying the level of binding that occurs over a period of time. Unbound label or detection reagent is then removed and bound label or detection reagent is detected using a suitable assay or analytical instrument. The method employed for detecting the reporter group depends upon the nature of the reporter group. For radioactive labels, scintillation counting or autoradiographic methods are generally appropriate. Spectroscopic methods may be used to detect dyes, luminescent or chemiluminescent moieties and various chromogens, fluorescent labels and such like. Biotin may be detected using avidin, coupled to a different reporter group (commonly a radioactive or fluorescent group or an enzyme). Enzyme reporter groups (including horseradish peroxidase, β-galactosidase, alkaline phosphatase and glucose oxidase) may generally be detected by the addition of substrate (generally for a specific period of time), followed by spectroscopic or other analysis of the reaction products. Regardless of the specific method employed, a level of bound detection reagent that is at least two fold greater than background (i.e., the level observed for a biological sample obtained from an individual with a normal level of ferroportin) indicates the presence of a disorder associated with expression of ferroportin.

In alternative embodiments, the sample and detection reagent may be contacted simultaneously with the capture agent, rather than sequentially added. In yet another alternative, the sample and detection reagent may be pre-incubated together, then added to the capture agent. Other variations are readily apparent to one of ordinary skill in the art.

In another embodiment, the amount of ferroportin present in a sample is determined by a competitive binding assay. Competitive binding assays rely on the ability of a labeled standard (e.g., a ferroportin polypeptide, or an immunologically reactive portion thereof) to compete with the test sample analyte (a ferroportin polypeptide) for binding with a limited amount of an anti-ferroportin antibody. Following separation of free and bound ferroportin, the ferroportin is quantitated by relating ratio of bound/unbound ferroportin to known standards. The amount of a ferroportin polypeptide in the test sample is inversely proportional to the amount of standard that becomes bound to the antibodies. To facilitate determining the amount of standard that becomes bound, the antibodies typically are immobilized on a solid support so that the standard and analyte that are bound to the antibodies may conveniently be separated from the standard and analyte which remain unbound. Thus, in such embodiments, the invention contemplates contacting a biological sample with labeled ferroportin (or a labeled fragment thereof that retains the antigenicity of ferroportin) and an antibody that binds to ferroportin, and detecting the amount of antibody-labeled ferroportin complex formed.

Preparation of conjugates to solid supports or detectable labels often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, whereas pyridyl disulfides react with sulfhydryls to produce mixed disulfides. The pyridyl disulfide product is cleavable. Imidoesters are also very useful for protein-protein cross-links.

Heterobifunctional cross-linkers possess two or more different reactive groups that allow for sequential conjugations with specific groups of proteins, minimizing undesirable polymerization or self-conjugation. Heterobifunctional reagents are also used when modification of amines is problematic Amines may sometimes be found at the active sites of macromolecules, and the modification of these may lead to the loss of activity. Other moieties such as sulfhydryls, carboxyls, phenols and carbohydrates may be more appropriate targets. A two-step strategy allows for the coupling of a protein that can tolerate the modification of its amines to a protein with other accessible groups. A variety of heterobifunctional cross-linkers, each combining different attributes for successful conjugation, are commercially available. Cross-linkers that are amine-reactive at one end and sulfhydryl-reactive at the other end are quite common. If using heterobifunctional reagents, the most labile group is typically reacted first to ensure effective cross-linking and avoid unwanted polymerization.

Disorders of iron homeostasis for which the detection or monitoring methods may be useful include african iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, cirrhosis of liver, classic hemochromatosis, collagen-induced arthritis (CIA), conditions with hepcidin excess (elevated hepcidin), congenital dyserythropoietic anemia, congestive heart failure, Crohn's disease, diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, gracile syndrome, *H. pyelori* infection or other bacterial infections, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hereditary hemochromatosis, HIV or other viral illnesses, Huntington's disease, hyperferritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, osteoarthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, Wilson's disease and/or cardiac disorders associated with iron overload.

During treatment with anti-ferroportin antibodies, the level of ferroportin on cells from the subject, e.g. in samples of blood cells or other cells or in biopsy tissue samples, can be monitored. Optionally samples may be taken pre-therapy, after commencement of treatment, and/or periodically during treatment.

VI. Therapeutic Uses For Anti-Ferroportin Antibodies

Also provided is the use of the antibodies described herein that bind ferroportin, to treat subjects in need thereof. In exemplary embodiments, the subject may be at risk of or suffering from a disorder of iron homeostasis, an elevated level of hepcidin, a hepcidin-related disorder, atherosclerosis or anemia.

As used herein, "treatment" or "treat" refers to both prophylactic treatment of a subject at risk of, or having a predisposition toward, a disease or disorder, and to therapeutic treatment of a subject suffering from a disease or disorder.

Administration of a therapeutic agent in a prophylactic method can occur prior to the manifestation of symptoms of an undesired disease or disorder, such that the disease or disorder is prevented or, alternatively, delayed in its progression. Thus, when used in conjunction with prophylactic methods, the term "therapeutically effective" means that, after treatment, a fewer number of subjects (on average) develop the undesired disease or disorder or progress in severity of symptoms.

When used in conjunction with therapeutic methods involving administration of a therapeutic agent after the subject manifests symptoms of a disease or disorder, the term "therapeutically effective" means that, after treatment, one or more signs or symptoms of the disease or disorder is ameliorated or eliminated.

"Mammal" for purposes of treatment refers to any animal classified as a mammal, including humans, domestic and farm animals, and zoo, sports, or pet animals, such as dogs, horses, cats, cows, etc. Preferably, the mammal is human.

As used herein, a "hepcidin-related disorder" refers to a condition caused by or associated with an abnormal level of hepcidin (e.g., hepcidin excess or hepcidin deficiency relative to the degree of iron stored) which disrupts iron homeostasis. A disruption in iron homeostasis can in turn result in secondary diseases such as anemia or atherosclerosis.

As used herein, the phrase "disease (or disorder) of iron homeostasis" refers to a condition in which a subject's iron levels require modulation. It includes ferroportin-related disorders, such as ferroportin disease and hereditary hemochromatosis type IV; conditions not associated with decreased levels of ferroportin that nevertheless would benefit from ferroportin preservation, hepcidin-related disorders; conditions not associated with elevated levels of hepcidin that nevertheless would benefit from inhibition of hepcidin activity or preservation of ferroportin activity, such as a disruption in iron homeostasis not caused by hepcidin; diseases where aberrant iron absorption, recycling, metabolism or excretion causes a disruption in normal iron blood levels or tissue distribution; diseases where iron dysregulation is a consequence of another disease or condition, such as inflammation, cancer or chemotherapy; diseases or disorders resulting from abnormal iron blood levels or tissue distribution; and diseases or disorders that can be treated by modulating iron levels or distribution. Non-limiting examples of such diseases or disorders of iron homeostasis, hepcidin-related disorders and inflammatory conditions which can result in hepcidin excess include african iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, cirrhosis of liver, classic hemochromatosis, collagen-induced arthritis (CIA), conditions with hepcidin excess (elevated hepcidin), congenital dyserythropoietic anemia, congestive heart failure, Crohn's disease, diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, gracile syndrome, *H. pylori* infection or other bacterial infections, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hereditary hemochromatosis, HIV or other viral illnesses, Huntington's disease, hyperferritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, osteoarthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, Wilson's disease, and/or cardiac disorders associated with iron overload.

Non-inflammatory conditions which are implicated in a disruption of iron regulation include, but are not limited to, vitamin B6 deficiency, vitamin B12 deficiency, folate deficiency, pellagra, funicular myelosis, pseudoencephalitis, Parkinson's disease (Fasano et al., J. Neurochem., 96:909 (2006) and Kaur et al., Ageing Res. Rev., 3:327 (2004)), Alzheimer's disease, coronary heart disease, osteopenia and osteoporosis (Guggenbuhl et al., Osteoporos. Int., 16:1809 (2005)), hemoglobinopathies and other disorders of red cell metabolism (Papanikolaou et al., Blood, 105:4103 (2005)), and peripheral occlusive arterial disease.

Various other iron indices and their normal ranges of concentrations are listed in Table 2.

| Iron Index | Normal Level (Range) |
|---|---|
| Serum iron | 50-170 µg/dL |
| Hemoglobin | 11.5-18 g/dL |
| Hematocrit | 37-54% |
| Red blood cell count (RBC) | 4.6-6.2 × $10^{12}$ cells/L (men) |
| | 4.25-5.4 × $10^{12}$ cells/L (women) |
| Mean Corpuscular Hemoglobin (MCH) | 27-32 pg |
| Mean Corpuscular Hemoglobin Concentration (MCHC) | 32-36% |
| Mean Corpuscular Volume (MCV) | 80-96 fL |
| Red Cell Distribution Width (RDW) | 11.5-14.5% (electrical impedance method) or 10.2-11.8% (laser light method) |
| Reticulocyte count | 18-158 × $10^9$ cells/L (0.8-2.5% in men; 0.8-4% in women) |
| Total Iron Binding Capacity (TIBC) | 250-450 µg/dL |
| Transferrin Iron Saturation Percentage (Tsat) | 15-50% |
| Ferritin | 12-120 µg/L |
| Folate | 3-16 ng/mL (serum) and 130-628 ng/mL (red blood cell) |
| Vitamin B12 | 200-900 pg/ml |

A patient's iron index level outside of the normal ranges listed in Table 2 indicates that the patient may benefit from treatment with an anti-ferroportin antibody. Since ferroportin is the receptor for hepcidin, which plays a key role in iron homeostasis, in some embodiments of the invention hepcidin levels and activity will correlate with a disruption of iron homeostasis and/or iron indices. In some embodiments, elevated hepcidin levels correlate with serum iron levels below the normal ranges indicated in Table 2, low hemoglobin, and hematocrit, reduced or normal Tsat and high or normal ferritin values, and elevated inflammatory status as measured by C-reactive protein (CRP) elevation or other markers of inflammation.

As used herein, the phrase "therapeutically effective amount" of an anti-ferroportin antibody refers to an amount that results in the desired therapeutic effect (i.e. that provides "therapeutic efficacy"). Exemplary therapeutic effects include increased circulating iron levels or increased iron availability, increased red blood cell count, increased red blood cell mean cell volume, increased red blood cell hemoglobin content, increased hemoglobin (e.g., increased by ≥0.5 g/dL), increased hematocrit, increased Tsat, increased reticulocyte count, increased or normalized reticulocyte mean cell volume, increased reticulocyte hemoglobin content, or normalization of any of the parameters described above. Returning such a parameter to its normal range is not required for therapeutic efficacy; for example, a measurable change (increase or reduction) in the direction of normal can be considered to be a desired therapeutic effect by a clinician. When applied to an individual active ingredient, administered alone, the term refers to that ingredient alone. When applied to a combination, the term refers to combined amounts of the active ingredients that result in the therapeutic effect, whether administered in combination, serially or simultaneously. For example, in aspects where the anti-ferroportin antibody is administered in conjunction with an erythropoiesis stimulator, a therapeutically effective amount is meant to refer to the combined amount that increases or normalizes any of the parameters stated above.

The compositions for and methods of treatment described herein may utilize one or more anti-ferroportin antibodies used singularly or in combination with other therapeutic agents to achieve the desired effects.

In some embodiments, potential patient populations for the treatment of disorders of iron homeostasis are first identified by evaluating the level of hepcidin in a biological sample. A patient identified as having elevated levels of hepcidin would be considered as a candidate for treatment with the anti-ferroportin antibodies disclosed herein. In exemplary embodiments, a biological sample is isolated from a patient and is incubated with one or more anti-hepcidin antibodies. The level of the antibody-hepcidin complex above a threshold typical for the standard population is considered an elevated level of hepcidin. Hepcidin antibodies suitable for use in this method are disclosed in co-owned U.S. Provisional Patent Application Nos. 60/888,059 and 61/015,138, the disclosure of which are incorporated herein by reference in their entireties. In other exemplary embodiments, hepcidin levels are determined by mass spectrometry techniques described in co-owned U.S. patent application Ser. No. 11/880,313 and International Patent Application No. PCT/US2007/016477, the disclosures of which are incorporated herein by reference in their entirety. When such mass spectrometry techniques are used, an elevated level of hepcidin in a biological sample is generally greater than 10 ng/ml, but will vary depending on the assay and depending on the subset of population tested.

In some embodiments, therapy with an anti-ferroportin antibody may include monitoring changes in the level of hepcidin in a subject such as a human patient. Methods in which hepcidin levels are monitored may comprise (a) incubating a first biological sample, obtained from a patient prior to anti-ferroportin antibody therapy with one or more of anti-hepcidin antibodies or antigen-binding fragments thereof wherein the incubation is performed under conditions and for a time sufficient to allow immunocomplexes to form; (b) detecting immunocomplexes formed between the hepcidin in the biological sample and antibodies or antigen-binding fragments thereof; and optionally (c) repeating steps (a) and (b) using a second biological sample taken from the patient at later time, such as for example, following therapy with one or more of the anti-ferroportin antibodies; and (d) comparing the number of immunocomplexes detected in the first and second biological samples. An increase in the number of immunocomplexes in the second sample relative to the first sample indicates an increase in hepcidin levels. A biological sample for use within such monitoring methods may be any sample obtained from a patient that would be expected to contain hepcidin. Exemplary biological samples include blood, plasma, sera, urine and bone marrow. A first biological sample may be obtained prior to initiation of therapy or part way through a therapy regime. The second biological sample should be obtained in a similar manner, but at a time following additional therapy. The second biological sample may be obtained at the completion of, or part way through, therapy, provided that at least a portion of therapy takes place between the isolation of the first and second biological samples. Incubation and detection procedures for both samples may generally be performed as described in co-owned U.S. Provisional Patent Application Nos. 60/888,059 and 61/015,138, the disclosure of which are incorporated herein by reference in their entireties.

VII. Combination Therapy

It may be further advantageous to mix two or more antibodies together (which bind to the same or different target antigens) or to co-administer an antibody described herein with a second therapeutic agent to provide still improved efficacy. In some embodiments, the methods described herein comprise the administration of two or more anti-ferroportin antibodies. In some embodiments, the methods described herein comprise the administration of one or more anti-ferroportin antibodies and optionally the administration of one or more anti-hepcidin antibodies. Anti-hepcidin monoclonal antibodies have been described in U.S. Provisional Application Ser. Nos. 60/888,059 and 61/015,138, filed Feb. 2, 2007 and Dec. 19, 2007, respectively, the disclosures of which are incorporated herein by reference in their entireties.

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In exemplary embodiments, the methods of the invention include the administration of single antibodies, as well as combinations, or "cocktails", of different antibodies. Such antibody cocktails may have certain advantages inasmuch as they contain antibodies which exploit different effector mechanisms. Such antibodies in combination may exhibit synergistic therapeutic effects.

Combination therapy using an anti-ferroportin antibody and an erythropoiesis stimulator is specifically contemplated. In various embodiments, anti-ferroportin antibodies and erythropoiesis stimulators can be used to improve treatment of a patient with anemia. In particular, patients who are hypo-responsive to, including unresponsive to, erythropoiesis stimulator therapy, such as erythropoietin or analogs thereof (Epoetin alfa, Epoetin beta, darbepoetin alfa), among others, will benefit from co-treatment with an anti-ferroportin antibody. In one embodiment, combination therapy includes treatment with at least one antibody that binds to human ferroportin and at least one erythropoiesis stimulator. In another embodiment, combination therapy includes treatment with at least one antibody that binds to human ferroportin, at least one antibody that binds to human hepcidin and at least one erythropoiesis stimulator.

Combination therapy using an anti-ferroportin antibody and an iron chelator to redistribute or reduce iron stores in the body is also contemplated. An iron chelator is an agent capable of binding iron and removing it from a tissue or from circulation. Examples include deferoxamine (Desferal®) and deferasirox (Exjade®), and deferiprone (1,2-dimethyl-3-hydroxypyridin-4-one). In some embodiments, ferroportin antibodies and erythropoiesis stimulators can be used to improve treatment of a patient having an iron loading disorder secondary to transfusion-dependent iron overload, or having an iron maldistribution disorder, such as Friedreich's ataxia.

Combination therapy using an anti-ferroportin antibody and a phlebotomy is also contemplated. Such combination therapy can be used to improve treatment of a patient having an iron overload disorder, such as hemochromatosis.

As used herein, "erythropoiesis stimulator" means a chemical compound that directly or indirectly causes activation of the erythropoietin receptor, for example, by binding to and causing a conformational change of the receptor or by stimulating endogenous erythropoietin expression. Erythropoiesis stimulators include erythropoietin and variants, analogs, or derivatives thereof that bind to and activate erythropoietin receptor; antibodies that bind to erythropoietin receptor and activate the receptor; or peptides that bind to and activate erythropoietin receptor; or small organic chemical compounds, optionally less than about 1000 Daltons in molecular weight, that bind to and activate erythropoietin receptor. Erythropoiesis stimulators include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP 1/hematide), mimetic antibodies and HIF inhibitors (see U.S. Patent Publication No. 2005/0020487, the disclosure of which is incorporated by reference in its entirety). Exemplary erythropoiesis stimulators include erythropoietin, darbepoetin, erythropoietin agonist variants, and peptides or antibodies that bind and activate erythropoietin receptor (and include compounds reported in U.S. Patent Application Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; 7,217,689; PCT publication nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and US publication nos. US 2002/0155998; US 2003/0077753; US 2003/0082749; US 2003/0143202; US 2004/0009902; US 2004/0071694; US 2004/0091961; US 2004/0143857; US 2004/0157293; US 2004/0175379; US 2004/0175824; US 2004/0229318; US 2004/0248815; US 2004/0266690; US 2005/0019914; US 2005/0026834; US 2005/0096461; US 2005/0107297; US 2005/0107591; US 2005/0124045; US 2005/0124564; US 2005/0137329; US 2005/0142642; US 2005/0143292; US 2005/0153879; US 2005/0158822; US 2005/0158832; US 2005/0170457; US 2005/0181359; US 2005/0181482; US 2005/0192211; US 2005/0202538; US 2005/0227289; US 2005/0244409; US 2006/0088906; and US 2006/0111279.

Erythropoietin includes, but is not limited to, a polypeptide comprising the amino acid sequence as set forth in SEQ ID NO: 21. Amino acids 1 through 165 of SEQ ID NO: 21 constitute the mature protein of any molecules designated as an epoetin, e.g., epoetin alfa, epoetin beta, epoetin delta, epoetin omega, epoetin iota, epoetin gamma, epoetin zeta, and the like. Additionally, an epoetin also includes any of the aforementioned epoetin which are chemically modified, e.g., with one or more water-soluble polymers such as, e.g., polyethylene glycol (including PEG-EPO-beta). Also contemplated are analogs of erythropoietin, with 65%, 70%, 75%, 80%, 85%, 90%, 91%, 92%, 93%, 94%, 95%, 96%, 97%, 98%, or 99% identity to SEQ. ID NO: 21 still retaining erythropoietic activity.

Exemplary sequences, manufacture, purification and use of recombinant human erythropoietin are described in a number of patent publications, including but not limited to Lin U.S. Pat. No. 4,703,008 and Lai et al. U.S. Pat. No. 4,667,016, each of which is incorporated herein by reference in its entirety. Darbepoetin is a hyperglycosylated erythropoietin analog having five changes in the amino acid sequence of rHuEPO which provide for two additional carbohydrate chains. More specifically, darbepoetin alfa contains two additional N-linked carbohydrate chains at amino acid residues 30 and 88 of SEQ ID NO: 21. Exemplary sequences, manufacture, purification and use of darbepoetin and other erythropoietin analogs are described in a number of patent publications, including Strickland et al., 91/05867, Elliott et al., WO 95/05465, Egrie et al., WO 00/24893, and Egrie et al. WO 01/81405, each of which is incorporated herein by reference in its entirety. Derivatives of naturally occurring or analog polypeptides include those which have been chemically modified, for example, to attach water soluble polymers (e.g., pegylated), radionuclides, or other diagnostic or targeting or therapeutic moieties.

The term "erythropoietic activity" means activity to stimulate erythropoiesis as demonstrated in an in vivo assay, for example, the exhypoxic polycythemic mouse assay (See, e.g., Cotes and Bangham, Nature 191:1065, 1961).

VIII. Administration and Preparation of Pharmaceutical Formulations

In some embodiments, the ferroportin antibodies used in the practice of a method described herein may be formulated into pharmaceutical compositions comprising a carrier suitable for the desired delivery method. Suitable carriers include any material which, when combined with a ferroportin antibody, retains the high-affinity binding of ferroportin and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary antibody concentrations in the formulation may range from about 0.1 mg/ml to about 180 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antibody may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g., sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the antibody, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the antibody formulation to reduce aggregation of the formulated antibody and/or minimize the formation of particulates in the formulation and/or reduce adsorption. Exemplary surfactants include nonionic surfactants such as polysorbates (e.g., polysorbate 20, or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. antibody, buffer, polyol and surfactant) and is essentially free of one or more preservatives, such as benzyl alcohol, phenol, m-cresol, chlorobutanol and benzethonium Cl. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g., Zn-protein complexes); biodegradable polymers such as polyesters; and/or salt-forming counterions such as sodium.

Therapeutic formulations of the ferroportin antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In one embodiment, a suitable formulation contains an isotonic buffer such as a phosphate, acetate, or TRIS buffer in combination with a tonicity agent such as a polyol, Sorbitol, sucrose or sodium chloride which tonicifies and stabilizes. One example of such a tonicity agent is 5% Sorbitol or sucrose. In addition, the formulation could optionally include a surfactant such as to prevent aggregation and for stabilization at 0.01 to 0.02% wt/vol. The pH of the formulation may range from 4.5-6.5 or 4.5-5.5. Other exemplary descriptions of pharmaceutical formulations for antibodies may be found in US 2003/0113316 and U.S. Pat. No. 6,171,586, each incorporated herein by reference in its entirety.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Suspensions and crystal forms of antibodies are also contemplated. Methods to make suspensions and crystal forms are known to one of skill in the art.

The formulations to be used for in vivo administration must be sterile. In some embodiments, the compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, Journal of Parenteral Science and Technology, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, Drug Development and Industrial Pharmacy, Volume 18, Numbers 11 and 12, pages 1311-1354 (1992).

Excipients have been noted in some cases to act as stabilizers for freeze-dried products; Carpenter et al., Developments in Biological Standardization, Volume 74, pages 225-239 (1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and disaccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In some embodiments, the formulations of the invention may be designed to be short-acting, fast-releasing, long-acting, or sustained-releasing as described herein. Thus, the pharmaceutical formulations may also be formulated for controlled release or for slow release.

Therapeutically effective amounts of a composition will vary and depend on the severity of the disease and the weight and general state of the subject being treated, but generally range from about 1.0 µg/kg to about 100 mg/kg body weight, or about 10 µg/kg to about 30 mg/kg, or about 0.1 mg/kg to about 10 mg/kg or about 1 mg/kg to about 10 mg/kg per application. Administration can be daily, on alternating days, weekly, twice a month, monthly or more or less frequently, as necessary depending on the response to the disorder or condition and the subject's tolerance of the therapy. Maintenance dosages over a longer period of time, such as 4, 5, 6, 7, 8, 10 or 12 weeks or longer may be needed until a desired suppression of disorder symptoms occurs, and dosages may be adjusted as necessary. The progress of this therapy is easily monitored by conventional techniques and assays.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The anti-ferroportin antibody or specific binding agent is administered by any suitable means, either systemically or locally, including via parenteral, subcutaneous, intraperitoneal, intrapulmonary, and intranasal, and, if desired for local treatment, intralesional administration. Parenteral routes include intravenous, intraarterial, intraperitoneal, epidural, intrathecal administration. In addition, the specific binding agent or antibody is suitably administered by pulse infusion, particularly with declining doses of the specific binding agent or antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g., through a catheter placed close to the desired site. In some embodiments, the specific binding agent or antibody of the invention is administered intravenously in a physiological solution at a dose ranging between 0.01 mg/kg to 100 mg/kg at a frequency ranging from daily to weekly to monthly (e.g., every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

IX. Detection Kits and Therapeutic Kits

As a matter of convenience, an antibody or specific binding agent disclosed herein can be provided in a kit, i.e., a packaged combination of reagents in predetermined amounts with instructions for performing the diagnostic or detection assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiment, the signal generating means may come pre-associated with an antibody of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. Preferably, an enzyme that catalyzes the formation of a chemiluminescent or chromogenic product or the reduction of a chemiluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising an anti-ferroportin antibody and an erythropoiesis stimulator packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating a disorder of iron homeostasis and comprises an anti-ferroportin antibody and an erythropoiesis stimulator. The kit may optionally further include iron for oral or parenteral, e.g., intravenous, administration. In another aspect, the kit comprises an anti-ferroportin antibody and a label attached to or packaged with the container describing use of the anti-ferroportin antibody with an erythropoiesis stimulator. In yet another aspect, the kit comprises an erythropoiesis stimulator and a label attached to or packaged with the container describing use of the erythropoiesis stimulator with an anti-ferroportin antibody. In certain embodiments, an anti-ferroportin antibody and an erythropoiesis stimulator, and optionally the iron, are in separate vials or are combined together in the same pharmaceutical composition. In yet another aspect, an anti-ferroportin antibody is combined with iron in a single pharmaceutical composition. In yet another embodiment, the erythropoiesis stimulator is combined with iron in a single pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein may also be prepared that comprise at least one of the antibody, peptide, antigen-binding fragment, or polynucleotide disclosed herein and instructions for using the composition as a detection reagent or therapeutic agent. Containers for use in such kits may typically comprise at least one vial, test tube, flask, bottle, syringe or other suitable container, into which one or more of the detection and/or therapeutic composition(s) may be placed, and preferably suitably aliquoted. Where a second therapeutic agent is also provided, the kit may also contain a second distinct container into which this second detection and/or therapeutic composition may be placed. Alternatively, a plurality of compounds may be prepared in a single pharmaceutical composition, and may be packaged in a single container means, such as a vial, flask, syringe, bottle, or other suitable single container. The kits of the present invention will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In related embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, mini-computers, mainframe computers, distributed computing environments that include any of the above systems or devices, or any other systems known in the art.

X. Non-Therapeutic Uses for Ferroportin Antibodies

The antibodies disclosed herein may be used as affinity purification agents for target antigen or in diagnostic assays for target antigen, e.g., detecting its expression in specific cells (e.g., blood cells) or tissues. The antibodies may also be used for in vivo diagnostic assays. Generally, for these purposes the antibody is labeled with a radionuclide (such as $^{111}$In, $^{99}$Tc, $^{14}$C, $^{131}$I, $^{125}$I, $^{3}$H, $^{32}$P or $^{35}$S) so that the site can be localized using immunoscintigraphy.

The antibodies disclosed herein may be employed in any known assay method, such as competitive binding assays, direct and indirect sandwich assays, such as ELISAs, and immunoprecipitation assays. Zola, Monoclonal Antibodies: A Manual of Techniques, pp. 147-158 (CRC Press, Inc. 1987); Zola, Heddy. Monoclonal Antibodies The Second Generation. Oxford: BIOS Scientific Publishers, 1995 and Zola, Heddy. Monoclonal Antibodies Preparation and Use of Monoclonal Antibodies and Engineered Antibody Derivatives. Oxford: BIOS, 2000. The antibodies may also be used for immunohistochemistry, to label cell samples using methods known in the art.

XI. Examples

Example 1—Production of Anti-Ferroportin Monoclonal Antibodies by Genetic Immunization A viral vector for expression of human ferroportin (hFpn) was constructed by fusing DNA encoding the PADRE peptide, AKFVAAWTLKAAA (SEQ ID NO: 24), in frame to 3' terminus of the human ferroportin cDNA (SEQ ID NO: 15) after deleting its termination codon. The resulting DNA encoding the hFpn-PADRE fusion was inserted into a pAd/CMV/V5-DEST gateway adenoviral vector (Invitrogen V493-20, Carlsbad, Calif.) by LR recombination reaction. The adenoviral vector was amplified in 293T cells, purified by CsCl gradient centrifugation, and titered by Adeno-X Rapid Titer Kit (Cat No 631028, BD Biosciences, CA).

A DNA fragment encoding the hFpn-PADRE fusion was also inserted into phCMV1 (P003100, Gene Therapy Systems, San Diego, Calif.), and the resulting plasmid DNA was used for DNA boosting via electroporation. Plasmid DNAs for mice immunization were purified by using QIAGEN EndoFree Plasmid Mega kit (QIAGEN, Valencia, Calif.).

Membrane preparations from 293E6 cells expressing human ferroportin-PADRE were generated by introducing human ferroportin-PADRE DNA into $1.1 \times 10^7$ 293E6 cells using standard transfection techniques. Cells were pelleted after 48 hours and resuspended in the presence of protease inhibitors in a hypotonic buffer (10 mM HEPES pH 7.4, 1 mM MgCl2). Cells were mechanically lysed and the membranes were separated from the remaining cell debris using a sucrose gradient Five to 6 week-old C57Bl/6 mice were purchased from Charles Liver Laboratory. For recombinant adenovirus, rAd/CMV-hFpn-PADRE, injection, mice were anesthetized with Isoflurane (Abbott, Ill.) and intradermally injected with 50 µl of $2 \times 10^9$ i.f.u. (infectious unit) into single site. Mice were boosted 3 times with plasmid DNA electroporation. For DNA electroporation, mice were anesthetized with Isoflurane, saved, and intradermally injected with 50 µl of 50 µg of phCMV-hFpn-PADRE in saline and followed by electroporation. Electroporation was carried out by using BTX830 (BTX Inc., San Diego, Calif.) and tweezertrodes. Mice received 4 discontinuous pulses, 200 ms each, and tweezertrodes were reversed and the other set of pulses was given. Each immunization was given at every 3 weeks. Five days prior to fusion, mice were given a final boost with 200 μg of the hFpn-PADRE membrane preparation.

Spleens from two mice were harvested and the resulting hybridoma supernatants were screened first for ferroportin binding using ferroportin-expressing cells (Example 3) and second for function (preservation of ferroportin iron efflux activity) using an iron response assay (Example 5). Approximately 4000 supernatants were screened and of these, only 33 antibodies were found to bind ferroportin and of these, only one, 31A5, provided ferroportin preservation in the presence of hepcidin.

Example 2—Production of Other Anti-Ferroportin Antibodies

Additional anti-ferroportin antibodies were generated as follows. Xenomouse™ IgG2κλ and IgG4 κλ mice were immunized with either ferroportin-expressing cells or membranes from ferroportin-expressing cells. Briefly, IgG4 κλ and IgG2 κλ mice were immunized with 293T cells transiently expressing ferroportin or with membrane preparations from 293E6 cells expressing ferroportin. Antigens were delivered either subcutaneously or via the peritoneal cavity. Mice were boosted using aliquots of the initial antigen until anti-ferroportin antibodies were detectable in the serum. Mice with the highest anti-ferroportin titers were harvested and hybridomas were first screened for ferroportin binding using ferroportin-expressing cells (Example 4) and second were screened for function (preservation of ferroportin iron efflux activity) using an iron response assay (Example 5).

A summary of the various antibody campaigns is set forth in Table 3. It is clear that the generation of antibodies that provide ferroportin preservation is not a property shared by all ferroportin antibodies. The antibodies produced by the traditional immunization of Xenomouse included 37A2 (FIG. 8E and SEQ ID NOs: 25-34), 37B9 (FIG. 8D and SEQ ID NOs: 35-44), 37C8 (FIG. 8D and SEQ ID NOs: 45-54), 37G8 (FIG. 8C and SEQ ID NOs: 55-64), 38A4 (FIG. 8C and SEQ ID NOs: 65-74), 38C8 (FIG. 8B and SEQ ID NOs: 75-84) 38D2 (FIG. 8B and SEQ ID NOs: 85-94), 38E3 (FIG. 8A and SEQ ID NOs: 95-104) and 38G6 (FIG. 8A and SEQ ID NOs: 105-114).

| Human Ferroportin (Fpn) Antibody Campaigns | Supernatants Screened | Fpn-binding Antibodies | Potentially Fpn-Protecting Antibodies |
|---|---|---|---|
| Genetic Immunization of mice | 4000 | 37 | 1 |
| Traditional Immunization of XENOMOUSE ™ | 7600 | 200 | 11 |

Example 3—Characterization of Anti-Ferroportin Monoclonal Antibodies

To confirm the specificity of 31A5 for ferroportin, Western analysis was performed using membrane preparations from ferroportin-expressing cells.

Approximately 5 μg of crude membrane preparation from either ferroportin-expressing 293T or wild-type 293T cells were subjected to gel electrophoresis and transferred to a nitrocellulose membrane and probed with either 500 ng/mL 31A5 or 2 μg/mL rabbit anti-ferroportin peptide polyclonal antibody followed by either an anti-mouse or anti-rabbit secondary, respectively. The polyclonal antiserum was generated by immunization with a ferroportin peptide spanning residues 247-265 of SEQ ID NO: 16 and purified with the same peptide.

31A5 recognized a band that migrates at the predicted molecular mass of ferroportin, approximately 63 kDa, and is similar to that detected by a positive control antiserum raised against a ferroportin peptide. Both prominent bands recognized by 31A5 were predicted to be ferroportin, which often appears as a doublet (de Domenico et al., Proc. Natl. Acad. Sci. USA, 102:8955-8960, 2005). Of the other 31 anti-ferroportin antibodies identified, fewer than 10 recognized ferroportin by Western blot analysis and none of those 10 preserved ferroportin iron export activity in the presence of hepcidin.

31A5 was then tested by Western analysis for its ability to recognize a panel of ferroportin peptide-Fc conjugates, where the peptide moiety was derived from different, non-overlapping regions of the ferroportin sequence. 500 ng of ferroportin peptide Fc conjugates 1-5 (Peptide 1: LGAIIGD-WVDKNARLKVAQTSL, amino acids 75-96 of SEQ ID NO: 16; Peptide 2: ITIQRDWIVVVAGEDRSKLANM-NATIRRIDQL, amino acids 152-183 of SEQ ID NO: 16; Peptide 3: GYAYTQGLS, amino acids 330-338 of SEQ ID NO: 16; Peptide 4: MPGSPLDLSVSPFEDIRSRFIQGES-ITPTKIPEITTEIYMSNGSNSANIVPETS, amino acids 393-446 of SEQ ID NO: 16; and Peptide 5: AQNTLGNKL-FACGPDAKEVRKENQANTSVV, amino acids: 542-571 of SEQ ID NO: 16) were run on a NuPAGE 4-12% gel, transferred to a nitrocellulose membrane and probed using 200 mg/mL 31A5 followed by an anti-mouse secondary antibody.

Figure 2:
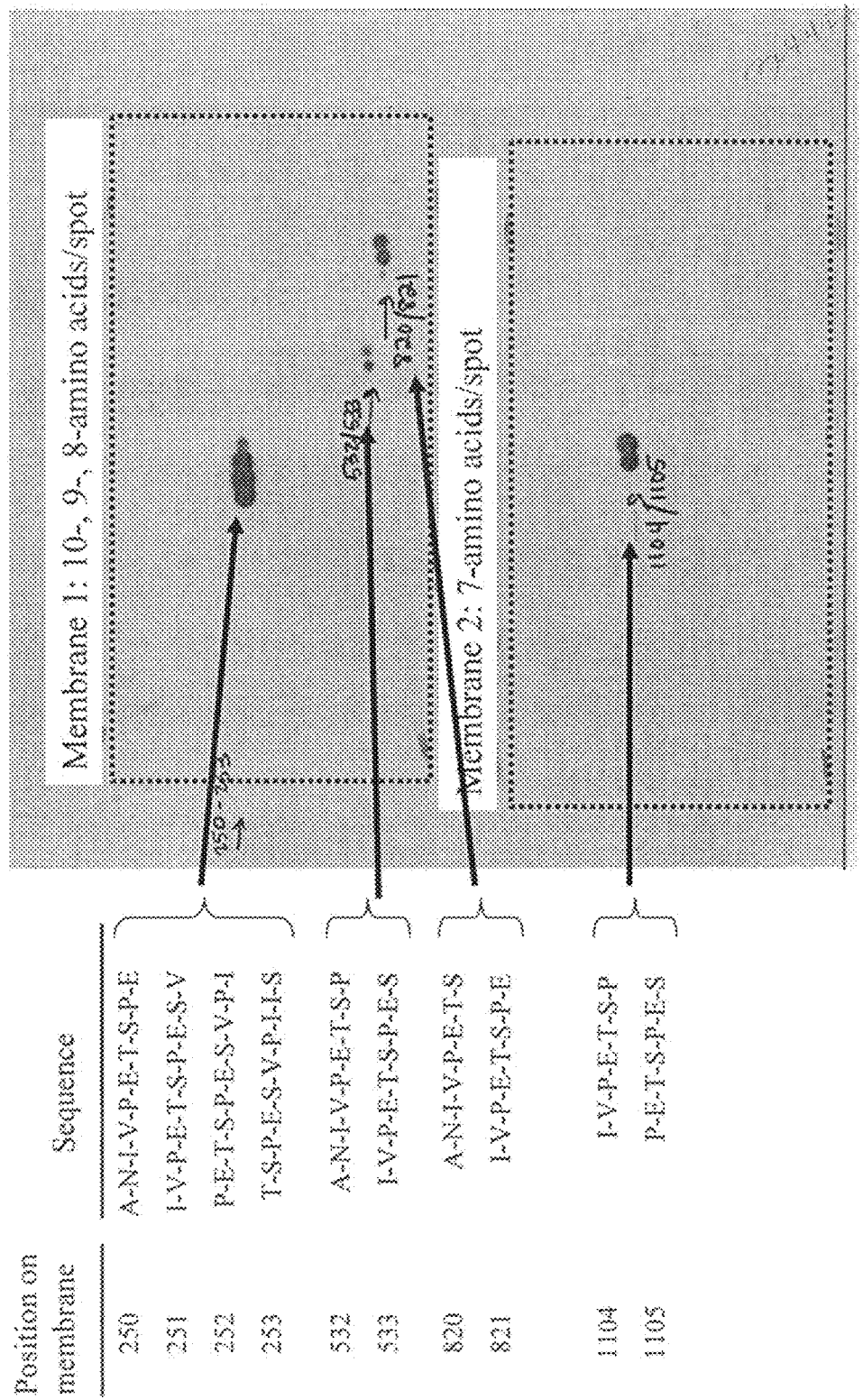
FIG. 2 shows that anti-ferroportin antibody 31A5 recognizes the ferroportin peptide sequence (ANIVPETSPES, residues 439-449 of SEQ ID NO: 16).

31A5 showed significant binding to only one of the 5 peptides tested, Peptide 4 comprising ferroportin residues 393-446 of SEQ ID NO: 16. None of the other ferroportin-binding antibodies bound appreciably to this peptide. The location of the 31A5 epitope was further narrowed by detecting binding to ferroportin peptides ranging in length from 7 to 10 amino acids immobilized on a cellulose membrane. From these binding studies, the 31A5 epitope was determined to be within the peptide sequence: ANIV-PETPES (ferroportin residues 439-449 of SEQ ID NO: 16) (FIG. 2). Residue cysteine 326 has recently been shown to be a component of the hepcidin binding site (Nemeth et al., International Biolron Society Program Book and Abstracts, 2007: p. 28 and de Domenico et al. Cell Metab., 8: 146-156, 2008). Cysteine residue 326 of SEQ ID NO: 16 is located in a different extracellular loop from the loop containing the 31A5 epitope (i.e., loop 3 of FIG. 1A).

Example 4—Characterization of Human Anti-Ferroportin Antibodies

The following Example describes the epitope mapping for human antibodies 37A2, 37B9, 37C8, 37G8, 38A4, 38C8, 38D2, 38E3 and 38G6.

The PepSpot technique (Heiskanen et al., Virology, 262: 321-332, 1999) was used to identify the binding epitopes on ferroportin for human antibodies 37A2, 37B9, 37C8, 37G8, 38A4, 38C8, 38D2, 38E3 and 38G6. Briefly, an array of overlapping 10-mer peptides was synthesized on a cellulose membrane by a solid phase peptide synthesis spotting method. These peptide sequences were derived from amino acids 1-571 of SEQ ID NO: 16. The array was then soaked in 0.05% Tween-20/PBS (PBS-T), blocked with 5% BSA in PBS-T for 3 hours at room temperature and subsequently washed three times with PBS-T. The prepared array was then incubated for 90 minutes at room temperature with 1 µg/mL solution of antibodies 37A2, 37B9, 37C8, 37G8, 38A4, 38C8, 38D2, 38E3 or 38G6 in 5% nonfat dry milk. After binding, the membrane was washed three times with PBS-T and subsequently incubated for 1 hour at room temperature with a goat anti-human light chain antibody conjugated to horseradish peroxidase diluted 1:50,000 in 5% nonfat dry milk. The membrane was then washed three times with PBS-T and any binding was determined using chemiluminescence detection on X-ray film.

Antibodies 37A2, 37B9, 37C8, 37G8, 38A4, 38C8, 38D2, 38E3 and 38G6 bound to epitopes within, overlapping or near loops 1, 2, 3 and 4 of the ferroportin sequence set forth in FIG. 1A. In particular, 37A2 recognized a fragment of ferroportin that comprises amino acids SITPTKIPEI (amino acids 417-426 of SEQ ID NO: 16); all of 37B9, 37C8, 37G8, 38C8 and 38E3 recognized fragments of ferroportin comprising amino acids AFLYMTVLGF (amino acids 315-324 of SEQ ID NO: 16); 38A4 recognized fragments of ferroportin comprising amino acids ITTEIYMSNGSNS (amino acids 426-438 of SEQ ID NO: 16); 38G6 recognized fragments of ferroportin comprising amino acids TEIYMSNGSNSA (amino acids 428-439 of SEQ ID NO: 16) and 38D2 recognized fragments of ferroportin comprising amino acids YHGWVLTSCY (amino acids 124-133 of SEQ ID NO: 16) and amino acids RDGWVSYYNQ (amino acids 296-305 of SEQ ID NO: 16). Residue cysteine 326 of SEQ ID NO; 16 has recently been shown to be a component of the hepcidin binding site (Nemeth et al., International Biolron Society Program Book and Abstracts, 2007: p. 28; de Domenico et al., Proc. Natl. Acad. Sci. USA, 102:8955-8960, 2005). Cysteine residue 326 of SEQ ID NO: 16 is located in a different extracellular loop, loop 3, compared to the loops containing the 37A2, 37B9, 37C8, 37G8, 38A4, 38C8, 38D2, 38E3 and 38G6 epitopes.

FIG. 9 shows the epitopes recognized by the various anti-ferroportin antibodies disclosed herein.

Example 5—An Anti-Ferroportin Antibody Preserves Ferroportin Iron Export Activity in an In Vitro Iron Response Assay This assay allows detection of intracellular iron levels through monitoring the activity of a beta lactamase reporter gene fused to the ferritin iron response element. Low levels of intracellular iron in ferroportin-expressing cells are indicative of active ferroportin, while high levels of intracellular iron are indicative of reduced ferroportin activity. Hepcidin causes ferroportin to be internalized and removed from the cell surface, thus inhibiting release of iron and raising intracellular iron concentrations. The effect of anti-human ferroportin antibodies on this iron sequestration was evaluated in vitro.

Figure 3:
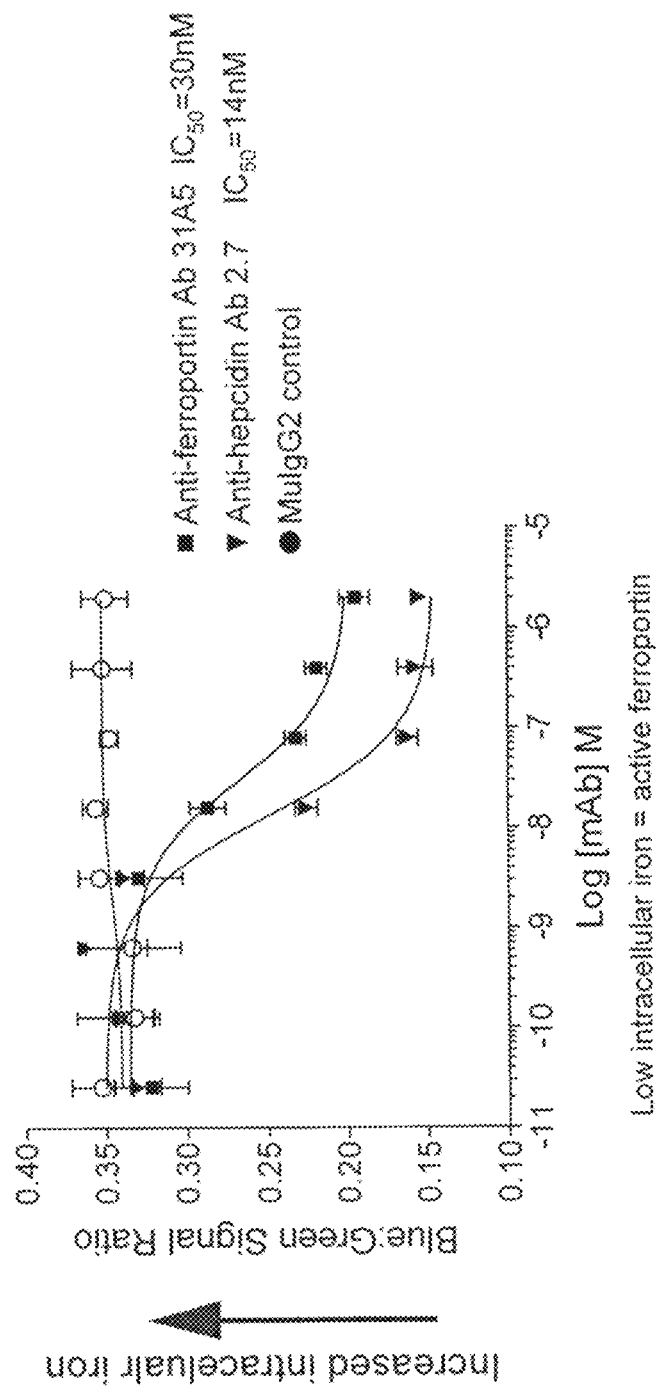
FIG. 3 shows that anti-ferroportin antibody 31A5 preserves ferroportin iron export activity in an in vitro iron response assay.

A 293 cell line containing a doxycycline-inducible ferroportin (Fpn) expression construct as well as a beta-lactamase (BLA) expression construct containing one copy of the 5' iron response element (IRE) from ferritin having the following nucleotide sequence (tcggccccgcctcctgccaccgcagat-tggccgctagccctccccgagcgccctgcctccgagggccggcgcac-cataaaagaa gccgccctagccacgtcccctcgcagttcggcggtcccgcgggtctgtctcttgct-tcaacagtgtttggacggaacagatccgggga ctctatccagcctccgaccgc-cctccgatttcctctccgcttgcaacctccgggaccatcttctcggccatctcct-gatctgggacctgc cagcaccgttttgtggttagctccttcttgccaacc) (SEQ ID NO: 23) that regulate mRNA translation was constructed. These 293/Fpn/BLA cells, taken from a 70-80% confluent culture, were plated at 2.8×10$^5$ cells/mL in DMEM (Invitrogen Cat#11965) 5% FBS (Invitrogen Cat#10099-141) and PSQ ((penicillin, streptomycin, glutamine solution, Invitrogen Cat#10378-016), 90 µL/well (25,000 cells/well) in Bio-Coat Poly-D Lysine coated plates (Becton-Dickinson Cat#35-6640) and incubated at 37° C. with 5% $CO_2$. At the end of the same day, a solution of assay medium (DMEM, 5% FBS, PSQ) with 100 µg/mL doxycycline was made, 10 uL/well of it added to the plate, and the plate incubated overnight or for at least 20 hours. The next day, media was removed from the wells and replaced with premade mixes of DMEM 5% FBS PSQ, 2.5 µg/mL ferric citrate, 36 nM synthetic human hepcidin and serial dilutions of the antibodies (2.7:mouse anti-human hepcidin antibody; 31A5: mouse anti-human ferroportin antibody) and mouse IgG2 control antibody), all prepared in a 96-well polypropylene deep-well block plate immediately before addition to the assay plate. Mixtures were added at 100 µL/well and incubated overnight at 37° C., 5% $CO_2$ in a cell culture incubator. Plates were then removed from the incubator and equilibrated to room temperature for 10 minutes before adding 20 µL/well of the prepared Invitrogen GeneBlazer CCF4 A/M development reagent (Invitrogen Kit# K1085) and incubating for 90 minutes in the dark. Development reagent was also added to 16 wells of a control assay plate without cells containing 100 µL assay medium (DMEM 5% FBS PSQ) and incubated for the same time. Blue and green fluorescence signals were then read on an Envision Multilabel Reader (Perkin-Elmer Inc.) by exciting at 409 nm and reading emissions at 447 nm (blue) and 520 nm (green). The results are depicted in FIG. 3. It was determined that 2.7, and 31A5 decreased intracellular concentration of iron with an $IC_{50}$ of 14 nM and 30 nM, respectively. Antibodies 37A2, 37B9, 37C8, 37G8, 38A4, 38C8, 38D2, 38E3 and 38G6 decreased intracellular concentration of iron with an $IC_{50}$ of 4.5 nM, 3.6 nM, 0.8 nM, 1.6 nM, 0.4 nM, 0.9 nM, 10 nM, 15 nM and 4.3 nM, respectively.

Example 6—An Anti-Ferroportin Antibody Protects Ferroportin from Internalization and Degradation by Hepcidin A 293 cell line containing a doxycycline-inducible ferroportin (Fpn) expression construct with a C-terminal sequence encoding a V5 epitope tag was constructed. These 293/Fpn-V5 cells, taken from a 70-80% confluent culture, were plated at 5.0×10$^5$ cells/mL in DMEM (Invitrogen Cat#11965), 10% FBS (Invitrogen Cat#10099-141), PSQ (Invitrogen Cat#10378-016), 100 µg/mL doxycycline, 2.5 µg/mL ferric citrate, 100 µL/well (50,000 cells) in Poly-D Lysine coated plates (Becton-Dickinson Cat#35-6640) and incubated overnight or for at least 20 hours at 37° C. with 5% $CO_2$. The next day, media was removed from the wells and replaced with premade mixes of DMEM, 10% FBS, PSQ, 2.5 ug/mL ferric citrate, 37 nM recombinant human hepcidin and serial dilutions of the antibodies (2.7, 31A5, 37A2, 37B9, 37C8, 37G8, 38A4, 38C8, 38D2, and 38G6 and mIgG2 control antibody), all prepared in a 96-well polypropylene deep-well block plate immediately before addition to the assay plate. Mixtures were added at 100 µL/well and incubated overnight at 37° C., 5% $CO_2$ in a cell culture incubator.

Figure 4C:
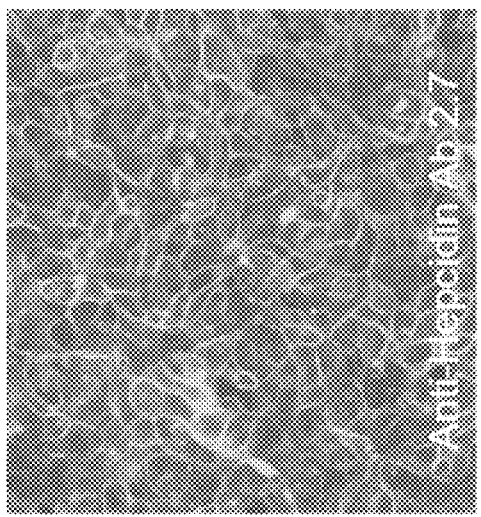
FIGS. 4A, 4B, and 4C are confocal micrographs depicting ferroportin cell surface expression in cells treated with hepcidin and mouse IgG2 control antibody, anti-ferroportin antibody 31A5 or anti-hepcidin antibody 2.7, respectively.
Figure 4B:
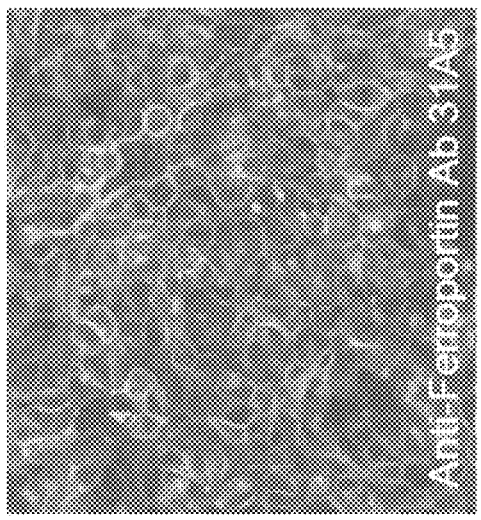
Figure 4A:
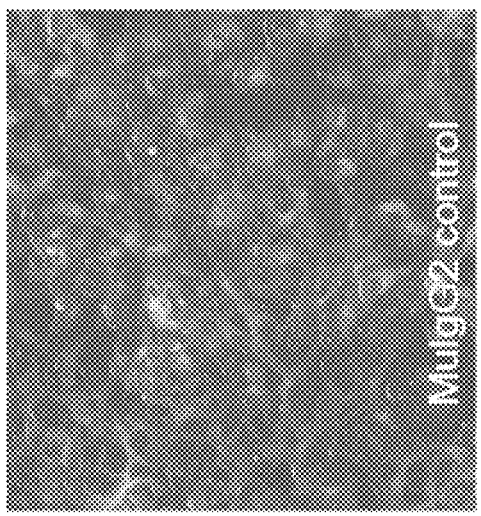
Figure 4D:
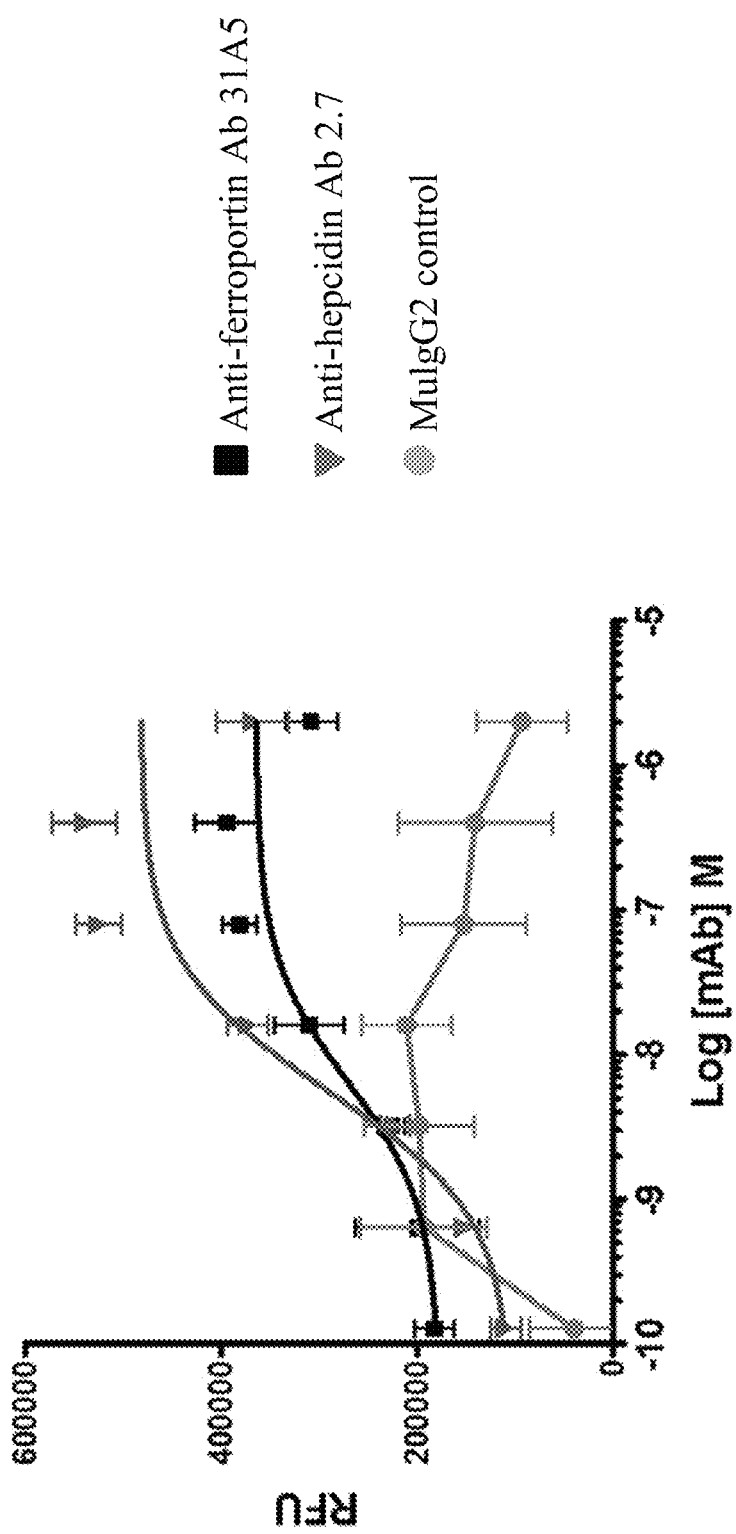
FIG. 4D is a plot of total fluorescence versus concentration of the indicated antibodies. The results show that anti-ferroportin antibody 31A5 protects ferroportin from internalization and degradation.

Ferroportin-V5-expressing cells were treated with 37 nM hepcidin and serial dilutions of the antibodies (mouse antibody 2.7 (anti-hepcidin antibody), human antibody 31A5 and mIgG2 control antibody) overnight. Cells were fixed, permeabilized and ferroportin-V5 was detected using a FITC-conjugated anti-V5 antibody. Ferroportin surface expression was detected using a confocal fluorescent microscope and the results are set forth in FIGS. 4A, 4B, and 4C. Total fluorescence was detected using a fluorometer and the results are set forth in FIG. 4D. Results confirmed that monoclonal 31A5 preserved ferroportin activity by preventing internalization and degradation of ferroportin. Antibodies 37A2, 37B9, 37C8, 37G8, 38A4, 38C8, 38D2, and 38G6 preserved ferroportin activity with an $IC_{50}$ of 2.5 nM, 0.2 nM, 0.2 nM, 0.8 nM, 2.8 nM, 0.3 nM, 5.4 nM, and 1.9 nM, respectively.

Example 7—Detection of Ferroportin by Immunohistochemistry

Figure 5A:
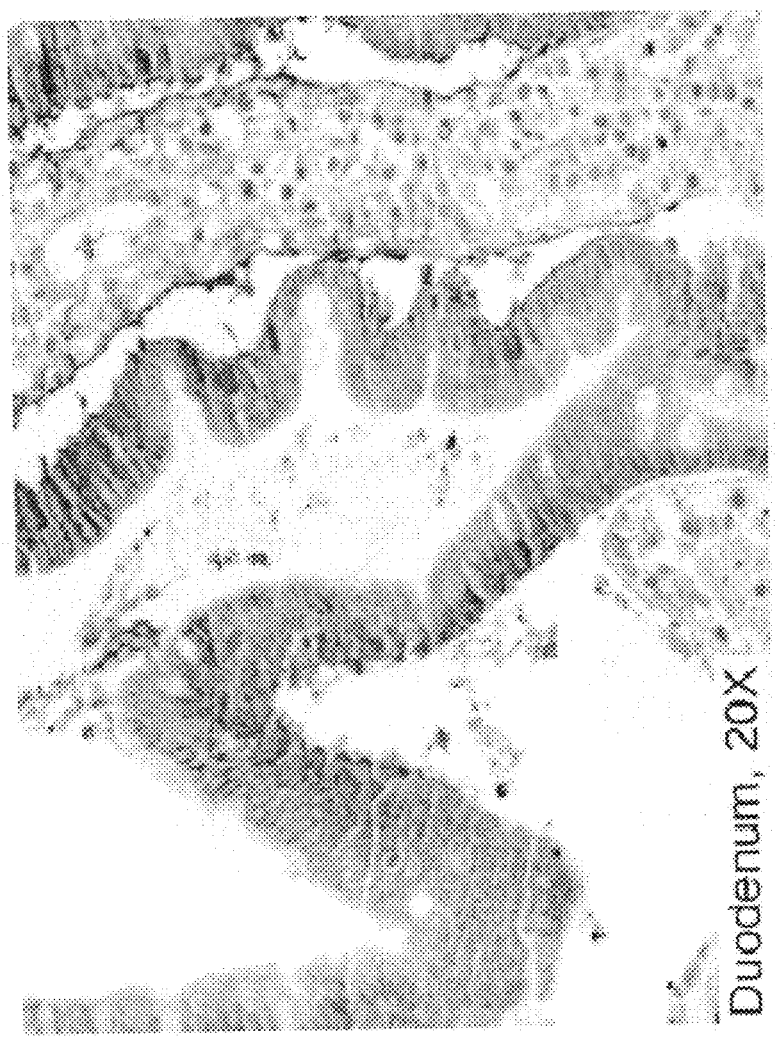
FIGS. 5A and 5B show that anti-ferroportin antibody 31A5 detects ferroportin expression on cells by immunohistochemistry.
Figure 5B:
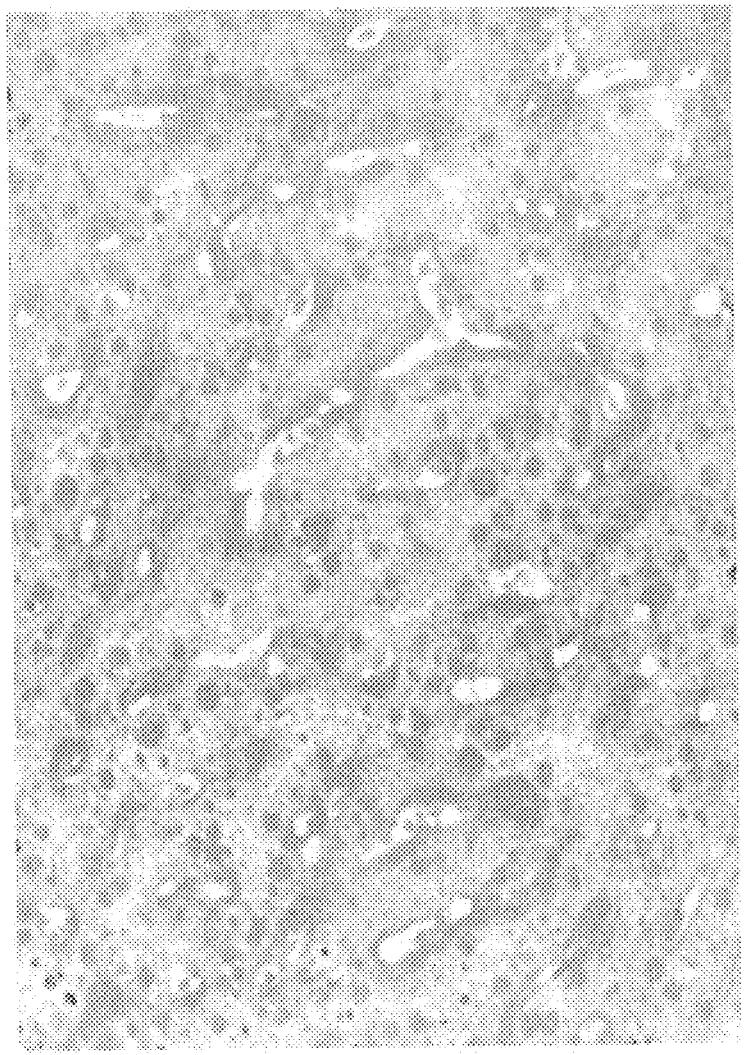

Mammalian ferroportin expression has been detected on the basolateral membrane of duodenal enterocytes and in macrophages of the reticuloendothelial system (Canonne-Hergaux, et al., Am J Physiol Gastrointest Liver Physiol., 290(1): p. G156-63, 2006; Donovan, A., et al., Cell Metab, 1(3): p. 191-200, 2005). Using 31A5, this expression profile has been confirmed in human tissue by IHC (FIGS. 5A and 5B).

Immunohistochemistry (IHC) for ferroportin was performed using a biotin-free immunoperoxidase staining method (Immunohistochemical Staining Methods, 4th ed, DAKO, 2006.); 3,3'-diaminobenzidine tetrahydrochloride (DAB) was used as the chromogen. Briefly, the slides were deparaffinized in xylene, hydrated in ascending grades of alcohol to water and superheated in antigen retrieval buffer. A series of blocking steps was used to eliminate endogenous FC receptors and endogenous peroxidase. Slides were then incubated with the mouse primary antibody. An HRP-conjugated secondary antibody polymer was then added and color was developed in DAB, a brown chromogen. Slides were counterstained in Hematoxlin, blued, dehydrated, cleared and coverslipped.

Additional data has been published suggesting that ferroportin is expressed in the mammalian placenta and regions of the CNS (Donavan et al., supra; Bastin et al., Br. J. Haematol., 134:532-543, 2006); however, a full characterization of ferroportin expression in humans using a monoclonal antibody has not yet been reported. A preliminary study using 31A5 and an Asterand human multi tissue array suggests that ferroportin is expressed in several different tissues (Table 3).

TABLE 3

Ferroportin expression as assessed by IHC using 31A5 and an Asterand multi tissue array.

| Tissue | Cells |
|---|---|
| Adrenal Cortex | Cortical cells |
| | Medullary cells |
| Brain | Astrocytes |
| | Neurons |
| | Capillary pericytes |
| Pituitary | Pars distalis cells |
| | Pars intermedia cells |
| Spinal cord | Axons |
| | Neurons |
| Placenta | Syncytiotrophoblasts |
| | Interstitial mononuclear cells |
| Lymph node | Dendritic cells in cortex |
| | Macrophages in cortex, medulla and subcapsular sinus |
| Breast | Interstitial mononuclear cells |
| Fallopian tube | Interstitial mononuclear cells |
| Esophagus | Interstitial mononuclear cells |
| Stomach | Interstitial mononuclear cells |
| Small intestine | Interstitial mononuclear cells |
| | Neurons of Myenteric plexus |
| Colon | Interstitial mononuclear cells |
| Kidney | Interstitial mononuclear cells |
| Liver | Kupffer cells |
| Lung | Alveolar/interstitial macrophages |
| Prostate | Interstitial mononuclear cells |
| Skin | Interstitial mononuclear cells |
| Spleen | Macrophages in red pulp |
| Striated skeletal muscle | Interstitial mononuclear cells |
| Testis | Interstitial mononuclear cells |
| Ureter | Interstitial mononuclear cells |
| Cervix | Interstitial mononuclear cells |

* Interstitial mononuclear cells may be monocytes, macrophages or dendritic cells This Example represents the first expression analysis performed for ferroportin using a monoclonal antibody.

For the sake of completeness of disclosure, all patent documents and literature articles cited herein are expressly incorporated in this specification by reference in their entireties.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method for increasing hemoglobin or hematocrit in a subject in need thereof comprising administering to the subject a therapeutically effective amount of an isolated monoclonal antibody that binds to an extracellular domain of human ferroportin and preserves ferroportin activity, wherein the monoclonal antibody binds to an epitope comprising amino acids 417-426 of SEQ ID NO: 16.

2. The method of claim 1, wherein the monoclonal antibody competes for binding to human ferroportin by at least 75% with an antibody comprising:

(i) a heavy chain variable region of SEQ ID NO: 4 and a light chain variable region of SEQ ID NO: 2;

(ii) a heavy chain variable region of SEQ ID NO: 28 and a light chain variable region of SEQ ID NO: 26;

(iii) a heavy chain variable region of SEQ ID NO: 38 and a light chain variable region of SEQ ID NO: 36;

(iv) a heavy chain variable region of SEQ ID NO: 48 and a light chain variable region of SEQ ID NO: 46;

(v) a heavy chain variable region of SEQ ID NO: 58 and a light chain variable region of SEQ ID NO: 56;

(vi) a heavy chain variable region of SEQ ID NO: 68 and a light chain variable region of SEQ ID NO: 66;

(vii) a heavy chain variable region of SEQ ID NO: 78 and a light chain variable region of SEQ ID NO: 76;

(viii) a heavy chain variable region of SEQ ID NO: 98 and a light chain variable region of SEQ ID NO: 96; or (ix) a heavy chain variable region of SEQ ID NO: 108 and a light chain variable region of SEQ ID NO: 106.

3. The method of claim 1, wherein the monoclonal antibody is a chimerized antibody, a humanized antibody, or a fully human antibody.

4. The method of claim 1, wherein the monoclonal antibody is an IgG1, IgG2, IgG3, or IgG4 antibody.

5. The method of claim 1, wherein the subject has a disorder of iron homeostasis.

6. The method of claim 5, wherein the disorder of iron homeostasis is anemia, anemia of inflammation, anemia of cancer, chemotherapy induced anemia, chronic inflammatory anemia, end stage renal disorder, chronic kidney disease (stage I, II, III, IV, or V), or iron deficiency anemia.

7. The method of claim 1, wherein the subject has a serum iron level outside of the range of 50 to 170 µg/dL.

8. The method of claim 1, wherein the therapeutically effective amount of the monoclonal antibody is effective to increase the red blood cell count in the subject following administration.

9. The method of claim 1, further comprising administering to the subject an erythropoiesis stimulator.

10. The method of claim 1, wherein the erythropoiesis stimulator is erythropoietin or variants thereof.

11. The method of claim 1, wherein the monoclonal antibody is administered to the subject by a parenteral route of administration.

12. The method of claim 1, wherein the monoclonal antibody is administered to the subject via an intravenous or subcutaneous injection.

* * * * *